US012498367B2

(12) United States Patent
Vasiljeva et al.

(10) Patent No.: US 12,498,367 B2
(45) Date of Patent: Dec. 16, 2025

(54) METHODS OF QUALITATIVELY AND/OR QUANTITATIVELY ANALYZING PROPERTIES OF ACTIVATABLE ANTIBODIES AND USES THEREOF

(71) Applicant: CytomX Therapeutics, Inc., South San Francisco, CA (US)

(72) Inventors: Olga Vasiljeva, Cupertino, CA (US); Stephen James Moore, Danville, CA (US); Bruce Howng, San Francisco, CA (US); Susan K. Lyman, South San Francisco, CA (US); Luc Roland Desnoyers, San Francisco, CA (US)

(73) Assignee: CytomX Therapeutics, Inc.

( * ) Notice: Subject to any disclaimer, the term of this patent is extended or adjusted under 35 U.S.C. 154(b) by 1039 days.

(21) Appl. No.: 16/632,265

(22) PCT Filed: Jul. 20, 2018

(86) PCT No.: PCT/US2018/043190

§ 371 (c)(1),
(2) Date: Jan. 17, 2020

(87) PCT Pub. No.: WO2019/018828

PCT Pub. Date: Jan. 24, 2019

(65) Prior Publication Data

US 2021/0025877 A1 Jan. 28, 2021

Related U.S. Application Data

(60) Provisional application No. 62/534,931, filed on Jul. 20, 2017.

(51) Int. Cl.

| | |
|---|---|
| ***G01N 33/543*** | (2006.01) |
| ***B01D 15/26*** | (2006.01) |
| ***C07K 1/16*** | (2006.01) |
| ***C07K 16/28*** | (2006.01) |
| ***G01N 30/02*** | (2006.01) |
| ***G01N 33/68*** | (2006.01) |

(52) U.S. Cl.

CPC ..... *G01N 33/54306* (2013.01); *B01D 15/265* (2013.01); *C07K 1/16* (2013.01); *C07K 16/2803* (2013.01); *C07K 16/2827* (2013.01); *C07K 16/2863* (2013.01); *C07K 16/2881* (2013.01); *G01N 30/02* (2013.01); *G01N 33/54366* (2013.01); *G01N 33/686* (2013.01); *G01N 2030/027* (2013.01)

(58) Field of Classification Search

None

See application file for complete search history.

(56) References Cited

U.S. PATENT DOCUMENTS

| | | | | |
|---|---|---|---|---|
| 4,485,045 | A | 11/1984 | Regen | |
| 4,544,545 | A | 10/1985 | Ryan et al. | |
| 5,013,556 | A | 5/1991 | Woodle et al. | |
| 5,030,719 | A | 7/1991 | Umemoto et al. | |
| 5,151,510 | A | 9/1992 | Stec | |
| 5,290,920 | A * | 3/1994 | Sindrey | C07K 14/485 530/412 |
| 5,338,834 | A * | 8/1994 | Williams | C07K 14/5412 530/416 |
| 7,465,790 | B2 | 12/2008 | Waldmann et al. | |
| 7,666,817 | B2 | 2/2010 | Daugherty et al. | |
| 7,914,656 | B2 | 3/2011 | Bukshpan et al. | |
| 8,513,390 | B2 | 8/2013 | Stagliano et al. | |
| 8,518,404 | B2 | 8/2013 | Daugherty et al. | |
| 8,529,898 | B2 | 9/2013 | Daugherty et al. | |
| 8,541,203 | B2 | 9/2013 | Daugherty et al. | |
| 8,563,269 | B2 | 10/2013 | Stagliano et al. | |
| 8,809,504 | B2 | 8/2014 | Lauermann | |
| 8,940,232 | B2 | 1/2015 | Roach et al. | |
| 9,169,321 | B2 | 10/2015 | Daugherty et al. | |
| 9,304,123 | B2 | 4/2016 | Powers et al. | |
| 9,400,277 | B2 | 7/2016 | Yang et al. | |
| 9,453,078 | B2 | 9/2016 | Stagliano et al. | |
| 9,766,206 | B2 | 9/2017 | Yang et al. | |
| 10,059,762 | B2 | 8/2018 | Stagliano et al. | |
| 10,077,300 | B2 | 9/2018 | Daugherty et al. | |
| 10,118,961 | B2 | 11/2018 | Stagliano et al. | |
| 2004/0109855 | A1 | 6/2004 | Waldmann et al. | |

(Continued)

FOREIGN PATENT DOCUMENTS

| | | |
|---|---|---|
| CA | 2997960 | 4/2017 |
| CN | 104540518 | 4/2015 |

(Continued)

OTHER PUBLICATIONS

Irving, B.A. (Feb. 2015) "Probodies Empower a New Generation of Antibody Immunotherapies," CytomX Therapeutics Inc. presentation at Keystone Symposia™ on Molecular and Cellular Biology, Feb. 8-13, 2015; 25 pages.
Proteinsimple, *Simple Western Size Assay Development Guide.* P/N 042-889, Revision 1, Mar. 2014; 96 pages.
Boulware et al., "Evolutionary optimization of peptide substrates for proteases that exhibit rapid hydrolysis kinetics," Biotechnology and Bioengineering, Jun. 15, 2010, 106(3):339-346.
Bowie et al., "A method to identify protein sequences that fold into a known three-dimensional structure," Science, Jul. 12, 1991, 253(5016):164-170.

(Continued)

*Primary Examiner* — Sharon X Wen
(74) *Attorney, Agent, or Firm* — Fish & Richardson P.C.

(57) ABSTRACT

The invention provides methods and kits for qualitatively and/or quantitatively analyzing activation and other properties of activatable antibody therapeutic in biological samples, including tissues and/or biofluid samples. The invention also relates to methods of using a capillary-based immunoassay platform to qualitatively and/or quantitatively analyze levels of activation in biological samples, including tissues and/or biofluid samples.

34 Claims, 15 Drawing Sheets

Specification includes a Sequence Listing.

(56) References Cited

U.S. PATENT DOCUMENTS

| | | | | |
|---|---|---|---|---|
| 2004/0259269 | A1 | 12/2004 | Lin et al. | |
| 2005/0000811 | A1* | 1/2005 | Luka | B01L 3/50255 204/600 |
| 2008/0017512 | A1 | 1/2008 | Bordunov et al. | |
| 2009/0023156 | A1 | 1/2009 | Voss et al. | |
| 2009/0304719 | A1 | 12/2009 | Daugherty et al. | |
| 2010/0173398 | A1* | 7/2010 | Peterman | B01L 3/502761 204/600 |
| 2010/0184112 | A1* | 7/2010 | Huang | C12Q 1/37 204/461 |
| 2010/0189651 | A1 | 7/2010 | Stagliano et al. | |
| 2010/0330579 | A1* | 12/2010 | Birkner | C12Q 1/686 435/6.12 |
| 2011/0011740 | A1 | 1/2011 | Roach et al. | |
| 2012/0149061 | A1 | 6/2012 | Stagliano et al. | |
| 2012/0207756 | A1 | 8/2012 | Stagliano et al. | |
| 2012/0237512 | A1 | 9/2012 | Daugherty et al. | |
| 2012/0237977 | A1 | 9/2012 | Daugherty et al. | |
| 2012/0244154 | A1 | 9/2012 | Daugherty et al. | |
| 2013/0309230 | A1 | 11/2013 | Stagliano et al. | |
| 2014/0024810 | A1 | 1/2014 | West et al. | |
| 2014/0045195 | A1 | 2/2014 | Daugherty et al. | |
| 2014/0363430 | A1 | 12/2014 | West et al. | |
| 2015/0079088 | A1 | 3/2015 | Lowman et al. | |
| 2015/0093757 | A1 | 4/2015 | Gavin | |
| 2015/0218217 | A1* | 8/2015 | Moore | A61K 47/6803 530/391.1 |
| 2016/0122425 | A1 | 5/2016 | Daugherty et al. | |
| 2016/0194399 | A1* | 7/2016 | Irving | A61K 47/6879 435/69.6 |
| 2016/0228546 | A1 | 8/2016 | Stagliano et al. | |
| 2016/0311903 | A1 | 10/2016 | West et al. | |
| 2017/0081397 | A1 | 3/2017 | Stagliano et al. | |
| 2018/0106758 | A1 | 4/2018 | Yang et al. | |
| 2019/0119370 | A1 | 4/2019 | Stagliano et al. | |
| 2019/0211089 | A1 | 7/2019 | Daugherty et al. | |

FOREIGN PATENT DOCUMENTS

| | | | | |
|---|---|---|---|---|
| CN | 107249602 | | 10/2017 | |
| EP | 1 523 503 | B1 | 4/2009 | |
| EP | 1 324 771 | B1 | 6/2011 | |
| EP | 2795335 | B1 * | 9/2017 | G01N 33/53 |
| JP | 2009031001 | | 2/2009 | |
| JP | 2011209301 | | 10/2011 | |
| JP | 2015516813 | | 6/2015 | |
| WO | WO 1994/011026 | | 5/1994 | |
| WO | WO 2001/91798 | A2 | 12/2001 | |
| WO | WO 2002/030460 | A2 | 4/2002 | |
| WO | WO 2004/009638 | A1 | 1/2004 | |
| WO | WO 2006/014680 | A1 | 2/2006 | |
| WO | WO 2007/105027 | A1 | 9/2007 | |
| WO | WO 2009/025846 | A2 | 2/2009 | |
| WO | WO 2010/081173 | A2 | 7/2010 | |
| WO | WO 2013/092611 | | 6/2013 | |
| WO | WO 2013/163631 | A2 | 10/2013 | |
| WO | WO 2013/192546 | A1 | 12/2013 | |
| WO | WO 2014/026136 | A2 | 2/2014 | |
| WO | WO 2015/048458 | A2 | 4/2015 | |
| WO | WO 2016/014974 | | 1/2016 | |
| WO | WO 2016/046220 | | 3/2016 | |
| WO | WO 2016/118629 | A1 | 7/2016 | |
| WO | WO 2016/138038 | A1 | 9/2016 | |
| WO | WO 2016/187535 | A2 | 11/2016 | |
| WO | WO 2016/196726 | A1 | 12/2016 | |
| WO | WO 2017/011580 | A2 | 1/2017 | |
| WO | WO 2017/062672 | | 4/2017 | |
| WO | WO 2017/123970 | A1 | 7/2017 | |
| WO | WO 2018/102411 | A1 | 6/2018 | |
| WO | WO 2019/018828 | A1 | 1/2019 | |

OTHER PUBLICATIONS

Chothia et al., "Canonical structures for the hypervariable regions of immunoglobulins," Journal of Molecular Biology, Aug. 20, 1987, 196(4):901-917.
Chothia et al., "Conformations of immunoglobulin hypervariable regions," Nature, Dec. 1989, 342(6252):877-883.
Davies et al., "Antibody-antigen complexes," Annual Review of Biochemistry, Jul. 1990, 59(1):439-473.
Eppstein et al., "Biological activity of liposome-encapsulated murine interferon gamma is mediated by a cell membrane receptor," Proceedings of the National Academy of Sciences, Jun. 1, 1985, 82(11):3688-3692.
Hwang et al., "Hepatic uptake and degradation of unilamellar sphingomyelin/cholesterol liposomes: a kinetic study," Proceedings of the National Academy of Sciences, Jul. 1, 1980, 77(7):4030-4034.
International Preliminary Report on Patentability in International Application No. PCT/US2018/043190, dated Jan. 21, 2020, 7 pages.
International Search Report and Written Opinion in International Application No. PCT/US2018/043190, dated Oct. 30, 2018, 1 pages.
Jansen et al., "Immunotoxins: hybrid molecules combining high specificity and potent cytotoxicity," Immunological reviews, Feb. 1982, 62(1):185-216.
Killen et al., "Specific killing of lymphocytes that cause experimental autoimmune myasthenia gravis by ricin toxin-acetylcholine receptor conjugates," Jour. Immun., Nov. 1984, 133:1335-2549.
LaPlanche et al., "Phosphorothioate-modified oligodeoxyribonucleotides. III. NMR and UV spectroscoptc studies of the R p-R p, S p-S p, and R p-S p duplexes,[d(GGsAATTCC)]2, derived from diastereomeric O-ethyl phosphorothioates," Nucleic acids research, Nov. 11, 1986, 14(22):9081-9093.
LeBeau et al., "Imaging a functional tumorigenic biomarker in the transformed epitheliu," Proceedings of the National Academy of Sciences, Jan. 2, 2013, 110(1):93-98.
Malmqvist et al., "Biospecific interaction analysis using biosensor technology," Nature, Jan. 14, 1993, 361: 186-187.
Martin et al., "Irreversible coupling of immunoglobulin fragments to preformed vesicles. An improved method for liposome targeting," Journal of Biological Chemistry, Jan. 10, 1982, 257(1):286-288.
Mitra et al., "Reagents for the crosslinking of proteins by equilibrium transfer alkylation," Journal of the American Chemical Society, May 23, 1979, 101(11):3097-3110.
Overall et al., "Validating matrix metalloproteinases as drug targets and anti-targets for cancer therapy," Nature Reviews Cancer, Mar. 2006, 6(3):227-239.
Ramakrishnan et al., "Comparison of the selective cytotoxic effects of immunotoxins containing ricin A chain or pokeweed antiviral protein and anti-Thy 1.1 monoclonal antibodies," Cancer research, Jan. 1, 1984, 44(1):201-208.
Scheraga, "Predicting Three-Dimensional Structures of Oligopeptides," Reviews Computational Chemistry III, 1992, 73-142.
Stec et al., "Automated solid-phase synthesis, separation, and stereochemistry of phosphorothioate analogs of oligodeoxyribonucleotides," Journal of the American Chemical Society, Oct. 1, 1984, 106(20):6077-6079.
Stein et al., "Physicochemical properties of phospborothioate oligodeoxynucleotides," Nucleic Acids Research, 1988, 16(8): 3209-3221.
Thornton et al., "Prediction of progress at last," Nature, Nov. 1991, 354(6349):105-106.
Uhlmann et al., "Antisense oligonucleotides: a new therapeutic principle," Chemical Reviews, 1990, 90(4):543-584.
Vitetta et al., "Redesigning nature's poisons to create anti-tumor reagents," Science, Nov. 20, 1987, 238(4830):1098-1104.
Zon et al., "Oligonucleotides and Analogues: A Practical Approach," 1991, 87-108.
Zon et al., "Phosphorothioate oligonucleotides: chemistry, purification, analysis, scale-up and future directions," Anticancer Drug Design, Dec. 1991, 6:539.

(56) References Cited

OTHER PUBLICATIONS

International Search Report and Written Opinion in International Application No. PCT/US2018/043190, dated Oct. 30, 2018, 13 pages.
Chen et al., "Absolute quantitation of endogenous proteins with precision and accuracy using a capillary Western system," Analytical Biochemistry, Nov. 1, 2013, 442(1):97-103.
Nguyen et al., "The Simple Western TM: a gel-free, blot-free, hands-free Western blotting reinvention," Nature Methods, Oct. 28, 2011, 8:v-vi.
p4eu.org [online], "Protein Characterization in Vienna: Microscale Thermophoresis and Simple Western," Nov. 11-12, 2013, retrieved on May 19, 2023, retrieved from URL <https://p4eu.org/P4EU-Inhalt/uploads/2017/06/012_Protein-Characterization-in-Vienna.pdf>, 27 pages.
Guanghui et al., "Capillary Electrophoresis Immunoassay Studies Cancerous Embryonic Antigens," Chinese Journal of Analysis Laboratory, Nov. 2006, 25(11):9 pages (with English translation).
Howng et al., "Novel Ex Vivo Zymography Approach for Assessment of Protease Activity in Tissues With Activatable Antibodies," Pharmaceutics, Sep. 2, 2021, 13(9):1390.
Thermofisher.com [online], "Magnetic Beads for Immunoprecipitation," retrieved on Oct. 9, 2024, retrieved from URL <https://www.thermofisher.com/us/en/home/life-science/protein-biology/protein-assays-analysis/immunoprecipitation.html>, 7 pages.
Hellström et al., "Epitope mapping and use of anti-idiotypic antibodies to the L6 monoclonal anticarcinoma antibody," Cancer Res, Apr. 15, 1990, 50(8):2449-54.

* cited by examiner

METHODS OF QUALITATIVELY AND/OR QUANTITATIVELY ANALYZING PROPERTIES OF ACTIVATABLE ANTIBODIES AND USES THEREOF

CROSS-REFERENCE TO RELATED APPLICATIONS

This application is the United States National Phase Application under 35 U.S.C. § 371 of International Patent Application No. PCT/US2018/043190 filed on Jul. 20, 2018, and which claims the benefit pursuant 35 U.S.C. § 119(e) of U.S. Provisional Application No. 62/534,931, filed Jul. 20, 2017, the contents of which is incorporated herein by reference in its entirety.

INCORPORATION-BY-REFERENCE OF SEQUENCE LISTING

The contents of the text file named CYTM-053_001US_SeqList_ST25 which was created on Apr. 16, 2020, and is 115 kilobytes in size, are incorporated herein by reference in their entirety.

FIELD OF THE INVENTION

The invention relates generally to methods for qualitatively and/or quantitatively analyzing activation and other properties of activatable antibody therapeutic in biological samples, including tissues and/or biofluid samples. The invention also relates to methods of using a capillary-based immunoassay platform to qualitatively and/or quantitatively analyze levels of activation in biological samples, including tissues and/or biofluid samples.

BACKGROUND OF THE INVENTION

Antibody-based therapies have proven effective treatments for several diseases but in some cases, toxicities due to broad target expression have limited their therapeutic effectiveness. In addition, antibody-based therapeutics have exhibited other limitations such as rapid clearance from the circulation following administration. In the realm of small molecule therapeutics, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects.

To overcome the limitations of antibody-based therapeutics, activatable antibody-based therapeutics have been designed.

There exists a need to be able to monitor and quantitatively analyze activation of such activatable antibody-based therapeutics.

SUMMARY OF THE INVENTION

The present invention is directed to a method of quantitating a level of activation of an activatable antibody, the method comprising:

i) contacting a loaded capillary or population of loaded capillaries with a biological sample comprising one or more components selected from the group consisting of an activatable antibody, an activated activatable antibody, and a combination thereof;

wherein the loaded capillary or population of loaded capillaries is/are pre-loaded with a stacking matrix and a separation matrix;

ii) separating one or more high molecular weight (MW) components of the biological sample from one or more low molecular weight (MW) components of the biological sample within each capillary;

iii) immobilizing the high MW components and the low MW components within each capillary;

iv) immunoprobing each capillary with at least a first reagent that is specific for at least one activatable antibody; and v) detecting and quantitating a level of the first reagent in each capillary or population of capillaries.

In one embodiment, step ii) comprises separating high molecular weight components of the biological sample from low molecular weight components of the biological sample within each capillary by capillary electrophoresis.

In a further embodiment, the activatable antibody is selected from the group consisting of a conjugated activatable antibody, a multispecific activatable antibody, and a conjugated multispecific activatable antibody.

In some embodiments, the first reagent comprises an anti-idiotypic antibody or antigen-binding fragment thereof. In another embodiment, step iv) further comprises loading each capillary with a second reagent that specifically binds to the first reagent. In some embodiments, the second reagent is detectably labelled. In other embodiments, the second reagent is not detectably labelled and step iv) further comprises loading each capillary with a third reagent that specifically binds to the second reagent.

In a still further embodiment, the present invention provides a kit comprising:

(i) an activatable antibody standard curve reagent;

(ii) an activated activatable antibody standard curve reagent; and (iii) an anti-id primary antibody having binding specificity for the activatable antibody.

BRIEF DESCRIPTION OF THE DRAWINGS

FIG. 1A is an electropherogram showing 17G1 detection of decreasing concentration of one arm activated PL07-2001-C5H9v2 (1, 0.33, and 0.11 ug/ml, referred to in the FIG. as AA MIX). FIG. 1B demonstrates relative activation percent for the top 6 clones of one arm activated activatable antibody. The relative activation rate is preserved at different concentrations. 21H10 and 27C1 clones have lower affinity resulting in no data for the 0.11 ug/ml concentration.

FIG. 3A demonstrates detection of the anti-PDL1 activatable antibody referred to herein as PL07-2001-C5H9v2 in plasma of mice treated with 10 mg/kg of PL07-2001-C5H9v2 using a commercial A110UK (Goat Anti-Human IgG (H&L) adsorbed against monkey unlabeled) from American Qualex (available on the web at aqsp.com/). FIG. 3B demonstrates detection of PL07-2001-C5H9v2 in plasma of mice treated with 0.1 mg/kg of PL07-2001-C5H9v2 using an anti-idiotypic 17G1 antibody.

FIGS. 4A and 4B demonstrate the analysis of tumor homogenate and plasma samples by the capillary electrophoresis immunoassay method of the present invention.

FIGS. 5A and 5B demonstrate the analysis of tumor homogenate and plasma samples by the capillary electrophoresis immunoassay method of the present invention.

FIGS. 6A and 6B demonstrate the analysis of tumor homogenate and plasma samples by the capillary electrophoresis immunoassay method of the present invention.

FIGS. 7A and 7B demonstrate the analysis of tumor homogenate and plasma samples by the capillary electrophoresis immunoassay method of the present invention.

DETAILED DESCRIPTION OF THE INVENTION

Figure 1A:
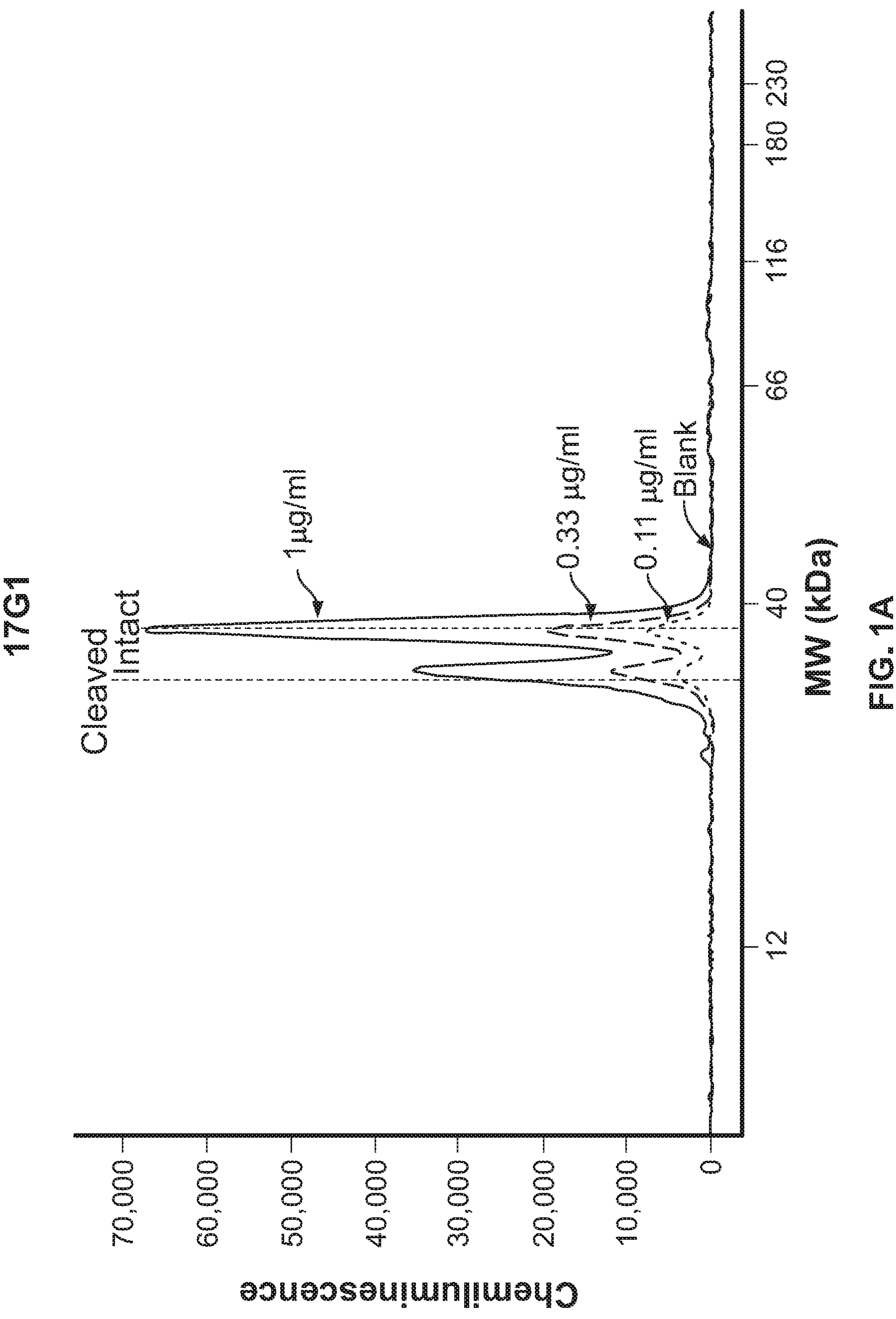
FIGS. 1A and 1B are a series of graphs depicting screening of PL07-2001-C5H9v2 anti-idiotypic (anti-id) clones against 37% one-armed activated activatable antibody at 0.11, 0.33 and 1 ug/ml in human plasma at 1:100.

The disclosure provides methods and kits for qualitatively and/or quantitatively analyzing activation and other properties of activatable antibody activation in biological samples, including tissues and/or biofluid samples, using a capillary-based immunoassay platform.

Activatable antibodies typically include at least the following: (i) an antibody or an antigen binding fragment thereof (AB) that specifically binds a target; (ii) a masking moiety (MM) coupled to the AB such that, when the activatable antibody is in an uncleaved or intact state, inhibits the binding of the AB to the target; and (iii) a cleavable moiety (CM) coupled to the AB, wherein the CM is a polypeptide that functions as a substrate for a protease. Activatable antibodies are generally activated when the substrate of the CM is in the presence of the protease for which it functions as a substrate, and the protease cleaves the substrate of the CM, thus generating an "activated" (or "cleaved") activatable antibody. Activatable antibodies may also be in the form of a conjugated activatable antibody, a multispecific activatable antibody, a conjugated multispecific activatable antibody, and the like. Activatable antibodies are described in more detail herein below.

It is useful to be able to qualitatively and/or quantitatively measure properties of activatable antibodies in biological samples, such as, for example, the level of activation of the activatable antibodies in a biological sample, the total amount of activated, i.e., cleaved, activatable antibodies and/or intact, i.e., inactivated, activatable in a biological sample, or any combination or correlation thereof. Such methods are useful in monitoring efficacy of activatable antibodies and activatable antibody-based therapeutics at any stage of development and/or therapeutic treatment. For example, in some embodiments, the methods and kits provided herein are useful for testing efficacy of activatable antibodies and activatable antibody-based therapeutics prior to administration to a subject in need thereof and/or during the treatment regimen to monitor efficacy of the activatable antibodies and activatable antibody-based therapeutics throughout the entire administration period and/or after the administration period. In some embodiments, the methods and kits provided herein are useful to provide retrospective analysis of activatable antibodies and activatable antibody-based therapeutics.

In some embodiments, the disclosure provides methods of quantitating a level of activation of an activatable antibody, the method comprising:

i) contacting a loaded capillary or population of loaded capillaries with a biological sample comprising one or more components selected from the group consisting of an activatable antibody, an activated activatable antibody, and a combination thereof;

wherein the loaded capillary or population of loaded capillaries is/are pre-loaded with a stacking matrix and a separation matrix;

ii) separating one or more high molecular weight (MW) components of the biological sample from one or more low molecular weight (MW) components of the biological sample within each capillary;

iii) immobilizing the high MW components and the low MW components within each capillary;

iv) immunoprobing each capillary with at least a first (primary) reagent that is specific for at least one activatable antibody; and v) detecting and quantitating a level of the first (primary) reagent in each capillary or population of capillaries.

In some embodiments, the method further includes, prior to step i), loading at least one capillary or a population of capillaries with a stacking matrix and a separation matrix to generate the at least one loaded capillary or a population of loaded capillaries.

As used herein, the term "stacking matrix" refers to a highly porous (relative to the separation matrix) material that functions to concentrate proteins present in the biological sample and "stack" them at the interface with the separation matrix so that the proteins start migration under electrophoresis conditions from the same physical starting point. Suitable stacking matrices employed in the practice of the present invention may be prepared from the same materials and compositions used to prepare stacking gels for Western blotting methods (e.g., acrylamide, 0.5 M Tris-HCl (pH 6.8), SDS, water, ammonium persulfate, and N,N,N',N'-tetramethylethylenediamine (TEMED); and the like). The term "separation matrix" refers herein to a material that facilitates the separation of proteins based on their molecular weight under electrphoretic conditions. Suitable separation matrices employed in the practice of the present invention may be prepared from the same materials and compositions used to prepare separation gels for Western blotting methods (e.g, water, acrylamide, Tris-HCl (pH 8.8), SDS, TMED, ammonium persulfate; and the like). Capillaries pre-loaded with stacking matrix and separation matrix may be obtained commercially, for example, from ProteinSimple (supplier of the Wes™ Separation Module capillary cartridges and related reagents for use on the Wes™ capillary electrophoresis immunoassay system).

The loaded capillary or population of loaded capillaries are then contacted with a biological sample to initiate the loading of the biological sample into each loaded capillary. The biological sample typically comprises at least one relatively high molecular weight component that is an (intact or uncleaved) activatable antibody (including, for example, a conjugated activatable antibody, a multispecific activatable antibody, a conjugated multispecific activatable antibody, and the like) and at least one relatively low molecular weight component that is a (cleaved) activated activatable antibody. Often, the biological sample comprises both an (intact or uncleaved) activatable antibody and an (cleaved) activated activatable antibody species. In some embodiments, the biological sample comprises a bodily fluid from a subject. In some embodiments, the bodily fluid is isolated from anywhere in the body of the subject. In some embodiments, the bodily fluid is blood or a blood component such as plasma or serum. In some embodiments, the biological sample comprises cell culture supernatant. In some embodiments, the biological sample comprises a tissue sample from a subject. The tissue sample can be isolated from anywhere in the body of the subject. In some embodiments, the tissue sample is a tumor sample.

In some embodiments, the biological sample is from a mammal, such as a human, non-human primate, companion animal (e.g., cat, dog, horse), farm animal, work animal, or zoo animal. In some embodiments, the subject is a human. In some embodiments, the subject is a companion animal. In some embodiments, the subject is an animal in the care of a veterinarian.

In some embodiments, step i) comprises loading approximately 1-500 ng of biological sample or any value and/or range in between approximately 1-500 ng of biological sample. In some embodiments, step i) comprises loading approximately 5-40 ng of biological sample. In some embodiments, the biological sample is prepared using one or more buffers in an amount sufficient to result in molecular weight separation. In some embodiments, the biological sample is prepared using one or more SDS-containing buffers in an amount sufficient to result in molecular weight separation.

Separating the one or more high molecular weight component(s) (e.g., (intact activatable antibody) from the one or more low molecular weight component(s) (e.g., (cleaved) activated activatable antibody) of the biological sample in each capillary may be achieved by subjecting each capillary to electrophoresis. Electrophoresis causes the compounds in the biological sample to migrate through the separation gel at differential rates according to molecular size (e.g., molecular weight). In some embodiments, separation is carried out for a time period (i.e., "separation time") of less than about 35 minutes. Often, the separation time is at least about 35 minutes, or at least about 36 minutes, or at least about 37 minutes, or at least about 38 minutes.

Any suitable immobilization method and reagents may be used to immobilize high and low molecular weight components within each capillary (e.g., to the internal surfaces of each capillary). In some embodiments, step iii) comprises using UV light to immobilize the high MW components (e.g., (intact) activatable antibody) and the low MW components (e.g., (cleaved) activated activatable antibody) of the biological sample. This step results in the immobilization of any (intact) activatable antibody and (cleaved) activated activatable antibody present in the biological sample. A suitable system for performing capillary electrophoresis and immobilization steps is the Wes™ capillary electrophoresis immunoassay system (ProteinSimple).

In carrying out the method of the invention, a first reagent, having a binding specificity for at least one activatable antibody is used to immunoprobe each capillary. Typically, the first reagent is a primary antibody. Often, the first reagent comprises an anti-idiotypic (id) antibody or antigen-binding fragment thereof. When the MM and CM of the activatable antibody are conjugated to a light chain of the activatable antibody, an anti-idiotypic antibody or antigen-binding fragment thereof will typically be employed that binds to the variable light chain (VL) region of the activatable antibody. Often in these embodiments, the anti-idiotypic antibody or antigen-binding fragment thereof has a binding specificity for a VL CDR selected from the group consisting of VL CDR1, VL CDR2, and VL CDR3. When the MM and CM of the activatable antibody are conjugated to a heavy chain of the activatable antibody, an anti-idiotypic antibody or antigen-binding fragment thereof will typically be employed that binds to the variable heavy chain (VH) region of the activatable antibody. In these embodiments, the anti-idiotypic antibody or antigen-binding fragment thereof often has a binding specificity for a VH CDR selected from the group consisting of VH CDR1, VH CDR2, and VH CDR3. In some embodiments, it may be desirable to use a combination of two or more anti-idiotypic antibody species (or antigen-binding fragments thereof). Exemplary anti-id antibodies and their uses in the methods of the present invention are described in the Examples hereinbelow.

Detection of the first reagent may be accomplished in a variety of ways. For example, in one embodiment, step v) further comprises immunoprobing each capillary with a further second reagent that specifically binds to or recognizes the first reagent. In this embodiment, each capillary is loaded with the second reagent. Typically, the second reagent comprises a secondary antibody that specifically binds to the first reagent.

In some embodiments, the first and/or second reagent is detectably labeled. As used herein, the term "detectable label" refers to a moiety that may be directly or indirectly detected, such as, for example, a fluorescent label, a reporter enzyme (used in combination with, for example, a chemiluminescent substrate, a colorimetric substrate, and the like), and the like. Exemplary reporter enzymes include, for example, a peroxidase (e.g., horseradish peroxidase (HRP), and the like), alkaline phosphatase, and the like. Exemplary detectably labeled second reagents that are suitable for use in the practice of the invention include HRP-conjugated anti-mouse secondary antibody, HRP-conjugated anti-goat secondary antibody, HRP-conjugated anti-human secondary antibody, and the like. Often, a chemiluminescent substrate is added to provide the signal that is ultimately detected. Suitable chemiluminescent substrate systems are known in the art and include, for example luminol+peroxide, and the like.

In other embodiments, the second reagent is not detectably labeled (e.g., is not conjugated to any detectable label, such as, for example, a reporter enzyme). In this embodiment, the second reagent is typically a secondary antibody that usually is conjugated to a first binding tag of a set of first and second binding tags, wherein the first binding tag is capable of binding to the second binding tag. The method is carried out wherein step v) further comprises loading each capillary with a third (tertiary) reagent that specifically binds to the second reagent. The third reagent typically comprises the second binding tag and a detectable label, such as, for example a reporter enzyme or a fluorescent label. Exemplary first and second binding tags include biotin and streptavidin; streptavidin and biotin; biotin and avidin; and avidin and biotin; and the like, respectively. This "tertiary detection method" appears to enhance the signal associated with activatable antibody and activatable antibody species, thus making facile the detection and quantitation steps. Illustrative second and third reagents employed in this embodiment include a second reagent that is a secondary antibody conjugated to streptavidin and third reagent that is a reporter enzyme conjugated to biotin (e.g., HRP-conjugated biotin). A chemiluminescence system is typically used to generate the signal that is ultimately detected (e.g., luminol+peroxide). This method is illustrated in Example 11 herein.

In some embodiments, the at least one detectable reagent in step v) comprises at least a first reagent that is specific for at least one activatable antibody, conjugated activatable antibody, multispecific activatable antibody, conjugated multispecific activatable antibody, or combination thereof and a second reagent that specifically binds to or recognizes the first reagent, wherein the second reagent comprises a detectable label.

In some embodiments, step v) comprises quantitating a level of detectable label in each capillary or population of capillaries.

In some embodiments, the first reagent in step iv) is an antibody or antigen-binding fragment thereof that specifically binds to at least one activatable antibody, conjugated activatable antibody, multispecific activatable antibody, conjugated multispecific activatable antibody, or combination thereof. In some embodiments, the second reagent in step iv) is a detectably labeled secondary antibody that specifically binds to the first reagent. In some embodiments, the first reagent in step iv) is a primary antibody or antigen-binding fragment thereof that specifically binds to at least one activatable antibody, conjugated activatable antibody, multispecific activatable antibody, conjugated multispecific activatable antibody, or combination thereof, and the second reagent in step iv) is a detectably labeled secondary antibody that specifically binds to the primary antibody or antigen-binding fragment thereof. In some embodiments, the detectable label is conjugated to the second reagent. In some embodiments, the detectable label is horseradish peroxidase (HRP).

In some embodiments, the primary reagent, the secondary reagent, and/or the tertiary reagent, or each of the primary reagent, the secondary reagent, and the tertiary reagent is an antibody or antigen-binding fragment thereof. In some embodiments, the antibody or antigen-binding fragment thereof that binds a target is a monoclonal antibody, a domain antibody, a single chain antibody, a Fab fragment, a $F(ab')_2$ fragment, a scFv, a scAb, a dAb, a single domain heavy chain antibody, or a single domain light chain antibody. In some embodiments, such an antibody or antigen-binding fragment thereof that binds a target is a mouse, other rodent, chimeric, humanized or fully human monoclonal antibody.

In some embodiments, the primary antibody that specifically binds to at least one activatable antibody, conjugated activatable antibody, multispecific activatable antibody, conjugated multispecific activatable antibody, or combination thereof is generated using the methods described herein, for example, in Example 1.

In some embodiments, the primary antibody that specifically binds to at least one activatable antibody, conjugated activatable antibody, multispecific activatable antibody, conjugated multispecific activatable antibody, or combination thereof comprises a variable heavy chain complementarity determining region 1 (CDRH1) comprising the amino acid sequence SYGMS (SEQ ID NO: 438); a variable heavy chain complementarity determining region 2 (CDRH2) comprising the amino acid sequence TISPSGIYTYYPVTVKG (SEQ ID NO: 439); a variable heavy chain complementarity determining region 3 (CDRH3) comprising the amino acid sequence HHPNYGSTYLYYIDY (SEQ ID NO: 440); a variable light chain complementarity determining region 1 (CDRL1) comprising the amino acid sequence KSSQSVFSSSNQKNYLA (SEQ ID NO: 441); a variable light chain complementarity determining region 2 (CDRL2) comprising the amino acid sequence WAFTRES (SEQ ID NO: 442); and a variable light chain complementarity determining region 3 (CDRL3) comprising the amino acid sequence YQYLSSLT (SEQ ID NO: 443).

In some embodiments, the primary antibody that specifically binds to at least one activatable antibody, conjugated activatable antibody, multispecific activatable antibody, conjugated multispecific activatable antibody, or combination thereof comprises a variable heavy chain comprising the amino acid sequence of SEQ ID NO: 429.

In some embodiments, the primary antibody that specifically binds to at least one activatable antibody, conjugated activatable antibody, multispecific activatable antibody, conjugated multispecific activatable antibody, or combination thereof comprises a variable light chain comprising the amino acid sequence of SEQ ID NO: 431.

In some embodiments, the primary antibody that specifically binds to at least one activatable antibody, conjugated activatable antibody, multispecific activatable antibody, conjugated multispecific activatable antibody, or combination thereof comprises a variable heavy chain comprising the amino acid sequence of SEQ ID NO: 429, and a variable light chain comprising the amino acid sequence of SEQ ID NO: 431.

In some embodiments, the primary antibody that specifically binds to at least one activatable antibody, conjugated activatable antibody, multispecific activatable antibody, conjugated multispecific activatable antibody, or combination thereof comprises an amino acid sequence that is at least 90%, 91%, 92%, 93%, 94%, 95%, 96%, 97%, 98%, 99% or more identical to a variable heavy chain comprising the amino acid sequence of SEQ ID NO: 429.

In some embodiments, the primary antibody that specifically binds to at least one activatable antibody, conjugated activatable antibody, multispecific activatable antibody, conjugated multispecific activatable antibody, or combination thereof comprises an amino acid sequence that is at least 90%, 91%, 92%, 93%, 94%, 95%, 96%, 97%, 98%, 99% or more identical to a variable light chain comprising the amino acid sequence of SEQ ID NO: 431.

In some embodiments, the primary antibody that specifically binds to at least one activatable antibody, conjugated activatable antibody, multispecific activatable antibody, conjugated multispecific activatable antibody, or combination thereof comprises an amino acid sequence that is at least 90%, 91%, 92%, 93%, 94%, 95%, 96%, 97%, 98%, 99% or more identical to a variable heavy chain comprising the amino acid sequence of SEQ ID NO: 429, and an amino acid sequence that is at least 90%, 91%, 92%, 93%, 94%, 95%, 96%, 97%, 98%, 99% or more identical to a variable light chain comprising the amino acid sequence of SEQ ID NO: 431.

In some embodiments, the primary antibody that specifically binds to at least one activatable antibody, conjugated activatable antibody, multispecific activatable antibody, conjugated multispecific activatable antibody, or combination thereof comprises a heavy chain comprising the amino acid sequence of SEQ ID NO: 444.

In some embodiments, the primary antibody that specifically binds to at least one activatable antibody, conjugated activatable antibody, multispecific activatable antibody, conjugated multispecific activatable antibody, or combination thereof comprises a light chain comprising the amino acid sequence of SEQ ID NO: 445.

In some embodiments, the primary antibody that specifically binds to at least one activatable antibody, conjugated activatable antibody, multispecific activatable antibody, conjugated multispecific activatable antibody, or combination thereof comprises a heavy chain comprising the amino acid sequence of SEQ ID NO: 444, and a light chain comprising the amino acid sequence of SEQ ID NO: 445.

In some embodiments, the primary antibody that specifically binds to at least one activatable antibody, conjugated activatable antibody, multispecific activatable antibody, conjugated multispecific activatable antibody, or combination thereof comprises an amino acid sequence that is at least 90%, 91%, 92%, 93%, 94%, 95%, 96%, 97%, 98%, 99% or more identical to a heavy chain comprising the amino acid sequence of SEQ ID NO: 444.

In some embodiments, the primary antibody that specifically binds to at least one activatable antibody, conjugated activatable antibody, multispecific activatable antibody, conjugated multispecific activatable antibody, or combination thereof comprises an amino acid sequence that is at least 90%, 91%, 92%, 93%, 94%, 95%, 96%, 97%, 98%, 99% or more identical to a light chain comprising the amino acid sequence of SEQ ID NO: 445.

In some embodiments, the primary antibody that specifically binds to at least one activatable antibody, conjugated activatable antibody, multispecific activatable antibody, conjugated multispecific activatable antibody, or combination thereof comprises an amino acid sequence that is at least 90%, 91%, 92%, 93%, 94%, 95%, 96%, 97%, 98%, 99% or more identical to a heavy chain comprising the amino acid sequence of SEQ ID NO: 444, and an amino acid sequence that is at least 90%, 91%, 92%, 93%, 94%, 95%, 96%, 97%, 98%, 99% or more identical to a light chain comprising the amino acid sequence of SEQ ID NO: 445.

In some embodiments, the detectable label is conjugated to the second reagent. In some embodiments, the detectable label is a fluorescent label, such, as for example, HRP, and step v) comprises detecting a level of chemiluminescence in each capillary or population of capillaries.

In some embodiments, the methods provided herein are used to quantitate activation of one or more activatable antibodies in a biological sample. For example, activation may be computed as a percentage on the basis of the sum of activatable antibody and activated activatable antibody species detected. In some embodiments, the methods provided herein are used to compare amounts of activated and intact activatable antibody or activatable antibody-based therapeutics in a biological sample. In some embodiments, the methods provided herein are used to profile, stratify, or otherwise categorize protease activity in vivo in a biological sample. Attributes of the signal peaks resulting from the detection step (i.e., corresponding to the detected signal as a function of molecular weight) can be used as the basis for quantitating the level of first reagent (i.e., detected either directly, or indirectly via detectably labeled secondary or detectably labeled tertiary reagents). For example, peak height or area under the curve and other like methods may be utilized. Typically, step v) comprises quantitating a level of the first reagent in each capillary or population of capillaries comprises comparing the level of first reagent, detected either directly or indirectly, with standard curves for activatable antibody and for activated activatable antibody. Preparation of the standard curves is illustrated in Example 13, hereinbelow.

As described herein, in some embodiments, the activatable antibody-based therapeutic is a conjugated activatable antibody, a multispecific activatable antibody, a conjugated multispecific activatable antibody, or any combination thereof.

In some embodiments, the primary reagent, the secondary reagent, or both the primary reagent and the secondary reagent is an antibody or antigen-binding fragment thereof. In some embodiments, the antibody or antigen-binding fragment thereof that binds a target is a monoclonal antibody, a domain antibody, a single chain antibody, a Fab fragment, a $F(ab')_2$ fragment, a scFv, a scAb, a dAb, a single domain heavy chain antibody, or a single domain light chain antibody. In some embodiments, such an antibody or antigen-binding fragment thereof that binds a target is a mouse, other rodent, chimeric, humanized or fully human monoclonal antibody.

The methods of the present invention can be used to detect and quantify activation of activatable antibodies having any of a variety of structures. The general difference between the structure of the intact activatable antibody structure and the structure of the activated/cleaved activatable antibody structure is a relatively small difference in molecular weight. Detection and quantitation can be achieved from even the most complex biological samples. For example, in some embodiments, the disclosure provides methods for qualitatively and/or quantitatively analyzing activatable antibody therapeutic activation in biological samples, including tissues and/or plasma samples, using a capillary-based immunoassay platform. The methods provided herein are useful with any activatable antibody-based therapeutic including, for example, activatable antibody, conjugated activatable antibody, multispecific activatable antibody, conjugated multispecific activatable antibody, or any combination thereof. Unless otherwise specifically defined, all disclosure regarding suitable activatable antibodies for use in the methods provided herein is also applicable and suitable for other activatable anybody-based therapeutics, including, by way of non-limiting examples, activatable antibodies, conjugated activatable antibodies, multispecific activatable antibodies, conjugated multispecific activatable antibodies, or any combination thereof.

In some embodiments, the disclosure provides methods for qualitatively and/or quantitatively analyzing activation of activatable antibody therapeutics having an antibody or an antigen binding fragment thereof (AB) that specifically binds a target; a masking moiety (MM) coupled to the light chain of the AB such that, when the activatable antibody is in an uncleaved state, inhibits the binding of the AB to the target; and a cleavable moiety (CM) coupled to the AB, wherein the CM is a polypeptide that functions as a substrate for a protease. In some embodiments, the methods are used to quantitate or otherwise compare at least (i) the level of activated activatable antibodies in which the CM has been cleaved and the MM is not coupled to the light chain of the AB; and (ii) the level of intact activatable antibodies in which the MM and the CM are coupled to the light chain of the AB.

In some embodiments, the AB of an activatable antibody and/or conjugated activatable antibody that specifically binds a target is an antibody. In some embodiments, the antibody or antigen-binding fragment thereof that binds a target is a monoclonal antibody, a domain antibody, a single chain antibody, a Fab fragment, a $F(ab')_2$ fragment, a scFv, a scAb, a dAb, a single domain heavy chain antibody, or a single domain light chain antibody. In some embodiments, such an antibody or antigen-binding fragment thereof that binds a target is a mouse, other rodent, chimeric, humanized or fully human monoclonal antibody.

The activatable antibodies in an activated state binds the target and include (i) an antibody or an antigen binding fragment thereof (AB) that specifically binds a target; (ii) a masking moiety (MM) coupled to the AB such that, when the activatable antibody is in an uncleaved state, inhibits the binding of the AB to the target; and (iii) a cleavable moiety (CM) coupled to the AB, wherein the CM is a polypeptide that functions as a substrate for a protease.

In some embodiments, the activatable antibody in the uncleaved state has the structural arrangement from N-terminus to C-terminus as follows: MM-CM-AB or AB-CM-MM.

In some embodiments, the activatable antibody comprises a linking peptide between the MM and the CM.

In some embodiments, the activatable antibody comprises a linking peptide between the CM and the AB.

In some embodiments, the activatable antibody comprises a first linking peptide (LP1) and a second linking peptide (LP2), and wherein the activatable antibody in the uncleaved state has the structural arrangement from N-terminus to C-terminus as follows: MM-LP1-CM-LP2-AB or AB-LP2-CM-LP1-MM. In some embodiments, the two linking peptides need not be identical to each other.

In some embodiments, at least one of LP1 or LP2 comprises an amino acid sequence selected from the group consisting of $(GS)_n$, $(GGS)_n$, $(GSGGS)_n$ (SEQ ID NO: 339) and $(GGGS)_n$ (SEQ ID NO: 340), where n is an integer of at least one, and in some embodiments, not greater than twenty.

In some embodiments, at least one of LP1 or LP2 comprises an amino acid sequence selected from the group consisting of GGSG (SEQ ID NO: 341), GGSGG (SEQ ID NO: 342), GSGSG (SEQ ID NO: 343), GSGGG (SEQ ID NO: 344), GGGSG (SEQ ID NO: 345), GSSSG (SEQ ID NO: 346), and GGGSSGGS (SEQ ID NO: 449).

In some embodiments, LP1 comprises the amino acid sequence GSSGGSGGSGGSG (SEQ ID NO: 347), GSSGGSGGSGG (SEQ ID NO: 348), GSSGGSGGSGGS (SEQ ID NO: 349), GSSGGSGGSGGSGGGS (SEQ ID NO: 350), GSSGGSGGSG (SEQ ID NO: 351), GGGSSGGS (SEQ ID NO: 449), or GSSGGSGGSGS (SEQ ID NO: 352).

In some embodiments, LP2 comprises the amino acid sequence GSS, GGS, GGGS (SEQ ID NO: 353), GSSGT (SEQ ID NO: 354) or GSSG (SEQ ID NO: 355).

In some embodiments, the activatable antibody includes an antibody or antigen-binding fragment thereof (AB) that specifically binds a target. In some embodiments, the antibody or antigen-binding fragment thereof that binds a target is a monoclonal antibody, domain antibody, single chain, Fab fragment, a $F(ab')_2$ fragment, a scFv, a scAb, a dAb, a single domain heavy chain antibody, or a single domain light chain antibody. In some embodiments, such an antibody or antigen-binding fragment thereof that binds a target is a mouse, other rodent, chimeric, humanized or fully human monoclonal antibody.

In some embodiments, the MM has a dissociation constant for binding to the AB which is greater than the dissociation constant of the AB to the target.

In some embodiments, the MM has a dissociation constant for binding to the AB which is no more than the dissociation constant of the AB to the target.

In some embodiments, the MM has a dissociation constant for binding to the AB is equivalent to the dissociation constant of the AB to the target.

In some embodiments, the MM has a dissociation constant for binding to the AB which is less than the dissociation constant of the AB to the target.

In some embodiments, the dissociation constant ($K_d$) of the MM towards the AB is no more than 2, 3, 4, 5, 10, 25, 50, 100, 250, 500, 1,000, 2,500, 5,000, 10,000, 50,000, 100,000, 500,000, 1,000,000, 5,000,000, 10,000,000, 50,000,000 times or greater, or between 1-5, 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times or greater than the dissociation constant of the AB towards the target.

In some embodiments, the MM does not interfere or compete with the AB for binding to the target when the activatable antibody is in a cleaved state.

In some embodiments, the MM is a polypeptide of about 2 to 40 amino acids in length. In some embodiments, the MM is a polypeptide of up to about 40 amino acids in length.

In some embodiments, the MM polypeptide sequence is different from that of the target. In some embodiments, the MM polypeptide sequence is no more than 50% identical to any natural binding partner of the AB. In some embodiments, the MM polypeptide sequence is different from that of the target and is no more than 40%, 30%, 25%, 20%, 15%, or 10% identical to any natural binding partner of the AB.

In some embodiments, the coupling of the MM to the AB reduces the ability of the AB to binds the target such that the dissociation constant ($K_d$) of the AB when coupled to the MM towards the target is at least two times greater than the $K_d$ of the AB when not coupled to the MM towards the target.

In some embodiments, the coupling of the MM to the AB reduces the ability of the AB to binds the target such that the dissociation constant ($K_d$) of the AB when coupled to the MM towards the target is at least five times greater than the $K_d$ of the AB when not coupled to the MM towards the target.

In some embodiments, the coupling of the MM to the AB reduces the ability of the AB to binds the target such that the dissociation constant ($K_d$) of the AB when coupled to the MM towards the target is at least 10 times greater than the $K_d$ of the AB when not coupled to the MM towards the target.

In some embodiments, the coupling of the MM to the AB reduces the ability of the AB to binds the target such that the dissociation constant ($K_d$) of the AB when coupled to the MM towards the target is at least 20 times greater than the $K_d$ of the AB when not coupled to the MM towards the target.

In some embodiments, the coupling of the MM to the AB reduces the ability of the AB to binds the target such that the dissociation constant ($K_d$) of the AB when coupled to the MM towards the target is at least 40 times greater than the $K_d$ of the AB when not coupled to the MM towards the target.

In some embodiments, the coupling of the MM to the AB reduces the ability of the AB to binds the target such that the dissociation constant ($K_d$) of the AB when coupled to the MM towards the target is at least 100 times greater than the $K_d$ of the AB when not coupled to the MM towards the target.

In some embodiments, the coupling of the MM to the AB reduces the ability of the AB to binds the target such that the dissociation constant ($K_d$) of the AB when coupled to the MM towards the target is at least 1000 times greater than the $K_d$ of the AB when not coupled to the MM towards the target.

In some embodiments, the coupling of the MM to the AB reduces the ability of the AB to binds the target such that the dissociation constant ($K_d$) of the AB when coupled to the MM towards the target is at least 10,000 times greater than the $K_d$ of the AB when not coupled to the MM towards the target.

In some embodiments, in the presence of the target, the MM reduces the ability of the AB to binds the target by at least 90% when the CM is uncleaved, as compared to when the CM is cleaved when assayed in vitro using a target displacement assay such as, for example, the assay described in PCT Publication No. WO 2010/081173, the contents of which are hereby incorporated by reference in their entirety.

In some embodiments, the protease that cleaves the CM is active, e.g., up-regulated or otherwise unregulated, in diseased tissue, and the protease cleaves the CM in the activatable antibody when the activatable antibody is exposed to the protease.

In some embodiments, the protease is co-localized with the target in a tissue, and the protease cleaves the CM in the activatable antibody when the activatable antibody is exposed to the protease.

In some embodiments, the CM is positioned in the activatable antibody such that when the activatable antibody is in the uncleaved state, binding of the activatable antibody to the target is reduced to occur with a dissociation constant that is at least twofold greater than the dissociation constant of an unmodified AB binding to the target, whereas in the cleaved state (i.e., when the activatable antibody is in the cleaved state), the AB binds a target.

In some embodiments, the CM is positioned in the activatable antibody such that when the activatable antibody is in the uncleaved state, binding of the activatable antibody to the target is reduced to occur with a dissociation constant that is at least fivefold greater than the dissociation constant of an unmodified AB binding to the target, whereas in the cleaved state (i.e., when the activatable antibody is in the cleaved state), the AB binds a target.

In some embodiments, the CM is positioned in the activatable antibody such that when the activatable antibody is in the uncleaved state, binding of the activatable antibody to the target is reduced to occur with a dissociation constant that is at least 10-fold greater than the dissociation constant of an unmodified AB binding to the target, whereas in the cleaved state (i.e., when the activatable antibody is in the cleaved state), the AB binds a target.

In some embodiments, the CM is positioned in the activatable antibody such that when the activatable antibody is in the uncleaved state, binding of the activatable antibody to the target is reduced to occur with a dissociation constant that is at least 20-fold greater than the dissociation constant of an unmodified AB binding to the target, whereas in the cleaved state (i.e., when the activatable antibody is in the cleaved state), the AB binds a target.

In some embodiments, the CM is positioned in the activatable antibody such that when the activatable antibody is in the uncleaved state, binding of the activatable antibody to the target is reduced to occur with a dissociation constant that is at least 40-fold greater than the dissociation constant of an unmodified AB binding to the target, whereas in the cleaved state, the AB binds a target.

In some embodiments, the CM is positioned in the activatable antibody such that when the activatable antibody is in the uncleaved state, binding of the activatable antibody to the target is reduced to occur with a dissociation constant that is at least 50-fold greater than the dissociation constant of an unmodified AB binding to the target, whereas in the cleaved state, the AB binds a target.

In some embodiments, the CM is positioned in the activatable antibody such that when the activatable antibody is in the uncleaved state, binding of the activatable antibody to the target is reduced to occur with a dissociation constant that is at least 100-fold greater than the dissociation constant of an unmodified AB binding to the target, whereas in the cleaved state, the AB binds a target.

In some embodiments, the CM is positioned in the activatable antibody such that when the activatable antibody is in the uncleaved state, binding of the activatable antibody to the target is reduced to occur with a dissociation constant that is at least 200-fold greater than the dissociation constant of an unmodified AB binding to the target, whereas in the cleaved state, the AB binds a target.

In some embodiments, the CM is a polypeptide of up to 15 amino acids in length.

In some embodiments, the CM is a polypeptide that includes a first cleavable moiety (CM1) that is a substrate for at least one matrix metalloprotease (MMP) and a second cleavable moiety (CM2) that is a substrate for at least one serine protease (SP). In some embodiments, each of the CM1 substrate sequence and the CM2 substrate sequence of the CM1-CM2 substrate is independently a polypeptide of up to 15 amino acids in length.

In some embodiments, the CM is a substrate for at least one protease that is or is believed to be up-regulated or otherwise unregulated in cancer.

In some embodiments, the CM is a substrate for at least one protease selected from the group consisting of a matrix metalloprotease (MMP), thrombin, a neutrophil elastase, a cysteine protease, legumain, and a serine protease, such as matriptase (MT-SP1), and urokinase (uPA). Without being bound by theory, it is believed that these proteases are up-regulated or otherwise unregulated in at least one of cancer.

Exemplary substrates include but are not limited to substrates cleavable by one or more of the following enzymes or proteases listed in Table 4.

In some embodiments, the CM is selected for use with a specific protease, for example a protease that is known to be co-localized with the target of the activatable antibody.

In some embodiments, the CM is a substrate for at least one MMP. Examples of MMPs include the MMPs listed in the Table 4. In some embodiments, the CM is a substrate for a protease selected from the group consisting of MMP 9, MMP14, MMP1, MMP3, MMP13, MMP17, MMP11, and MMP19. In some embodiments the CM is a substrate for MMP9. In some embodiments, the CM is a substrate for MMP14.

In some embodiments, the CM is a substrate that includes the sequence TGRGPSWV (SEQ ID NO: 356); SARGPSRW (SEQ ID NO: 357); TARGPSFK (SEQ ID NO: 358); LSGRSDNH (SEQ ID NO: 359); GGWHTGRN (SEQ ID NO: 360); HTGRSGAL (SEQ ID NO: 361); PLTGRSGG (SEQ ID NO: 362); AARGPAIH (SEQ ID NO: 363); RGPAFNPM (SEQ ID NO: 364); SSRGPAYL (SEQ ID NO: 365); RGPATPIM (SEQ ID NO: 366); RGPA (SEQ ID NO: 367); GGQPSGMWGW (SEQ ID NO: 368); FPRPLGITGL (SEQ ID NO: 369); VHMPLGFLGP (SEQ ID NO: 370); SPLTGRSG (SEQ ID NO: 371); SAGFSLPA (SEQ ID NO: 372); LAPLGLQRR (SEQ ID NO: 373); SGGPLGVR (SEQ ID NO: 374); PLGL (SEQ ID NO: 375); LSGRSGNH (SEQ ID NO: 789); SGRSANPRG (SEQ ID NO: 790); LSGRSDDH (SEQ ID NO: 791); LSGRSDIH (SEQ ID NO: 792); LSGRSDQH (SEQ ID NO: 793); LSGRSDTH (SEQ ID NO: 794); LSGRSDYH (SEQ ID NO: 795); LSGRSDNP (SEQ ID NO: 796); LSGRSANP (SEQ ID NO: 797); LSGRSANI (SEQ ID NO: 798); LSGRSDNI (SEQ ID NO: 799); MIAPVAYR (SEQ ID NO: 800); RPSPMWAY (SEQ ID NO: 801); WATPRPMR (SEQ ID NO: 802); FRLLDWQW (SEQ ID NO: 803); ISSGL (SEQ ID NO: 804); ISSGLLS (SEQ ID NO: 805); and/or ISSGLL (SEQ ID NO: 806).

In some embodiments, the CM comprises the amino acid sequence LSGRSDNH (SEQ ID NO: 359). In some embodiments, the CM comprises the amino acid sequence TGRGPSWV (SEQ ID NO: 356). In some embodiments, the CM comprises the amino acid sequence PLTGRSGG (SEQ ID NO: 362). In some embodiments, the CM comprises the amino acid sequence GGQPSGMWGW (SEQ ID NO: 368). In some embodiments, the CM comprises the amino acid sequence FPRPLGITGL (SEQ ID NO: 369). In some embodiments, the CM comprises the amino acid sequence VHMPLGFLGP (SEQ ID NO: 370). In some embodiments, the CM comprises the amino acid sequence PLGL (SEQ ID NO: 375). In some embodiments, the CM comprises the amino acid sequence SARGPSRW (SEQ ID NO: 357). In some embodiments, the CM comprises the amino acid sequence TARGPSFK (SEQ ID NO: 358). In some embodiments, the CM comprises the amino acid sequence GGWHTGRN (SEQ ID NO: 360). In some embodiments, the CM comprises the amino acid sequence HTGRSGAL (SEQ ID NO: 361). In some embodiments, the CM comprises the amino acid sequence AARGPAIH (SEQ ID NO: 363). In some embodiments, the CM comprises the amino acid sequence RGPAFNPM (SEQ ID NO: 364). In some embodiments, the CM comprises the amino acid sequence SSRGPAYL (SEQ ID NO: 365). In some embodiments, the CM comprises the amino acid sequence RGPATPIM (SEQ ID NO: 366). In some embodiments, the CM comprises the amino acid sequence RGPA (SEQ ID NO: 367). In some embodiments, the CM comprises the amino acid sequence LSGRSGNH (SEQ ID NO: 789). In some embodiments, the CM comprises the amino acid sequence SGRSANPRG (SEQ ID NO: 790). In some embodiments, the CM comprises the amino acid sequence LSGRSDDH (SEQ ID NO: 791). In some embodiments, the CM comprises the amino acid sequence LSGRSDIH (SEQ ID NO: 792). In some embodiments, the CM comprises the amino acid sequence LSGRSDQH (SEQ ID NO: 793). In some embodiments, the CM comprises the amino acid sequence LSGRSDTH (SEQ ID NO: 794). In some embodiments, the CM comprises the amino acid sequence LSGRSDYH (SEQ ID NO: 795). In some embodiments, the CM comprises the amino acid sequence LSGRSDNP (SEQ ID NO: 796). In some embodiments, the CM comprises the amino acid sequence LSGRSANP (SEQ ID NO: 797). In some embodiments, the CM comprises the amino acid sequence LSGRSANI (SEQ ID NO: 798). In some embodiments, the CM comprises the amino acid sequence LSGRSDNI (SEQ ID NO: 799). In some embodiments, the CM comprises the amino acid sequence MIAPVAYR (SEQ ID NO: 800). In some embodiments, the CM comprises the amino acid sequence RPSPMWAY (SEQ ID NO: 801). In some embodiments, the CM comprises the amino acid sequence WATPRPMR (SEQ ID NO: 802). In some embodiments, the CM comprises the amino acid sequence FRLLDWQW (SEQ ID NO: 803). In some embodiments, the CM comprises the amino acid sequence ISSGL (SEQ ID NO: 804). In some embodiments, the CM comprises the amino acid sequence ISSGLLS (SEQ ID NO: 805). In some embodiments, the CM comprises the amino acid sequence and/or ISSGLL (SEQ ID NO: 806).

In some embodiments, the CM is a substrate for an MMP and includes the sequence ISSGLSS (SEQ ID NO: 376); QNQALRMA (SEQ ID NO: 377); AQNLLGMV (SEQ ID NO: 378); STFPFGMF (SEQ ID NO: 379); PVGYTSSL (SEQ ID NO: 380); DWLYWPGI (SEQ ID NO: 381), ISSGLLSS (SEQ ID NO: 382), LKAAPRWA (SEQ ID NO: 383); GPSHLVLT (SEQ ID NO: 384); LPGGLSPW (SEQ ID NO: 385); MGLFSEAG (SEQ ID NO: 386); SPLPLRVP (SEQ ID NO: 387); RMHLRSLG (SEQ ID NO: 388); LAAPLGLL (SEQ ID NO: 389); AVGLLAPP (SEQ ID NO: 390); LLAPSHRA (SEQ ID NO: 391); and/or PAGLWLDP (SEQ ID NO: 392).

In some embodiments, the CM comprises the amino acid sequence ISSGLSS (SEQ ID NO: 376). In some embodiments, the CM comprises the amino acid sequence QNQALRMA (SEQ ID NO: 377). In some embodiments, the CM comprises the amino acid sequence AQNLLGMV (SEQ ID NO: 378). In some embodiments, the CM comprises the amino acid sequence STFPFGMF (SEQ ID NO: 379). In some embodiments, the CM comprises the amino acid sequence PVGYTSSL (SEQ ID NO: 380). In some embodiments, the CM comprises the amino acid sequence DWLYWPGI (SEQ ID NO: 381). In some embodiments, the CM comprises the amino acid sequence ISSGLLSS (SEQ ID NO: 382). In some embodiments, the CM comprises the amino acid sequence LKAAPRWA (SEQ ID NO: 383). In some embodiments, the CM comprises the amino acid sequence GPSHLVLT (SEQ ID NO: 384). In some embodiments, the CM comprises the amino acid sequence LPGGLSPW (SEQ ID NO: 385). In some embodiments, the CM comprises the amino acid sequence MGLFSEAG (SEQ ID NO: 386). In some embodiments, the CM comprises the amino acid sequence SPLPLRVP (SEQ ID NO: 387). In some embodiments, the CM comprises the amino acid sequence RMHLRSLG (SEQ ID NO: 388). In some embodiments, the CM comprises the amino acid sequence LAAPLGLL (SEQ ID NO: 389). In some embodiments, the CM comprises the amino acid sequence AVGLLAPP (SEQ ID NO: 390). In some embodiments, the CM comprises the amino acid sequence LLAPSHRA (SEQ ID NO: 391). In some embodiments, the CM comprises the amino acid sequence PAGLWLDP (SEQ ID NO: 392).

In some embodiments, the CM is a substrate for thrombin. In some embodiments, the CM is a substrate for thrombin and includes the sequence GPRSFGL (SEQ ID NO: 393) or GPRSFG (SEQ ID NO: 394). In some embodiments, the CM comprises the amino acid sequence GPRSFGL (SEQ ID NO: 393). In some embodiments, the CM comprises the amino acid sequence GPRSFG (SEQ ID NO: 394).

In some embodiments, the CM comprises an amino acid sequence selected from the group consisting of NTLSGRSENHSG (SEQ ID NO: 395); NTLSGRSGNHGS (SEQ ID NO: 396); TSTSGRSANPRG (SEQ ID NO: 397); TSGRSANP (SEQ ID NO: 398); VAGRSMRP (SEQ ID NO: 399); VVPEGRRS (SEQ ID NO: 400); ILPRSPAF (SEQ ID NO: 401); MVLGRSLL (SEQ ID NO: 402); QGRAITFI (SEQ ID NO: 403); SPRSIMLA (SEQ ID NO: 404); and SMLRSMPL (SEQ ID NO: 405).

In some embodiments, the CM comprises the amino acid sequence NTLSGRSENHSG (SEQ ID NO: 395). In some embodiments, the CM comprises the amino acid sequence NTLSGRSGNHGS (SEQ ID NO: 396). In some embodiments, the CM comprises the amino acid sequence TSTSGRSANPRG (SEQ ID NO: 397). In some embodiments, the CM comprises the amino acid sequence TSGRSANP (SEQ ID NO: 398). In some embodiments, the CM comprises the amino acid sequence VAGRSMRP (SEQ ID NO: 399). In some embodiments, the CM comprises the amino acid sequence VVPEGRRS (SEQ ID NO: 400). In some embodiments, the CM comprises the amino acid sequence ILPRSPAF (SEQ ID NO: 401). In some embodiments, the CM comprises the amino acid sequence MVLGRSLL (SEQ ID NO: 402). In some embodiments, the CM comprises the amino acid sequence QGRAITFI (SEQ ID NO: 403). In some embodiments, the CM comprises the amino acid sequence SPRSIMLA (SEQ ID NO: 404). In some embodiments, the CM comprises the amino acid sequence SMLRSMPL (SEQ ID NO: 405).

In some embodiments, the CM is a substrate for a neutrophil elastase. In some embodiments, the CM is a substrate for a serine protease. In some embodiments, the CM is a substrate for uPA. In some embodiments, the CM is a substrate for legumain. In some embodiments, the CM is a substrate for matriptase. In some embodiments, the CM is a substrate for a cysteine protease. In some embodiments, the CM is a substrate for a cysteine protease, such as a cathepsin.

In some embodiments, the CM is a CM1-CM2 substrate and includes the sequence ISSGLLSGRSDNH (SEQ ID NO: 406); ISSGLLSSGGSGGSLSGRSDNH (SEQ ID NO: 407); AVGLLAPPGGTSTSGRSANPRG (SEQ ID NO: 408); TSTSGRSANPRGGGAVGLLAPP (SEQ ID NO: 409); VHMPLGFLGPGGTSTSGRSANPRG (SEQ ID NO: 410); TSTSGRSANPRGGGVHMPLGFLGP (SEQ ID NO: 411); AVGLLAPPGGLSGRSDNH (SEQ ID NO: 412); LSGRSDNHGGAVGLLAPP (SEQ ID NO: 413); VHMPLGFLGPGGLSGRSDNH (SEQ ID NO: 414); LSGRSDNHGGVHMPLGFLGP (SEQ ID NO: 415); LSGRSDNHGGSGGSISSGLLSS (SEQ ID NO: 416); LSGRSGNHGGSGGSISSGLLSS (SEQ ID NO: 417); ISSGLLSSGGSGGSLSGRSGNH (SEQ ID NO: 418); LSGRSDNHGGSGGSQNQALRMA (SEQ ID NO: 419); QNQALRMAGGSGGSLSGRSDNH (SEQ ID NO: 420); LSGRSGNHGGSGGSQNQALRMA (SEQ ID NO: 421); QNQALRMAGGSGGSLSGRSGNH (SEQ ID NO: 422); ISSGLLSGRSGNH (SEQ ID NO: 423); ISSGLLSGRSANPRG (SEQ ID NO: 680); AVGLLAPPTSGRSANPRG (SEQ ID NO: 681); AVGLLAPPSGRSANPRG (SEQ ID NO: 682); ISSGLLSGRSDDH (SEQ ID NO: 683); ISSGLLSGRSDIH (SEQ ID NO: 684); ISSGLLSGRSDQH (SEQ ID NO: 685); ISSGLLSGRSDTH (SEQ ID NO: 686); ISSGLLSGRSDYH (SEQ ID NO: 687); ISSGLLSGRSDNP (SEQ ID NO: 688); ISSGLLSGRSANP (SEQ ID NO: 689); ISSGLLSGRSANI (SEQ ID NO: 690); AVGLLAPPGGLSGRSDDH (SEQ ID NO: 691); AVGLLAPPGGLSGRSDIH (SEQ ID NO: 692); AVGLLAPPGGLSGRSDQH (SEQ ID NO: 693); AVGLLAPPGGLSGRSDTH (SEQ ID NO: 694); AVGLLAPPGGLSGRSDYH (SEQ ID NO: 695); AVGLLAPPGGLSGRSDNP (SEQ ID NO: 696); AVGLLAPPGGLSGRSANP (SEQ ID NO: 697); AVGLLAPPGGLSGRSANI (SEQ ID NO: 698), ISSGLLSGRSDNI (SEQ ID NO: 713); AVGLLAPPGGLSGRSDNI (SEQ ID NO: 714); GLSGRSDNHGGAVGLLAPP (SEQ ID NO: 807); and/or GLSGRSDNHGGVHMPLGFLGP (SEQ ID NO: 808).

In some embodiments, the CM1-CM2 substrate includes the sequence ISSGLLSGRSDNH (SEQ ID NO: 406), which is also referred to herein as substrate 2001. In some embodiments, the CM1-CM2 substrate includes the sequence ISSGLLSSGGSGGSLSGRSDNH (SEQ ID NO: 407), which is also referred to herein as substrate 1001/LP'/0001, where LP' as used in this CM1-CM2 substrate is the amino acid sequence GGSGGS (SEQ ID NO: 1037). In some embodiments, the CM1-CM2 substrate includes the sequence AVGLLAPPGGTSTSGRSANPRG (SEQ ID NO: 408), which is also referred to herein as substrate 2015 and/or substrate 1004/LP'/0003, where LP' as used in this CM1-CM2 substrate is the amino acid sequence GG. In some embodiments, the CM1-CM2 substrate includes the sequence TSTSGRSANPRGGGAVGLLAPP (SEQ ID NO: 409), which is also referred to herein as substrate 0003/LP'/1004, where LP' as used in this CM1-CM2 substrate is the amino acid sequence GG. In some embodiments, the CM1-CM2 substrate includes the sequence VHMPLGFLGPGGTSTSGRSANPRG (SEQ ID NO: 410), which is also referred to herein as substrate 1003/LP'/0003, where LP' as used in this CM1-CM2 substrate is the amino acid sequence GG. In some embodiments, the CM1-CM2 substrate includes the sequence TSTSGRSANPRGGGVHMPLGFLGP (SEQ ID NO: 411), which is also referred to herein as substrate 0003/LP'/1003, where LP' as used in this CM1-CM2 substrate is the amino acid sequence GG. In some embodiments, the CM1-CM2 substrate includes the sequence AVGLLAPPGGLSGRSDNH (SEQ ID NO: 412), which is also referred to herein as substrate 3001 and/or substrate 1004/LP'/0001, where LP' as used in this CM1-CM2 substrate is the amino acid sequence GG. In some embodiments, the CM1-CM2 substrate includes the sequence LSGRSDNHGGAVGLLAPP (SEQ ID NO: 413), which is also referred to herein as substrate 0001/LP'/1004, where LP' as used in this CM1-CM2 substrate is the amino acid sequence GG. In some embodiments, the CM1-CM2 substrate includes the sequence VHMPLGFLGPGGLSGRSDNH (SEQ ID NO: 414), which is also referred to herein as substrate 1003/LP'/0001, wherein LP' as used in this CM1-CM2 substrate is the amino acid sequence GG. In some embodiments, the CM1-CM2 substrate includes the sequence LSGRSDNHGGVHMPLGFLGP (SEQ ID NO: 415), which is also referred to herein as substrate 0001/LP'/1003, where LP' as used in this CM1-CM2 substrate is the amino acid sequence GG. In some embodiments, the CM1-CM2 substrate includes the sequence LSGRSDNHGGSGGSISSGLLSS (SEQ ID NO: 416), which is also referred to herein as substrate 0001/LP'/1001, where LP' as used in this CM1-CM2 substrate is the amino acid sequence GGSGGS (SEQ ID NO: 1037). In some embodiments, the CM1-CM2 substrate includes the sequence LSGRSGNHGGSGGSISSGLLSS (SEQ ID NO: 417), which is also referred to herein as substrate 0002/LP'/1001, where LP' as used in this CM1-CM2 substrate is the amino acid sequence GGSGGS (SEQ ID NO: 1037). In some embodiments, the CM1-CM2 substrate includes the sequence ISSGLLSSGGSGGSLSGRSGNH (SEQ ID NO: 418), which is also referred to herein as substrate 1001/LP'/0002, where LP' as used in this CM1-CM2 substrate is the amino acid sequence GGSGGS (SEQ ID NO: 1037). In some embodiments, the CM1-CM2 substrate includes the sequence LSGRSDNHGGSGGSQNQALRMA (SEQ ID NO: 419), which is also referred to herein as substrate 0001/LP'/1002, where LP' as used in this CM1-CM2 substrate is the amino acid sequence GGSGGS (SEQ ID NO: 1037). In some embodiments, the CM1-CM2 substrate includes the sequence QNQALRMAGGSGGSLSGRSDNH (SEQ ID NO: 420), which is also referred to herein as substrate 1002/LP'/0001, where LP' as used in this CM1-CM2 substrate is the amino acid sequence GGSGGS (SEQ ID NO: 1037). In some embodiments, the CM1-CM2 substrate includes the sequence LSGRSGNHGGSGGSQNQALRMA (SEQ ID NO: 421), which is also referred to herein as substrate 0002/LP'/1002, where LP' as used in this CM1-CM2 substrate is the amino acid sequence GGSGGS (SEQ ID NO: 1037). In some embodiments, the CM1-CM2 substrate includes the sequence QNQALRMAGGSGGSLSGRSGNH (SEQ ID NO: 422), which is also referred to herein as substrate 1002/LP'/0002, where LP' as used in this CM1-CM2 substrate is the amino acid sequence GGSGGS (SEQ ID NO: 1037). In some embodiments, the CM1-CM2 substrate includes the sequence ISSGLLSGRSGNH (SEQ ID NO: 423), which is also referred to herein as substrate 2002. In some embodiments, the CM1-CM2 substrate includes the sequence ISSGLLSGRSANPRG (SEQ ID NO: 680), which is also referred to herein as substrate 2003. In some embodiments, the CM1-CM2 substrate includes the sequence AVGLLAPPTSGRSANPRG (SEQ ID NO: 681), which is also referred to herein as substrate 2004. In some embodiments, the CM1-CM2 substrate includes the sequence AVGLLAPPSGRSANPRG (SEQ ID NO: 682), which is also referred to herein as substrate 2005. In some embodiments, the CM1-CM2 substrate includes the sequence ISSGLLSGRSDDH (SEQ ID NO: 683), which is also referred to herein as substrate 2006. In some embodiments, the CM1-CM2 substrate includes the sequence ISSGLLSGRSDIH (SEQ ID NO: 684), which is also referred to herein as substrate 2007. In some embodiments, the CM1-CM2 substrate includes the sequence ISSGLLSGRSDQH (SEQ ID NO: 685), which is also referred to herein as substrate 2008. In some embodiments, the CM1-CM2 substrate includes the sequence ISSGLLSGRSDTH (SEQ ID NO: 686), which is also referred to herein as substrate 2009. In some embodiments, the CM1-CM2 substrate includes the sequence ISSGLLSGRSDYH (SEQ ID NO: 687), which is also referred to herein as substrate 2010. In some embodiments, the CM1-CM2 substrate includes the sequence ISSGLLSGRSDNP (SEQ ID NO: 688), which is also referred to herein as substrate 2011. In some embodiments, the CM1-CM2 substrate includes the sequence ISSGLLSGRSANP (SEQ ID NO: 689), which is also referred to herein as substrate 2012. In some embodiments, the CM1-CM2 substrate includes the sequence ISSGLLSGRSANI (SEQ ID NO: 690), which is also referred to herein as substrate 2013. In some embodiments, the CM1-CM2 substrate includes the sequence AVGLLAPPGGLSGRSDDH (SEQ ID NO: 691), which is also referred to herein as substrate 3006. In some embodiments, the CM1-CM2 substrate includes the sequence AVGLLAPPGGLSGRSDIH (SEQ ID NO: 692), which is also referred to herein as substrate 3007. In some embodiments, the CM1-CM2 substrate includes the sequence AVGLLAPPGGLSGRSDQH (SEQ ID NO: 693), which is also referred to herein as substrate 3008. In some embodiments, the CM1-CM2 substrate includes the sequence AVGLLAPPGGLSGRSDTH (SEQ ID NO: 694), which is also referred to herein as substrate 3009. In some embodiments, the CM1-CM2 substrate includes the sequence AVGLLAPPGGLSGRSDYH (SEQ ID NO: 695), which is also referred to herein as substrate 3010. In some embodiments, the CM1-CM2 substrate includes the sequence AVGLLAPPGGLSGRSDNP (SEQ ID NO: 696), which is also referred to herein as substrate 3011. In some embodiments, the CM1-CM2 substrate includes the sequence AVGLLAPPGGLSGRSANP (SEQ ID NO: 697), which is also referred to herein as substrate 3012. In some embodiments, the CM1-CM2 substrate includes the sequence AVGLLAPPGGLSGRSANI (SEQ ID NO: 698), which is also referred to herein as substrate 3013. In some embodiments, the CM1-CM2 substrate includes the sequence ISSGLLSGRSDNI (SEQ ID NO: 713), which is also referred to herein as substrate 2014. In some embodiments, the CM1-CM2 substrate includes the sequence AVGLLAPPGGLSGRSDNI (SEQ ID NO: 714), which is also referred to herein as substrate 3014. In some embodiments, the CM1-CM2 substrate includes the sequence GLSGRSDNHGGAVGLLAPP (SEQ ID NO: 807), which is also referred to herein as substrate 0001/LP'/1004, where LP' as used in this CM1-CM2 substrate is the amino acid sequence GG. In some embodiments, the CM1-CM2 substrate includes the sequence GLS- GRSDNHGGVHMPLGFLGP (SEQ ID NO: 808), which is also referred to herein as substrate 0001/LP'/1003, where LP' as used in this CM1-CM2 substrate is the amino acid sequence GG.

In some embodiments, the CM is a substrate for at least two proteases. In some embodiments, each protease is selected from the group consisting of those shown in Table 4. In some embodiments, the CM is a substrate for at least two proteases, wherein one of the proteases is selected from the group consisting of a MMP, thrombin, a neutrophil elastase, a cysteine protease, uPA, legumain and matriptase and the other protease is selected from the group consisting of those shown in Table 4. In some embodiments, the CM is a substrate for at least two proteases selected from the group consisting of a MMP, thrombin, a neutrophil elastase, a cysteine protease, uPA, legumain and matriptase.

In some embodiments, the activatable antibody includes at least a first CM and a second CM. In some embodiments, the first CM and the second CM are each polypeptides of no more than 15 amino acids long. In some embodiments, the first CM and the second CM in the activatable antibody in the uncleaved state have the structural arrangement from N-terminus to C-terminus as follows: MM-CM1-CM2-AB or AB-CM2-CM1-MM. In some embodiments, at least one of the first CM and the second CM is a polypeptide that functions as a substrate for a protease selected from the group consisting of a MMP, thrombin, a neutrophil elastase, a cysteine protease, uPA, legumain, and matriptase. In some embodiments, the first CM is cleaved by a first cleaving agent selected from the group consisting of a MMP, thrombin, a neutrophil elastase, a cysteine protease, uPA, legumain, and matriptase in a target tissue and the second CM is cleaved by a second cleaving agent in a target tissue. In some embodiments, the other protease is selected from the group consisting of those shown in Table 4. In some embodiments, the first cleaving agent and the second cleaving agent are the same protease selected from the group consisting of a MMP, thrombin, a neutrophil elastase, a cysteine protease, uPA, legumain, and matriptase, and the first CM and the second CM are different substrates for the enzyme. In some embodiments, the first cleaving agent and the second cleaving agent are the same protease selected from the group consisting of those shown in Table 4. In some embodiments, the first cleaving agent and the second cleaving agent are different proteases. In some embodiments, the first cleaving agent and the second cleaving agent are co-localized in the target tissue. In some embodiments, the first CM and the second CM are cleaved by at least one cleaving agent in the target tissue.

In some embodiments, the activatable antibody is exposed to and cleaved by a protease such that, in the activated or cleaved state, the activated antibody includes a light chain amino acid sequence that includes at least a portion of LP2 and/or CM sequence after the protease has cleaved the CM.

In some embodiments, the activatable antibody is conjugated to one or more agents.

In some embodiments, the agent is a toxin or fragment thereof. In some embodiments, the agent is a microtubule inhibitor. In some embodiments, the agent is a nucleic acid damaging agent. In some embodiments, the agent is selected from the group consisting of a dolastatin or a derivative thereof, an auristatin or a derivative thereof, a maytansinoid or a derivative thereof, a duocarmycin or a derivative thereof, a calicheamicin or a derivative thereof, and a pyrrolobenzodiazepine or a derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid selected from the group consisting of DM1 and DM4. In some embodiments, the agent is maytansinoid DM4. In some embodiments, the agent is duocarmycin. In some embodiments, the agent is conjugated to the AB via a linker. In some embodiments, the linker with which the agent is conjugated to the AB comprises an SPDB moiety, a vc moiety, or a PEG2-vc moiety. In some embodiments, the linker and toxin conjugated to the AB comprises an SPDB-DM4 moiety, a vc-MMAD moiety, a vc-MMAE moiety, vc-duocarmycin, or a PEG2-vc-MMAD moiety. In some embodiments, the linker is a cleavable linker. In some embodiments, the linker is a non-cleavable linker. In some embodiments, the agent is a detectable moiety. In some embodiments, the detectable moiety is a diagnostic agent.

In some embodiments, the agent conjugated to the AB or the AB of an activatable antibody is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one CM1-CM2 substrate sequence. In some embodiments, the agent is conjugated to the AB via a noncleavable linker. In some embodiments, the agent is conjugated to the AB via a linker that is cleavable in an intracellular or lysosomal environment. In some embodiments, the agent is a microtubule inhibitor. In some embodiments, the agent is a nucleic acid damaging agent, such as a DNA alkylator, a DNA cleaving agent, a DNA cross-linker, a DNA intercalator, or other DNA damaging agent. In some embodiments, the agent is an agent selected from the group listed in Table 5. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the activatable antibody is conjugated to one or more equivalents of an agent. In some embodiments, the activatable antibody is conjugated to one equivalent of the agent. In some embodiments, the activatable antibody is conjugated to two, three, four, five, six, seven, eight, nine, ten, or greater than ten equivalents of the agent. In some embodiments, the activatable antibody is part of a mixture of activatable antibodies having a homogeneous number of equivalents of conjugated agents. In some embodiments, the activatable antibody is part of a mixture of activatable antibodies having a heterogeneous number of equivalents of conjugated agents. In some embodiments, the mixture of activatable antibodies is such that the average number of agents conjugated to each activatable antibody is between zero to one, between one to two, between two and three, between three and four, between four and five, between five and six, between six and seven, between seven and eight, between eight and nine, between nine and ten, and ten and greater. In some embodiments, the mixture of activatable antibodies is such that the average number of agents conjugated to each activatable antibody is one, two, three, four, five, six, seven, eight, nine, ten, or greater.

In some embodiments, the activatable antibody comprises one or more site-specific amino acid sequence modifications such that the number of lysine and/or cysteine residues is increased or decreased with respect to the original amino acid sequence of the activatable antibody, thus in some embodiments correspondingly increasing or decreasing the number of agents that can be conjugated to the activatable antibody, or in some embodiments limiting the conjugation of the agents to the activatable antibody in a site-specific manner. In some embodiments, the modified activatable antibody is modified with one or more non-natural amino acids in a site-specific manner, thus in some embodiments limiting the conjugation of the agents to only the sites of the non-natural amino acids.

In some embodiments, the agent is an anti-inflammatory agent.

In some embodiments, the activatable antibody also includes a detectable moiety. In some embodiments, the detectable moiety is a diagnostic agent.

In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or (3-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments of these methods, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM-AB. An example of a spacer joined directly to the N-terminus of MM of the activatable antibody is QGQSGQ (SEQ ID NO: 424). Other examples of a spacer joined directly to the N-terminus of MM of the activatable antibody include QGQSGQG (SEQ ID NO: 645), QGQSG (SEQ ID NO: 646), QGQS (SEQ ID NO: 647), QGQ (SEQ ID NO: 648), QG (SEQ ID NO: 649), and Q. Other examples of a spacer joined directly to the N-terminus of MM of the activatable antibody include GQSGQG (SEQ ID NO: 666), QSGQG (SEQ ID NO: 667), SGQG (SEQ ID NO: 668), GQG (SEQ ID NO: 669), and G. In some embodiments, no spacer is joined to the N-terminus of the MM. In some embodiments, the spacer includes at least the amino acid sequence QGQSGQ (SEQ ID NO: 424). In some embodiments, the spacer includes at least the amino acid sequence QGQSGQG (SEQ ID NO: 645). In some embodiments, the spacer includes at least the amino acid sequence QGQSG (SEQ ID NO: 646). In some embodiments, the spacer includes at least the amino acid sequence QGQS (SEQ ID NO: 647). In some embodiments, the spacer includes at least the amino acid sequence QGQ (SEQ ID NO: 648). In some embodiments, the spacer includes at least the amino acid sequence QG (SEQ ID NO: 649). In some embodiments, the spacer includes at least the amino acid residue Q. In some embodiments, the spacer includes at least the amino acid sequence GQSGQG (SEQ ID NO: 666). In some embodiments, the spacer includes at least the amino acid sequence QSGQG (SEQ ID NO: 667). In some embodiments, the spacer includes at least the amino acid sequence SGQG (SEQ ID NO: 668). In some embodiments, the spacer includes at least the amino acid sequence GQG (SEQ ID NO: 669). In some embodiments, the spacer includes at least the amino acid sequence G. In some embodiments, the spacer is absent.

In some embodiments, the activatable antibody and/or conjugated activatable antibody is monospecific. In some embodiments, the activatable antibody and/or conjugated activatable antibody is multispecific, e.g., by way of non-limiting example, bispecific or trifunctional. In some embodiments, the activatable antibody and/or conjugated activatable antibody is formulated as part of a pro-Bispecific T Cell Engager (BITE) molecule. In some embodiments, the activatable antibody and/or conjugated activatable antibody is formulated as part of a pro-Chimeric Antigen Receptor (CAR) modified T cell or other engineered receptor.

In some embodiments, the activatable antibody or antigen-binding fragment thereof is incorporated in a multispecific activatable antibody or antigen-binding fragment thereof, where at least one arm of the multispecific activatable antibody specifically binds a target. In some embodiments, the activatable antibody or antigen-binding fragment thereof is incorporated in a bispecific antibody or antigen-binding fragment thereof, where at least one arm of the bispecific activatable antibody specifically binds a target.

In some embodiments, the activatable antibody is a multispecific activatable antibody and/or a conjugated multispecific activatable antibody. The multispecific activatable antibodies and/or conjugated multispecific activatable antibodies include at least (i) a first antibody or antigen-binding fragment thereof (AB1) that specifically binds a first target coupled to a first masking moiety (MM1), such that coupling of the MM1 reduces the ability of the AB1 to bind the first target, and (ii) a second antibody or antigen-binding fragment thereof (AB2) that specifically binds a second target coupled to a second masking moiety (MM2), such that coupling of the MM2 reduces the ability of the AB2 to bind the second target. In some embodiments, the MM1 and/or MM2 is coupled to the respective antibody or antigen-binding fragment thereof (AB1 or AB2) via a sequence that includes a substrate for a protease, for example, a protease that is co-localized with the first target, the second target, or both the first target and the second target at a treatment site in a subject. In some embodiments, the first target, the second target, or both the first target and the second target is a mammalian target, such as for example, a human target. Suitable MM1, MM2, CM1, and/or CM2 include any of the MM and/or CM described above in connection with the activatable antibodies and/or conjugated activatable antibodies used in the compositions and methods of the disclosure.

As a non-limiting example, the AB of an activatable antibody is a binding partner for any target listed in Table 1. As a non-limiting example, AB1, AB2, or both AB1 and AB2 of a multispecific activatable antibody is a binding partner for any target listed in Table 1.

TABLE 1

| Exemplary Targets | | | | | |
|---|---|---|---|---|---|
| 1-92-LFA-3 | CD52 | DL44 | HVEM | LIF-R | STEAP1 |
| Alpha-4 integrin | CD56 | DLK1 | Hyaluronidase | Lewis X | STEAP2 |
| Alpha-V integrin | CD64 | DLL4 | ICOS | LIGHT | TAG-72 |
| alpha4beta1 integrin | CD70 | DPP-4 | IFNalpha | LRP4 | TAPA1 |
| alpha4beta7 integrin | the target | DSG1 | IFNbeta | LRRC26 | TGFbeta |
| AGR2 | CD74 | EGFR | IFNgamma | MCSP | TIGIT |
| Anti-Lewis-Y | | EGFRviii | IgE | Mesothelin | TIM-3 |
| Apelin J receptor | CD80 | Endothelin B receptor (ETBR) | IgE Receptor (FceRI) | MRP4 | TLR2 |
| APRIL | CD81 | ENPP3 | IGF | MUC1 | TLR4 |
| B7-H4 | CD86 | EpCAM | IGF1R | Mucin-16 (MUC16, CA-125) | TLR6 |
| BAFF | CD95 | EPHA2 | IL1B | Na/K ATPase | TLR7 |
| BTLA | CD117 | EPHB2 | IL1R | Neutrophil elastase | TLR8 |
| C5 complement | CD125 | ERBB3 | IL2 | NGF | TLR9 |
| C-242 | CD132 (IL-2RG) | F protein of RSV | IL11 | Nicastrin | TMEM31 |
| CA9 | CD133 | FAP | IL12 | Notch Receptors | TNFalpha |
| CA19-9 (Lewis a) | CD137 | FGF-2 | IL12p40 | Notch 1 | TNFR |
| Carbonic anhydrase 9 | CD138 | FGF8 | IL-12R, IL-12Rbeta1 | Notch 2 | TNFRS12 A |
| CD2 | CD166 | FGFR1 | IL13 | Notch 3 | TRAIL-R1 |
| CD3 | CD172A | FGFR2 | IL13R | Notch 4 | TRAIL-R2 |
| CD6 | CD248 | FGFR3 | IL15 | NOV | Transferrin |
| CD9 | CDH6 | FGFR4 | IL17 | OSM-R | Transferrin receptor |
| CD11a | CEACAM5 (CEA) | Folate receptor | IL18 | OX-40 | TRK-A |
| CD19 | CEACAM6 (NCA-90) | GAL3ST1 | IL21 | PAR2 | TRK-B |
| CD20 | CLAUDIN-3 | G-CSF | IL23 | PDGF-AA | uPAR |
| CD22 | CLAUDIN-4 | G-CSFR | IL23R | PDGF-BB | VAP1 |
| CD24 | cMet | GD2 | IL27/IL27R (wsx1) | PDGFRalpha | VCAM-1 |
| CD25 | Collagen | GITR | IL29 | PDGFRbeta | VEGF |
| CD27 | Cripto | GLUT1 | IL-31R | PD-1 | VEGF-A |
| CD28 | CSFR | GLUT4 | IL31/IL31R | PD-L1 | VEGF-B |
| CD30 | CSFR-1 | GM-CSF | IL2R | PD-L2 | VEGF-C |
| CD33 | CTLA-4 | GM-CSFR | IL4 | Phosphatidyl-serine | VEGF-D |
| CD38 | CTGF | GP IIb/IIIa receptors | IL4R | P1GF | VEGFR1 |
| CD40 | CXCL10 | Gp130 | IL6, IL6R | PSCA | VEGFR2 |
| CD40L | CXCL13 | GPIIB/IIIA | Insulin Receptor | PSMA | VEGFR3 |
| CD41 | CXCR1 | GPNMB | Jagged Ligands | RAAG12 | VISTA |
| CD44 | CXCR2 | GRP78 | Jagged 1 | RAGE | WISP-1 |
| CD44v6 | | HER2/neu | Jagged 2 | SLC44A4 | WISP-2 |
| CD47 | CXCR4 | HGF | LAG-3 | Sphingosine 1 Phosphate | WISP-3 |
| CD51 | CYR61 | hGH | | | |

As a non-limiting example, the antibody or antigen-binding fragment and/or the AB of an activatable antibody is or is derived from an antibody listed in Table 2. As a non-limiting example, the AB of an activatable antibody, the AB1 of a multispecific activatable antibody, and/or the AB2 of a multispecific activatable antibody is or is derived from an antibody listed in Table 2.

TABLE 2

Exemplary sources for Abs

| Antibody Trade Name (antibody name) | Target |
|---|---|
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocrelizumab | CD20 |
| Arzerra ™ (ofatumumab) | CD20 |
| Gazyva ™ (obinutuzumab) | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
| | Notch, e.g., Notch 1 |
| | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

The disclosure also provides an isolated antibody or antigen-binding fragment thereof that specifically binds to at least one activatable antibody, conjugated activatable antibody, multispecific activatable antibody, conjugated multispecific activatable antibody, or combination thereof, wherein the antibody or antigen-binding fragment thereof comprises a variable heavy chain complementarity determining region 1 (CDRH1) comprising the amino acid sequence SYGMS (SEQ ID NO: 438); a variable heavy chain complementarity determining region 2 (CDRH2) comprising the amino acid sequence TISPSGIYTYYPVTVKG (SEQ ID NO: 439); a variable heavy chain complementarity determining region 3 (CDRH3) comprising the amino acid sequence HHPNYGSTYLYYIDY (SEQ ID NO: 440); a variable light chain complementarity determining region 1 (CDRL1) comprising the amino acid sequence KSSQSVFSSSNQKNYLA (SEQ ID NO: 441); a variable light chain complementarity determining region 2 (CDRL2) comprising the amino acid sequence WAFTRES (SEQ ID NO: 442); and a variable light chain complementarity determining region 3 (CDRL3) comprising the amino acid sequence YQYLSSLT (SEQ ID NO: 443).

In some embodiments, the antibody or antigen-binding fragment thereof comprises a variable heavy chain comprising the amino acid sequence of SEQ ID NO: 429.

In some embodiments, the antibody or antigen-binding fragment thereof comprises a variable light chain comprising the amino acid sequence of SEQ ID NO: 431.

In some embodiments, the antibody or antigen-binding fragment thereof comprises a variable heavy chain comprising the amino acid sequence of SEQ ID NO: 429, and a variable light chain comprising the amino acid sequence of SEQ ID NO: 431.

In some embodiments, the antibody or antigen-binding fragment thereof comprises an amino acid sequence that is at least 90%, 91%, 92%, 93%, 94%, 95%, 96%, 97%, 98%, 99% or more identical to a variable heavy chain comprising the amino acid sequence of SEQ ID NO: 429.

In some embodiments, the antibody or antigen-binding fragment thereof comprises an amino acid sequence that is at least 90%, 91%, 92%, 93%, 94%, 95%, 96%, 97%, 98%, 99% or more identical to a variable light chain comprising the amino acid sequence of SEQ ID NO: 431.

In some embodiments, the antibody or antigen-binding fragment thereof comprises an amino acid sequence that is at least 90%, 91%, 92%, 93%, 94%, 95%, 96%, 97%, 98%, 99% or more identical to a variable heavy chain comprising the amino acid sequence of SEQ ID NO: 429; and an amino acid sequence that is at least 90%, 91%, 92%, 93%, 94%, 95%, 96%, 97%, 98%, 99% or more identical to a variable light chain comprising the amino acid sequence of SEQ ID NO: 431.

The disclosure also provides kits for practicing any of the methods provided herein.

The disclosure provides methods and kits for qualitatively and/or quantitatively analyzing activation and other properties of activatable antibody therapeutic activation in biological samples, including tissues and/or biofluid samples.

In one embodiment, the present invention provides a kit comprising:

(i) an activatable antibody standard curve reagent;

(ii) an activated activatable antibody standard curve reagent; and (iii) an anti-id primary antibody or antigen binding fragment thereof having binding specificity for the activatable antibody. In some embodiments, the anti-idiotypic (id) antibody or antigen-binding fragment thereof has a binding specificity for a VL CDR selected from the group consisting of VL CDR1, VL CDR2, and VL CDR3. In other embodiments, the anti-iodiotypic antibody or antigen-binding fragment thereof has a binding specificity for a VH CDR selected from the group consisting of VH CDR1, VH CDR2, and VH CDR3. In some embodiments, the kit comprises a combination of two or more anti-iodiotypic antibody species (or antigen-binding fragments thereof). The standard curve reagents are relatively pure activatable antibody and activated activatable antibody in solution, ready for dilution, or in solid form.

Activatable antibodies typically include at least the following: (i) an antibody or an antigen binding fragment thereof (AB) that specifically binds a target; (ii) a masking moiety (MM) coupled to the AB such that, when the activatable antibody is in an uncleaved state, inhibits the binding of the AB to the target; and (iii) a cleavable moiety (CM) coupled to the AB, wherein the CM is a polypeptide that functions as a substrate for a protease. Activatable antibodies are generally activated when the substrate of the CM is in the presence of the protease for which it functions as a substrate, and the protease cleaves the substrate of the CM. It is useful to be able to qualitatively and/or quantitatively measure properties of activatable antibodies in biological samples, such as, for example, the level of activation of the activatable antibodies in a biological sample, the total amount of activated, i.e., cleaved, activatable antibodies and/or intact, i.e., inactivated, activatable in a biological samples, or any combination or correlation thereof. Such methods are useful in monitoring efficacy of activatable antibodies and activatable antibody-based therapeutics at any stage of development and/or therapeutic treatment. For example, in some embodiments, the methods and kits provided herein are useful for testing efficacy of activatable antibodies and activatable antibody-based therapeutics prior to administration to a subject in need thereof and/or during the treatment regimen to monitor efficacy of the activatable antibodies and activatable antibody-based therapeutics throughout the entire administration period and/or after the administration period. In some embodiments, the methods and kits provided herein are useful to provide retrospective analysis of activatable antibodies and activatable antibody-based therapeutics.

In some embodiments, the disclosure provides methods for qualitatively and/or quantitatively analyzing activatable antibody therapeutic activation in biological samples, including tissues and/or plasma samples, using a capillary-based immunoassay platform. In some embodiments, the methods provided herein are used to quantitate activation of one or more activatable antibodies in a biological sample. In some embodiments, the methods provided herein are used to profile, stratify, or otherwise categorize protease activity in vivo in a biological sample.

In some embodiments, the disclosure provides methods for qualitatively and/or quantitatively analyzing activation of activatable antibody therapeutics having an antibody or an antigen binding fragment thereof (AB) that specifically binds a target; a masking moiety (MM) coupled to the light chain of the AB such that, when the activatable antibody is in an uncleaved state, inhibits the binding of the AB to the target; and a cleavable moiety (CM) coupled to the AB, wherein the CM is a polypeptide that functions as a substrate for a protease. In some embodiments, the methods are used to quantitate or otherwise compare at least (i) the level of activated activatable antibodies in which the CM has been cleaved and the MM is not coupled to the light chain of the AB; and (ii) the level of intact activatable antibodies in which the MM and the CM are coupled to the light chain of the AB.

In some embodiments, the disclosure provides methods for qualitatively and/or quantitatively analyzing activation of activatable antibody therapeutics having an antibody or an antigen binding fragment thereof (AB) that specifically binds a target; a masking moiety (MM) coupled to the heavy chain of the AB such that, when the activatable antibody is in an uncleaved state, inhibits the binding of the AB to the target; and a cleavable moiety (CM) coupled to the AB, wherein the CM is a polypeptide that functions as a substrate for a protease. In some embodiments, the methods are used to quantitate or otherwise compare at least (i) the level of activated activatable antibodies in which the CM has been cleaved and the MM is not coupled to the heavy chain of the AB; and (ii) the level of intact activatable antibodies in which the MM and the CM are coupled to the heavy chain of the AB.

In some embodiments, the disclosure provides methods for qualitatively and/or quantitatively analyzing activation of activatable antibody therapeutics having an antibody or an antigen binding fragment thereof (AB) that specifically binds a target; a first masking moiety (MM1) coupled to the light chain of the AB, such that, when the activatable antibody is in an uncleaved state, MM1 inhibits the binding of the AB to the target; a first cleavable moiety (CM1) coupled to the light chain AB, wherein the CM1 is a polypeptide that functions as a substrate for a protease, a second masking moiety (MM2) coupled to the heavy chain of the AB, such that, when the activatable antibody is in an uncleaved state, MM2 inhibits the binding of the AB to the target; and a second cleavable moiety (CM2) coupled to the light chain AB, wherein the CM2 is a polypeptide that functions as a substrate for a protease. In some embodiments, the methods are used to quantitate or otherwise compare at least (i) the level of activated activatable antibodies in which at least one of CM1 and/or CM2 has been cleaved such that at least one of MM1 and/or MM2 is not coupled to the AB; and (ii) the level of intact activatable antibodies in which at least one of MM1 and CM1 and/or MM2 and CM2 are coupled to the AB.

In some embodiments, the disclosure provides methods of quantitating a level of activation of an activatable antibody-based therapeutic, the method comprising: i) loading at least one capillary or a population of capillaries with a stacking matrix and a separation matrix; ii) contacting the loaded capillary or population of loaded capillaries with a biological sample; iii) separating intact activatable antibodies or intact activatable antibody-based therapeutics from activated activatable antibodies or activated activatable antibody-based therapeutics in the biological sample within each capillary; iv) immobilizing the intact activatable antibodies or intact activatable antibody-based therapeutics and the activated activatable antibodies or intact activatable antibody-based therapeutics within each capillary; v) immunoprobing each capillary with at least one detectable reagent that is specific for at least one activatable antibody, conjugated activatable antibody, multispecific activatable antibody, conjugated multispecific activatable antibody, or combination thereof; and vi) quantitating a level of detectable reagent in each capillary or population of capillaries.

In some embodiments, the disclosure provides methods of quantitating a level of activation of an activatable antibody-based therapeutic, the method comprising: i) loading at least one capillary or a population of capillaries with a stacking matrix and a separation matrix; ii) contacting the loaded capillary or population of loaded capillaries with a biological sample; iii) separating high molecular weight (MW) components of the biological sample from low molecular weight (MW) components of the biological sample within each capillary; iv) immobilizing the high MW components and the low MW components within each capillary; v) immunoprobing each capillary with at least one detectable reagent that is specific for at least one activatable antibody, conjugated activatable antibody, multispecific activatable antibody, conjugated multispecific activatable antibody, or combination thereof; and vi) quantitating a level of detectable reagent in each capillary or population of capillaries.

In some embodiments, the at least one detectable reagent in step v) comprises at least a first reagent that is specific for at least one activatable antibody, conjugated activatable antibody, multispecific activatable antibody, conjugated multispecific activatable antibody, or combination thereof and a second reagent that specifically binds to or recognizes the first reagent, wherein the second reagent comprises a detectable label.

In some embodiments, step vi) comprises quantitating a level of detectable label in each capillary or population of capillaries.

In some embodiments, step ii) comprises loading approximately 1-500 ng of biological sample or any value and/or range in between approximately 1-500 ng of biological sample. In some embodiments, step ii) comprises loading approximately 5-40 ng of biological sample. Those of ordinary skill in the art will appreciate that the loading dose of biological sample can vary depending on the affinity of the detectable reagent or first reagent used in the methods, wherein the higher the affinity of the detectable reagent or first reagent is, the lower the loading dose of biological sample can be.

In some embodiments, the biological sample is prepared using one or more buffers in an amount sufficient to result in molecular weight separation. In some embodiments, the biological sample is prepared using one or more SDS-containing buffers in an amount sufficient to result in molecular weight separation. In some embodiments, the biological sample is prepared using one or more buffers in an amount sufficient to result in separation of native proteins, including activatable antibodies and/or activatable antibody-based therapeutics in biological samples. In some embodiments, the biological sample is prepared using one or more buffers in an amount sufficient to result in separation of reduced samples using any suitable reagent for separation.

In some embodiments, step iii) comprises using UV light to immobilize the high MW components and the low MW components of the biological sample. In some embodiments, any suitable immobilizing agent is used in step iii) of the methods provided herein.

In some embodiments, the first reagent in step iv) is an antibody or antigen-binding fragment thereof that specifically binds to at least one activatable antibody, conjugated activatable antibody, multispecific activatable antibody, conjugated multispecific activatable antibody, or combination thereof.

In some embodiments, the second reagent in step iv) is a detectably labeled secondary antibody that specifically binds to the first reagent.

In some embodiments, the first reagent in step iv) is a primary antibody or antigen-binding fragment thereof that specifically binds to at least one activatable antibody, conjugated activatable antibody, multispecific activatable antibody, conjugated multispecific activatable antibody, or combination thereof, and the second reagent in step v) is a detectably labeled secondary antibody that specifically binds to the primary antibody or antigen-binding fragment thereof.

In some embodiments, the detectable label is conjugated to the second reagent.

In some embodiments, the detectable label is a fluorescent label, and step vi) comprises detecting a level of chemiluminescence in each capillary or population of capillaries.

In some embodiments, the detectable label is horseradish peroxidase (HRP).

In some embodiments, the biological sample is a bodily fluid. In some embodiments, the bodily fluid is blood, plasma, or serum. In some embodiments, the biological sample is a diseased tissue. In some embodiments, the diseased tissue is a lysate. In some embodiments, the disease tissue is tumor tissue.

In some embodiments, the methods provided herein are used to compare amounts of activated and intact activatable antibody or activatable antibody-based therapeutics in a biological sample. In some embodiments, the activatable antibody-based therapeutic is a conjugated activatable antibody, a multispecific activatable antibody, a conjugated multispecific activatable antibody, or any combination thereof.

The disclosure also provides antibodies or antigen-binding fragments thereof that specifically bind to an activatable antibody and/or activatable antibody-based therapeutic, such as, for example, is a conjugated activatable antibody, a multispecific activatable antibody, a conjugated multispecific activatable antibody, or any combination thereof.

In some embodiments, the antibody or antigen-binding fragment thereof comprises a variable heavy chain complementarity determining region 1 (CDRH1) comprising the amino acid sequence SYGMS (SEQ ID NO: 438); a variable heavy chain complementarity determining region 2 (CDRH2) comprising the amino acid sequence TISPSGIYTYYPVTVKG (SEQ ID NO: 439); a variable heavy chain complementarity determining region 3 (CDRH3) comprising the amino acid sequence HHPNYGSTYLYYIDY (SEQ ID NO: 440); a variable light chain complementarity determining region 1 (CDRL1) comprising the amino acid sequence KSSQSVFSSSNQKNYLA (SEQ ID NO: 441); a variable light chain complementarity determining region 2 (CDRL2) comprising the amino acid sequence WAFTRES (SEQ ID NO: 442); and a variable light chain complementarity determining region 3 (CDRL3) comprising the amino acid sequence YQYLSSLT (SEQ ID NO: 443).

In some embodiments, the antibody or antigen-binding fragment thereof comprises a variable heavy chain comprising the amino acid sequence of SEQ ID NO: 429.

In some embodiments, the antibody or antigen-binding fragment thereof comprises a variable light chain comprising the amino acid sequence of SEQ ID NO: 431.

In some embodiments, the antibody or antigen-binding fragment thereof comprises a variable heavy chain comprising the amino acid sequence of SEQ ID NO: 429, and a variable light chain comprising the amino acid sequence of SEQ ID NO: 431.

In some embodiments, the antibody or antigen-binding fragment thereof comprises a heavy chain comprising the amino acid sequence of SEQ ID NO: 444.

In some embodiments, the antibody or antigen-binding fragment thereof comprises a light chain comprising the amino acid sequence of SEQ ID NO: 445.

In some embodiments, the antibody or antigen-binding fragment thereof comprises a heavy chain comprising the amino acid sequence of SEQ ID NO: 444, and a light chain comprising the amino acid sequence of SEQ ID NO: 445.

The methods provided herein are useful for quantifying activatable antibodies, conjugated activatable antibodies, multispecific activatable antibodies, and/or conjugated multispecific activatable antibodies.

The activatable antibodies and/or conjugated activatable antibodies include an antibody or antigen-binding fragment thereof (AB) that specifically binds a target coupled to a masking moiety (MM), such that coupling of the MM reduces the ability of the antibody or antigen-binding fragment thereof to bind the target. In some embodiments, the MM is coupled via a sequence that includes a substrate for a protease, for example, a protease that is co-localized with the target at a treatment site in a subject. In some embodiments, the target is a mammalian target, such as for example, a human target.

The multispecific activatable antibodies and/or conjugated multispecific activatable antibodies include at least (i) a first antibody or antigen-binding fragment thereof (AB1) that specifically binds a first target coupled to a first masking moiety (MM1), such that coupling of the MM1 reduces the ability of the AB1 to bind the first target, and (ii) a second antibody or antigen-binding fragment thereof (AB2) that specifically binds a second target coupled to a second masking moiety (MM2), such that coupling of the MM2 reduces the ability of the AB2 to bind the second target. In some embodiments, the MM1 and/or MM2 is coupled to the respective antibody or antigen-binding fragment thereof (AB1 or AB2) via a sequence that includes a substrate for a protease, for example, a protease that is co-localized with the first target, the second target, or both the first target and the second target at a treatment site in a subject. In some embodiments, the first target, the second target, or both the first target and the second target is a mammalian target, such as for example, a human target.

The activatable antibodies provided herein include a masking moiety. In some embodiments, the masking moiety is an amino acid sequence that is coupled or otherwise attached to the antibody and is positioned within the activatable antibody construct such that the masking moiety reduces the ability of the antibody to specifically binds the target. Suitable masking moieties are identified using any of a variety of known techniques. For example, peptide masking moieties are identified using the methods described in PCT Publication No. WO 2009/025846 by Daugherty et al., the contents of which are hereby incorporated by reference in their entirety.

The activatable antibodies provided herein include a cleavable moiety. In some embodiments, the cleavable moiety includes an amino acid sequence that is a substrate for a protease, usually an extracellular protease. Suitable substrates are identified using any of a variety of known techniques. For example, peptide substrates are identified using the methods described in U.S. Pat. No. 7,666,817 by Daugherty et al.; in U.S. Pat. No. 8,563,269 by Stagliano et al.; and in PCT Publication No. WO 2014/026136 by La Porte et al., the contents of each of which are hereby incorporated by reference in their entirety. (See also Boulware et al. "Evolutionary optimization of peptide substrates for proteases that exhibit rapid hydrolysis kinetics." Biotechnol Bioeng. 106.3 (2010): 339-46).

Exemplary substrates include but are not limited to substrates cleavable by one or more of the following enzymes or proteases listed in Table 4.

TABLE 4

| Exemplary Proteases and/or Enzymes |
|---|
| ADAMS, ADAMTS, e.g. |
| ADAM8 |
| ADAM9 |
| ADAM10 |

TABLE 4-continued

| Exemplary Proteases and/or Enzymes |
|---|
| ADAM12 |
| ADAM15 |
| ADAM17/TACE |
| ADAMDEC1 |
| ADAMTS1 |
| ADAMTS4 |
| ADAMTS5 |
| Aspartate proteases, e.g., |
| BACE |
| Renin |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| Otubain-2 |
| KLKs, e.g., |
| KLK4 |
| KLK5 |
| KLK6 |
| KLK7 |
| KLK8 |
| KLK9 |
| KLK10 |
| KLK11 |
| KLK13 |
| KLK14 |
| Metallo proteinases, e.g., |
| Meprin |
| Neprilysin |
| PSMA |
| BMP-1 |
| MMPs, e.g., |
| MMP1 |
| MMP2 |
| MMP3 |
| MMP7 |
| MMP8 |
| MMP9 |
| MMP10 |
| MMP11 |
| MMP12 |
| MMP13 |
| MMP14 |
| MMP15 |
| MMP16 |
| MMP17 |
| MMP19 |
| MMP20 |

TABLE 4-continued

| Exemplary Proteases and/or Enzymes |
| --- |
| MMP23 |
| MMP24 |
| MMP26 |
| MMP27 |
| Serine proteases, e.g., |
| activated protein C |
| Cathepsin A |
| Cathepsin G |
| Chymase |
| coagulation factor proteases (e.g., FVIIa, FIXa, FXa, FXIa, FXIIa) |
| Elastase |
| Granzyme B |
| Guanidinobenzoatase |
| HtrA1 |
| Human Neutrophil Elastase |
| Lactoferrin |
| Marapsin |
| NS3/4A |
| PACE4 |
| Plasmin |
| PSA |
| tPA |
| Thrombin |
| Tryptase |
| uPA |
| Type II Transmembrane Serine Proteases (TTSPs), e.g., |
| DESC1 |
| DPP-4 |
| FAP |
| Hepsin |
| Matriptase-2 |
| MT-S Pl/Matriptase |
| TMPRSS2 |
| TMPRSS3 |
| TMPRSS4 |

The methods provided herein are useful to quantitate activation of activatable antibodies, which include a cleavable moiety that functions as a substrate for a protease. Activatable antibodies described herein have been designed to overcome a limitation of antibody therapeutics, particularly antibody therapeutics that are known to be toxic to at least some degree in vivo. Target-mediated toxicity constitutes a major limitation for the development of therapeutic antibodies. The activatable antibodies provided herein are designed to address the toxicity associated with the inhibition of the target in normal tissues by traditional therapeutic antibodies. These activatable antibodies remain masked until proteolytically activated at the site of disease. Starting with an antibody as a parental therapeutic antibody, the activatable antibodies of the invention were engineered by coupling the antibody to an inhibitory mask through a linker that incorporates a protease substrate.

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or of the parental AB towards the target. Conversely, the binding affinity of the AB modified with a MM towards the target is at least 2, 3, 4, 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or of the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

In some embodiments, the dissociation constant ($K_d$) of the MM towards the AB is approximately equal to the $K_d$ of the AB towards the target. In some embodiments, the dissociation constant ($K_d$) of the MM towards the AB is no more than the dissociation constant of the AB towards the target. In some embodiments, the dissociation constant ($K_d$) of the MM towards the AB is equivalent to the dissociation constant of the AB towards the target.

In some embodiments, the dissociation constant ($K_d$) of the MM towards the AB is less than the dissociation constant of the AB towards the target.

In some embodiments, the dissociation constant ($K_d$) of the MM towards the AB is greater than the dissociation constant of the AB towards the target.

In some embodiments, the MM has a $K_d$ for binding to the AB that is no more than the $K_d$ for binding of the AB to the target.

In some embodiments, the MM has a $K_d$ for binding to the AB that is no less than the $K_d$ for binding of the AB to the target.

In some embodiments, the MM has a $K_d$ for binding to the AB that is approximately equal to the $K_d$ for binding of the AB to the target.

In some embodiments, the MM has a $K_d$ for binding to the AB that is less than the $K_d$ for binding of the AB to the target.

In some embodiments, the MM has a $K_d$ for binding to the AB that is greater than the $K_d$ for binding of the AB to the target.

In some embodiments, the MM has a $K_d$ for binding to the AB that is no more than 2, 3, 4, 5, 10, 25, 50, 100, 250, 500, or 1,000 fold greater than the $K_d$ for binding of the AB to the target. In some embodiments, the MM has a $K_d$ for binding to the AB that is between 1-5, 2-5, 2-10, 5-10, 5-20, 5-50, 5-100, 10-100, 10-1,000, 20-100, 20-1000, or 100-1,000 fold greater than the $K_d$ for binding of the AB to the target.

In some embodiments, the MM has an affinity for binding to the AB that is less than the affinity of binding of the AB to the target.

In some embodiments, the MM has an affinity for binding to the AB that is no more than the affinity of binding of the AB to the target.

In some embodiments, the MM has an affinity for binding to the AB that is approximately equal of the affinity of binding of the AB to the target.

In some embodiments, the MM has an affinity for binding to the AB that is no less than the affinity of binding of the AB to the target.

In some embodiments, the MM has an affinity for binding to the AB that is greater than the affinity of binding of the AB to the target.

In some embodiments, the MM has an affinity for binding to the AB that is 2, 3, 4, 5, 10, 25, 50, 100, 250, 500, or 1,000 less than the affinity of binding of the AB to the target. I In some embodiments, the MM has an affinity for binding to the AB that is between 1-5, 2-5, 2-10, 5-10, 5-20, 5-50, 5-100, 10-100, 10-1,000, 20-100, 20-1000, or 100-1,000 fold less than the affinity of binding of the AB to the target. In some embodiments, the MM has an affinity for binding to the AB that is 2 to 20 fold less than the affinity of binding of the AB to the target. In some embodiments, a MM not covalently linked to the AB and at equimolar concentration to the AB does not inhibit the binding of the AB to the target.

When the AB is modified with a MM and is in the presence of the target specific binding of the AB to its target is reduced or inhibited, as compared to the specific binding of the AB not modified with an MM or the specific binding of the parental AB to the target. When compared to the binding of the AB not modified with an MM or the binding of the parental AB to the target the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified or coupled to a MM and in the presence of target there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it can be desirable to insert one or more linkers, e.g., flexible linkers, into the composition so as to provide for flexibility.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibodies include an AB that is modified by an MM and also includes one or more cleavable moieties (CM). Such activatable antibodies exhibit activatable/switchable binding, to the AB's target. Activatable antibodies generally include an antibody or antibody fragment (AB), modified by or coupled to a masking moiety (MM) and a modifiable or cleavable moiety (CM). In some embodiments, the CM contains an amino acid sequence that serves as a substrate for at least one protease.

The elements of the activatable antibodies are arranged so that the MM and CM are positioned such that in a cleaved (or relatively active) state and in the presence of a target, the AB binds a target while the activatable antibody is in an uncleaved (or relatively inactive) state in the presence of the target, specific binding of the AB to its target is reduced or inhibited. The specific binding of the AB to its target can be reduced due to the inhibition or masking of the AB's ability to specifically bind its target by the MM.

The $K_d$ of the AB modified with a MM and a CM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM or of the parental AB towards the target. Conversely, the binding affinity of the AB modified with a MM and a CM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM or of the parental AB towards the target.

When the AB is modified with a MM and a CM and is in the presence of the target but not in the presence of a modifying agent (for example at least one protease), specific binding of the AB to its target is reduced or inhibited, as compared to the specific binding of the AB not modified with an MM and a CM or of the parental AB to the target. When compared to the binding of the parental AB or the binding of an AB not modified with an MM and a CM to its target, the AB's ability to bind the target when modified with an MM and a CM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification of the CM by at least one protease. The term uncleaved state, as used herein, refers to the condition of the activatable antibodies in the absence of cleavage of the CM by a protease. As discussed above, the term "activatable antibodies" is used herein to refer to an activatable antibody in both its uncleaved (native) state, as well as in its cleaved state. It will be apparent to the ordinarily skilled artisan that in some embodiments a cleaved activatable antibody may lack an MM due to cleavage of the CM by protease, resulting in release of at least the MM (e.g., where the MM is not joined to the activatable antibodies by a covalent bond (e.g., a disulfide bond between cysteine residues).

By activatable or switchable is meant that the activatable antibody exhibits a first level of binding to a target when the activatable antibody is in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM, i.e., a protease, than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM and AB of the activatable antibodies are selected so that the AB represents a binding moiety for a given target, and the CM represents a substrate for a protease. In some embodiments, the protease is co-localized with the target at a treatment site or diagnostic site in a subject. As used herein, co-localized refers to being at the same site or relatively close nearby. In some embodiments, a protease cleaves a CM yielding an activated antibody that binds to a target located nearby the cleavage site. The activatable antibodies disclosed herein find particular use where, for example, a protease capable of cleaving a site in the CM, i.e., a protease, is present at relatively higher levels in target-containing tissue of a treatment site or diagnostic site than in tissue of non-treatment sites (for example in healthy tissue). In some embodiments, a CM of the disclosure is also cleaved by one or more other proteases. In some embodiments, it is the one or more other proteases that is co-localized with the target and that is responsible for cleavage of the CM in vivo.

In some embodiments, activatable antibodies provide for reduced toxicity and/or adverse side effects that could otherwise result from binding of the AB at non-treatment sites if the AB were not masked or otherwise inhibited from binding to the target.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein binding to an activatable antibody in the presence of at least one protease capable of cleaving the CM of the activatable antibodies to (b) a minimum detected level of target protein binding to an activatable antibody in the absence of the protease. The dynamic range of an activatable antibody can be calculated as the ratio of the dissociation constant of an activatable antibody cleaving agent (e.g., enzyme) treatment to the dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM can be reversed within an activatable antibody. It is also specifically contemplated that the CM and MM may overlap in amino acid sequence, e.g., such that the CM is contained within the MM.

For example, activatable antibodies can be represented by the following formula (in order from an amino (N) terminal region to carboxyl (C) terminal region:

(MM)-(CM)-(AB)

(AB)-(CM)-(MM)

where MM is a masking moiety, CM is a cleavable moiety, and AB is an antibody or fragment thereof. It should be noted that although MM and CM are indicated as distinct components in the formulae above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that can be positioned N-terminal or C-terminal to the activatable antibodies elements.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibody includes one or more linkers, e.g., flexible linkers, into the activatable antibody construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments, an activatable antibody comprises one of the following formulae (where the formula below represent an amino acid sequence in either N- to C-terminal direction or C- to N-terminal direction):

(MM)-L1-(CM)-(AB)

(MM)-(CM)-L2-(AB)

(MM)-L1-(CM)-L2-(AB)

wherein MM, CM, and AB are as defined above; wherein L1 and L2 are each independently and optionally present or absent, are the same or different flexible linkers that include at least 1 flexible amino acid (e.g., Gly). In addition, the formulae above provide for additional amino acid sequences that can be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

The CM is specifically cleaved by at least one protease at a rate of about 0.001-1500×$10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or 1500×$10^4$ $M^{-1}S^{-1}$. In some embodiments, the CM is specifically cleaved at a rate of about 100,000 $M^{-1}S^{-1}$. In some embodiments, the CM is specifically cleaved at a rate from about 1×$10^2$ to about 1×$10^6$ $M^{-1}S^{-1}$ (i.e., from about 1×$10^2$ to about 1×$10^6$ $M^{-1}S^{-1}$).

For specific cleavage by an enzyme, contact between the enzyme and CM is made. When the activatable antibody comprising an AB coupled to a MM and a CM is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS)n, (GSGGS)n (SEQ ID NO: 339) and (GGGS)n (SEQ ID NO: 340), where n is an integer of at least one, and in some embodiments, not greater than twenty, glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 341), Gly-Gly-Ser-Gly-Gly (SEQ ID NO: 342), Gly-Ser-Gly-Ser-Gly (SEQ ID NO: 343), Gly-Ser-Gly-Gly-Gly (SEQ ID NO: 344), Gly-Gly-Gly-Ser-Gly (SEQ ID NO: 345), Gly-Ser-Ser-Ser-Gly (SEQ ID NO: 346), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

The disclosure also provides compositions and methods for quantifying an activatable antibody that has been modified to enable the attachment of one or more agents to one or more cysteine residues in the AB without compromising the activity (e.g., the masking, activating or binding activity) of the activatable antibody. In some embodiments, the activatable antibody that has been modified to enable the attachment of one or more agents to one or more cysteine residues in the AB without reducing or otherwise disturbing one or more disulfide bonds within the MM. The compositions and methods provided herein can be run using an activatable antibody that is conjugated to one or more agents, e.g., any of a variety of therapeutic, diagnostic and/or prophylactic agents, for example, in some embodiments, without any of the agent(s) being conjugated to the MM of the activatable antibody. The compositions and methods provided herein are used with conjugated activatable antibodies in which the MM retains the ability to effectively and efficiently mask the AB of the activatable antibody in an uncleaved state. The compositions and methods provided herein are used with conjugated activatable antibodies in which the activatable antibody is still activated, i.e., cleaved, in the presence of a protease that can cleave the CM.

The activatable antibodies have at least one point of conjugation for an agent, but in the methods and compositions provided herein, less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or can be incorporated into the antibody by site-directed mutagenesis, chemical conversion, or mis-incorporation of non-natural amino acids.

The composition and methods provided herein can also use a conjugate of an activatable antibody having one or more interchain disulfide bonds in the AB and one or more intrachain disulfide bonds in the MM, wherein a drug reactive with free thiols is provided. In these embodiments, the method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In yet other embodiments, the compositions and methods provided herein are used in conjunction with a method of reducing and conjugating an agent, e.g., a drug, to an activatable antibody resulting in selectivity in the placement of the agent is provided. In these embodiments, the method generally includes partially reducing the activatable antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable antibody will vary depending on the activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

In some embodiments, the compositions and methods provided herein are used in conjunction with a method of reducing interchain disulfide bonds in the AB of an activatable antibody and conjugating an agent, e.g., a thiol-containing agent such as a drug, to the resulting interchain thiols to selectively locate agent(s) on the AB is provided. In these embodiments, the method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. Alternatively, the reduced antibody is not purified after partial reduction and prior to conjugation.

In some embodiments, the compositions and methods provided herein are used with partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds a target, a masking moiety (MM) that inhibits the binding of the AB of the activatable antibody in an uncleaved state to the target, and a cleavable moiety (CM) coupled to the AB, wherein the CM is a polypeptide that functions as a substrate for a protease. In some embodiments the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

In yet other embodiments, the compositions and methods provided herein are used in conjunction with a method of reducing and conjugating an agent, e.g., a drug, to an activatable antibody resulting in selectivity in the placement of the agent by providing an activatable antibody with a defined number and positions of lysine and/or cysteine residues. In some embodiments, the defined number of lysine and/or cysteine residues is higher or lower than the number of corresponding residues in the amino acid sequence of the parent antibody or activatable antibody. In some embodiments, the defined number of lysine and/or cysteine residues may result in a defined number of agent equivalents that can be conjugated to the antibody or activatable antibody. In some embodiments, the defined number of lysine and/or cysteine residues may result in a defined number of agent equivalents that can be conjugated to the antibody or activatable antibody in a site-specific manner. In some embodiments, the modified activatable antibody is modified with one or more non-natural amino acids in a site-specific manner, thus in some embodiments limiting the conjugation of the agents to only the sites of the non-natural amino acids. In some embodiments, the antibody or activatable antibody with a defined number and positions of lysine and/or cysteine residues can be partially reduced with a reducing agent as discussed herein such that any conjugation sites in the masking moiety or other non-AB portion of the activatable antibody are not reduced, and conjugating the agent to interchain thiols in the AB.

In some embodiments, the compositions and methods provided herein are used with partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to the target, a masking moiety (MM) that inhibits the binding of the AB of the activatable antibody in an uncleaved state to the target, and a cleavable moiety (CM) coupled to the AB, wherein the CM is a polypeptide that functions as a substrate for at least one protease. In some embodiments, the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

In some embodiments, the compositions and methods provided herein are used with activatable antibodies that also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

In some embodiments, the compositions and methods provided herein are used with immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE, MMAD, DMAF, DMAE). For example, the agent is monomethyl auristatin E (MMAE) or monomethyl auristatin D (MMAD). In some embodiments, the agent is an agent selected from the group listed in Table 5. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is linked to the AB using a maleimide caproyl-valine-citrulline linker or a maleimide PEG-valine-citrulline linker. In some embodiments, the agent is linked to the AB using a maleimide caproyl-valine-citrulline linker. In some embodiments, the agent is linked to the AB using a maleimide PEG-valine-citrulline linker In some embodiments, the agent is monomethyl auristatin D (MMAD) linked to the AB using a maleimide PEG-valine-citrulline-para-aminobenzyloxycarbonyl linker, and this linker payload construct is referred to herein as "vc-MMAD." In some embodiments, the agent is monomethyl auristatin E (MMAE) linked to the AB using a maleimide PEG-valine-citrulline-para-aminobenzyloxycarbonyl linker, and this linker payload construct is referred to herein as "vc-MMAE." In some embodiments, the agent is linked to the AB using a maleimide PEG-valine-citrulline linker In some embodiments, the agent is monomethyl auristatin D (MMAD) linked to the AB using a maleimide bis-PEG-valine-citrulline-para-aminobenzyloxycarbonyl linker, and this linker payload construct is referred to herein as "PEG2-vc-MMAD." The structures of vc-MMAD, vc-MMAE, and PEG2-vc-MMAD are shown below:

vc-MMAD

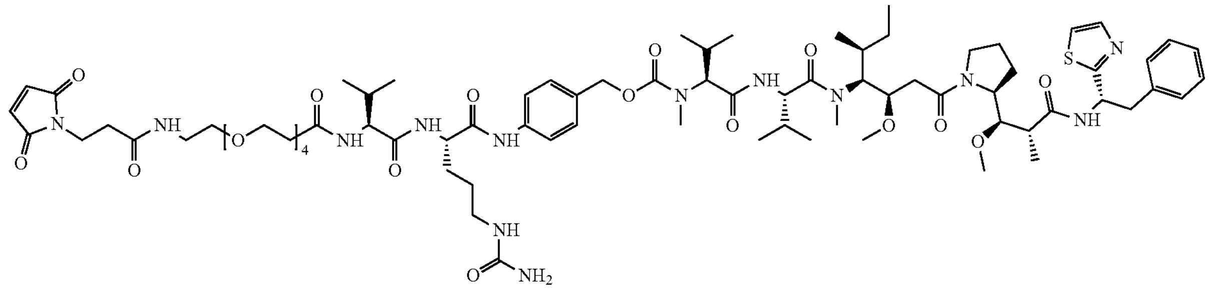

vc-MMAE

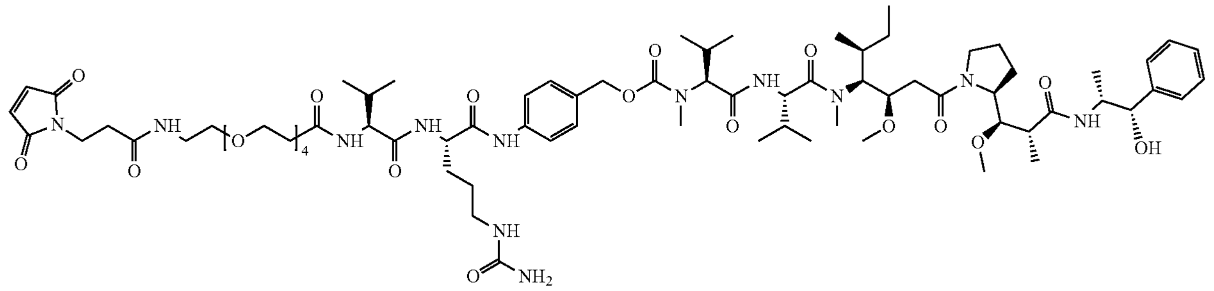

PEG2-vc-MMAD

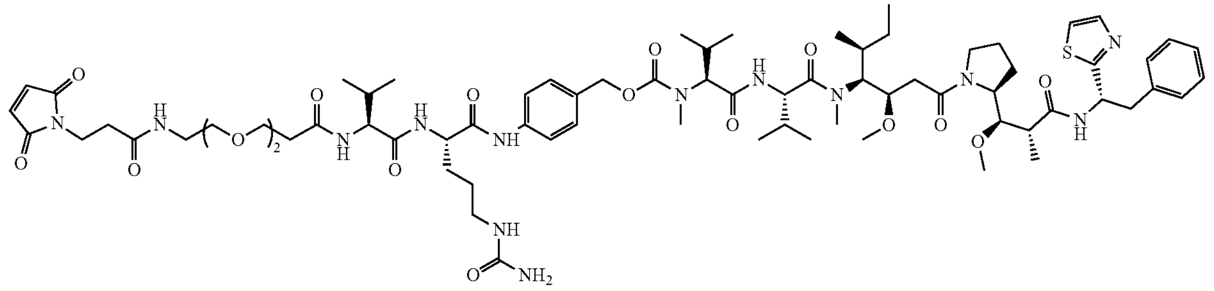

Payload for C-26

In some embodiments, the compositions and methods provided herein are used with conjugated activatable antibodies that include an activatable antibody linked to monomethyl auristatin D (MMAD) payload, wherein the activatable antibody includes an antibody or an antigen binding fragment thereof (AB) that specifically binds to a target, a masking moiety (MM) that inhibits the binding of the AB of the activatable antibody in an uncleaved state to the target, and cleavable moiety (CM) coupled to the AB, and the CM is a polypeptide that functions as a substrate for at least one MMP protease.

In some embodiments, the MMAD-conjugated activatable antibody can be conjugated using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB.

In some embodiments, the MMAD payload is conjugated to the AB via a linker. In some embodiments, the MMAD payload is conjugated to a cysteine in the AB via a linker. In some embodiments, the MMAD payload is conjugated to a lysine in the AB via a linker. In some embodiments, the MMAD payload is conjugated to another residue of the AB via a linker, such as those residues disclosed herein. In some embodiments, the linker is a thiol-containing linker. In some embodiments, the linker is a cleavable linker. In some embodiments, the linker is a non-cleavable linker. In some embodiments, the linker is selected from the group consisting of the linkers shown in Tables 6 and 7. In some embodiments, the activatable antibody and the MMAD payload are linked via a maleimide caproyl-valine-citrulline linker. In some embodiments, the activatable antibody and the MMAD payload are linked via a maleimide PEG-valine-citrulline linker. In some embodiments, the activatable antibody and the MMAD payload are linked via a maleimide caproyl-valine-citrulline-para-aminobenzyloxycarbonyl linker. In some embodiments, the activatable antibody and the MMAD payload are linked via a maleimide PEG-valine-citrulline-para-aminobenzyloxycarbonyl linker. In some embodiments, the MMAD payload is conjugated to the AB using the partial reduction and conjugation technology disclosed herein.

In some embodiments, the polyethylene glycol (PEG) component of a linker of the present disclosure is formed from 2 ethylene glycol monomers, 3 ethylene glycol monomers, 4 ethylene glycol monomers, 5 ethylene glycol monomers, 6 ethylene glycol monomers, 7 ethylene glycol monomers 8 ethylene glycol monomers, 9 ethylene glycol monomers, or at least 10 ethylene glycol monomers. In some embodiments of the present disclosure, the PEG component is a branched polymer. In some embodiments of the present disclosure, the PEG component is an unbranched polymer. In some embodiments, the PEG polymer component is functionalized with an amino group or derivative thereof, a carboxyl group or derivative thereof, or both an amino group or derivative thereof and a carboxyl group or derivative thereof.

In some embodiments, the PEG component of a linker of the present disclosure is an amino-tetra-ethylene glycol-carboxyl group or derivative thereof. In some embodiments, the PEG component of a linker of the present disclosure is an amino-tri-ethylene glycol-carboxyl group or derivative thereof. In some embodiments, the PEG component of a linker of the present disclosure is an amino-di-ethylene glycol-carboxyl group or derivative thereof. In some embodiments, an amino derivative is the formation of an amide bond between the amino group and a carboxyl group to which it is conjugated. In some embodiments, a carboxyl derivative is the formation of an amide bond between the carboxyl group and an amino group to which it is conjugated. In some embodiments, a carboxyl derivative is the formation of an ester bond between the carboxyl group and a hydroxyl group to which it is conjugated.

Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutarelde-hyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 5 lists some of the exemplary pharmaceutical agents that can be employed in the herein described disclosure but in no way is meant to be an exhaustive list.

TABLE 5

| Exemplary Pharmaceutical Agents for Conjugation |
|---|
| CYTOTOXIC AGENTS |
| Auristatins |
| Auristatin E |
| Monomethyl auristatin D (MMAD) |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |
| 10,11-Difluoromethylenedioxycamptothecin |
| Combretastatins |
| Debromoaplysiatoxin |
| Kahalalide-F |
| Discodermolide |
| Ecteinascidins |
| ANTIVIRALS |
| Acyclovir |
| Vira A |
| Symmetrel |
| ANTIFUNGALS |
| Nystatin |
| ADDITIONAL ANTI-NEOPLASTICS |
| Adriamycin |
| Cerubidine |
| Bleomycin |
| Alkeran |
| Velban |
| Oncovin |
| Fluorouracil |
| Methotrexate |
| Thiotepa |
| Bisantrene |
| Novantrone |
| Thioguanine |
| Procarabizine |
| Cytarabine |
| ANTI-BACTERIALS |
| Aminoglycosides |
| Streptomycin |
| Neomycin |
| Kanamycin |
| Amikacin |
| Gentamicin |
| Tobramycin |
| Streptomycin B |
| Spectinomycin |
| Ampicillin |
| Sulfanilamide |
| Polymyxin |
| Chloramphenicol |
| Turbostatin |
| Phenstatins |
| Hydroxyphenstatin |
| Spongistatin 5 |
| Spongistatin 7 |
| Halistatin 1 |
| Halistatin 2 |
| Halistatin 3 |
| Modified Bryostatins |
| Halocomstatins |

TABLE 5-continued

| Exemplary Pharmaceutical Agents for Conjugation |
| --- |
| Pyrrolobenzimidazoles (PBI) |
| Cibrostatin6 |
| Doxaliform |
| Anthracyclins analogues |
| Cemadotin analogue (CemCH2-SH) |
| Pseudomonas toxin A (PE38) variant |
| Pseudomonas toxin A (ZZ-PE38) variant |
| ZJ-101 |
| OSW-1 |
| 4-Nitrobenzyloxycarbonyl Derivatives of O6-Benzylguanine |
| Topoisomerase inhibitors |
| Hemiasterlin |
| Cephalotaxine |
| Homoharringtonine |
| Pyrrolobenzodiazepine dimers (PBDs) |
| Pyrrolobenzodiazepenes |
| Functionalized pyrrolobenzodiazepenes |
| Functionalized pyrrolobenzodiazepene dimers |
| Calicheamicins |
| Podophyllotoxins |
| Taxanes |
| Vinca alkaloids |
| CONJUGATABLE DETECTION REAGENTS |
| Fluorescein and derivatives thereof |
| Fluorescein isothiocyanate (FITC) |
| RADIOPHARMACEUTICALS |
| $^{125}I$ |
| $^{131}I$ |
| $^{89}Zr$ |
| $^{111}In$ |
| $^{123}I$ |
| $^{131}I$ |
| $^{99}mTc$ |
| $^{201}Tl$ |
| $^{133}Xe$ |
| $^{11}C$ |
| $^{62}Cu$ |
| $^{18}F$ |
| $^{68}Ga$ |
| $^{13}N$ |
| $^{15}O$ |
| $^{38}K$ |
| $^{82}Rb$ |
| $^{99}mTc$ (Technetium) |
| HEAVY METALS |
| Barium |
| Gold |
| Platinum |
| ANTI-MYCOPLASMALS |
| Tylosine |
| Spectinomycin |

Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, N.Y., (1989), the entire contents of which are incorporated herein by reference).

Coupling can be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

In some embodiments, the compositions and methods provided herein are used with a conjugated activatable antibody that has been modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. In some embodiments, suitable linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC. Additional linkers include, but are not limited to, SMCC ((succinimidyl 4-(N-maleimidomethyl)cyclohexane-1-carboxylate), sulfo-SMCC (sulfosuccinimidyl 4-(N-maleimidomethyl)cyclohexane-1-carboxylate), SPDB (N-succinimidyl-4-(2-pyridyldithio) butanoate), or sulfo-SPDB (N-succinimidyl-4-(2-pyridyldithio)-2-sulfo butanoate).

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the linkers are cleavable. In some embodiments, the linkers are non-cleavable. In some embodiments, two or more linkers are present. The two or more linkers are all the same, i.e., cleavable or non-cleavable, or the two or more linkers are different, i.e., at least one cleavable and at least one non-cleavable.

The agents can be attached to the Abs using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. In some embodiments, ABs can be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or can be introduced by suitable chemical modification of linkers not containing such groups.

According to the present disclosure, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present disclosure, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present disclosure, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent can be attached to the linker before or after the linker is attached to the AB. In certain applications it may be desirable to first produce an AB-linker intermediate in which the linker is free of an associated agent. Depending upon the particular application, a specific agent may then be covalently attached to the linker. In some embodiments, the AB is first attached to the MM, CM and associated linkers and then attached to the linker for conjugation purposes.

Branched Linkers: In specific embodiments, branched linkers that have multiple sites for attachment of agents are utilized. For multiple site linkers, a single covalent attachment to an AB would result in an AB-linker intermediate capable of binding an agent at a number of sites. The sites can be aldehyde or sulfhydryl groups or any chemical site to which agents can be attached.

In some embodiments, higher specific activity (or higher ratio of agents to AB) can be achieved by attachment of a single site linker at a plurality of sites on the AB. This plurality of sites can be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker can be aldehyde or sulfhydryl groups, or can be any chemical site to which linkers can be attached. Still higher specific activities can be obtained by combining these two approaches, that is, attaching multiple site linkers at several sites on the AB.

Cleavable Linkers: Peptide linkers that are susceptible to cleavage by enzymes of the complement system, such as but not limited to u-plasminogen activator, tissue plasminogen activator, trypsin, plasmin, or another enzyme having proteolytic activity can be used in one embodiment of the present disclosure. According to one method of the present disclosure, an agent is attached via a linker susceptible to cleavage by complement. The antibody is selected from a class that can activate complement. The antibody-agent conjugate, thus, activates the complement cascade and releases the agent at the target site. According to another method of the present disclosure, an agent is attached via a linker susceptible to cleavage by enzymes having a proteolytic activity such as a u-plasminogen activator, a tissue plasminogen activator, plasmin, or trypsin. These cleavable linkers are useful in conjugated activatable antibodies that include an extracellular toxin, e.g., by way of non-limiting example, any of the extracellular toxins shown in Table 5.

Non-limiting examples of cleavable linker sequences are provided in Table 6.

TABLE 6

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 615) |
| | PRFRIIGG (SEQ ID NO: 616) |
| TGFβ | SSRHRRALD (SEQ ID NO: 617) |
| Plasminogen | RKSSIIIRMRDVVL (SEQ ID NO: 618) |
| Staphylokinase | SSSFDKGKYKKGDDA (SEQ ID NO: 619) |
| | SSSFDKGKYKRGDDA (SEQ ID NO: 620) |

TABLE 6-continued

| Exemplary Linker Sequences for Conjugation | |
|---|---|
| Types of Cleavable Sequences | Amino Acid Sequence |
| Factor Xa cleavable sequences | |
| | IEGR (SEQ ID NO: 621) |
| | IDGR (SEQ ID NO: 622) |
| | GGSIDGR (SEQ ID NO: 623) |
| MMP cleavable sequences | |
| Gelatinase A | PLGLWA (SEQ ID NO: 624) |
| Collagenase cleavable sequences | |
| Calf skin collagen (α1(I) chain) | GPQGIAGQ (SEQ ID NO: 625) |
| Calf skin collagen (α2(I) chain) | GPQGLLGA (SEQ ID NO: 626) |
| Bovine cartilage collagen (α1(II) chain) | GIAGQ (SEQ ID NO: 627) |
| Human liver collagen (α1(III) chain) | GPLGIAGI (SEQ ID NO: 628) |
| Human $\alpha_2$M | GPEGLRVG (SEQ ID NO: 629) |
| Human PZP | YGAGLGVV (SEQ ID NO: 630) |
| | AGLGVVER (SEQ ID NO: 631) |
| | AGLGISST (SEQ ID NO: 632) |
| Rat α1M | EPQALAMS (SEQ ID NO: 633) |
| | QALAMSAI (SEQ ID NO: 634) |
| Rat α2M | AAYHLVSQ (SEQ ID NO: 635) |
| | MDAFLESS (SEQ ID NO: 636) |
| Rat $\alpha_1I_3$(2J) | ESLPVVAV (SEQ ID NO: 637) |
| Rat $a_1I_3$(27J) | SAPAVESE (SEQ ID NO: 638) |
| Human fibroblast collagenase (autolytic cleavages) | DVAQFVLT (SEQ ID NO: 639) |
| | VAQFVLTE (SEQ ID NO: 640) |
| | AQFVLTEG (SEQ ID NO: 641) |
| | PVQPIGPQ (SEQ ID NO: 642) |

In addition, agents can be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In some embodiments, the reducing agent that would modify a CM would also modify the linker of the conjugated activatable antibody.

Spacers and Cleavable Elements: In some embodiments, it may be necessary to construct the linker in such a way as to optimize the spacing between the agent and the AB of the activatable antibody. This can be accomplished by use of a linker of the general structure:

$$W—(CH_2)n\text{-}Q$$

wherein

W is either —NH—$CH_2$— or —$CH_2$—;

Q is an amino acid, peptide; and n is an integer from 0 to 20.

In some embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers: According to one method of the present disclosure, when release of an agent is desired, an AB that is an antibody of a class that can activate complement is used. The resulting conjugate retains both the ability to bind antigen and activate the complement cascade. Thus, according to this embodiment of the present disclosure, an agent is joined to one end of the cleavable linker or cleavable element and the other end of the linker group is attached to a specific site on the AB. For example, if the agent has an hydroxy group or an amino group, it can be attached to the carboxy terminus of a peptide, amino acid or other suitably chosen linker via an ester or amide bond, respectively. For example, such agents can be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) can be of any desired length, one end of which can be covalently attached to specific sites on the AB of the activatable antibody. The other end of the linker or spacer element can be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 5.

Linkers for Release without Complement Activation: In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates can be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers: In some embodiments, the activatable antibody can be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome can be used, for example: bis-sialyl ether. Other suitable linkers include cathepsin-labile substrates, particularly those that show optimal function at an acidic pH.

Exemplary hetero-bifunctional cross-linkers are referenced in Table 7.

TABLE 7

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines<br>Sulfhydryls | Greater stability | 11.2 Å |
| SPDP | Primary amines<br>Sulfhydryls | Thiolation<br>Cleavable cross-linking | 6.8 Å |
| LC-SPDP | Primary amines<br>Sulfhydryls | Extended spacer arm | 15.6 Å |
| Sulfo-LC-SPDP | Primary amines<br>Sulfhydryls | Extender spacer arm<br>Water-soluble | 15.6 Å |
| SMCC | Primary amines | Stable maleimide reactive group | 11.6 Å |
| | Sulfhydryls | Enzyme-antibody conjugation<br>Hapten-carrier protein conjugation | |
| Sulfo-SMCC | Primary amines | Stable maleimide reactive group | 11.6 Å |
| | Sulfhydryls | Water-soluble<br>Enzyme-antibody conjugation | |
| MBS | Primary amines | Enzyme-antibody conjugation | 9.9 Å |
| | Sulfhydryls | Hapten-carrier protein conjugation | |
| Sulfo-MBS | Primary amines<br>Sulfhydryls | Water-soluble | 9.9 Å |
| SIAB | Primary amines<br>Sulfhydryls | Enzyme-antibody conjugation | 10.6 Å |
| Sulfo-SIAB | Primary amines<br>Sulfhydryls | Water-soluble | 10.6 Å |
| SMPB | Primary amines<br>Sulfhydryls | Extended spacer arm<br>Enzyme-antibody conjugation | 14.5 Å |
| Sulfo-SMPB | Primary amines<br>Sulfhydryls | Extended spacer arm<br>Water-soluble | 14.5 Å |
| EDE/Sulfo-NHS | Primary amines<br>Carboxyl groups | Hapten-Carrier conjugation | 0 |
| ABH | Carbohydrates<br>Nonselective | Reacts with sugar groups | 11.9 Å |

Non-Cleavable Linkers or Direct Attachment: In some embodiments of the disclosure, the conjugate can be designed so that the agent is delivered to the target but not released. This can be accomplished by attaching an agent to an AB either directly or via a non-cleavable linker.

These non-cleavable linkers may include amino acids, peptides, D-amino acids or other organic compounds that can be modified to include functional groups that can subsequently be utilized in attachment to ABs by the methods described herein. A-general formula for such an organic linker could be $$W—(CH_2)n–Q$$

wherein

W is either —NH—$CH_2$— or —$CH_2$—;

Q is an amino acid, peptide; and n is an integer from 0 to 20.

Non-Cleavable Conjugates: In some embodiments, a compound can be attached to ABs that do not activate complement. When using ABs that are incapable of complement activation, this attachment can be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d>10^{-6}$). Antibodies include, but are not limited to, polyclonal, monoclonal, chimeric, domain antibody, single chain, Fab, and $F(ab')_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, IgG2, and others. Furthermore, in humans, the light chain can be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies can be raised against N-terminal or C-terminal peptides of a polypeptide. An antibody is said to specifically bind an antigen when the dissociation constant is ≤1 μM; in some embodiments, ≤100 nM and in some embodiments, ≤10 nM.

As used herein, the terms "specific binding," "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:185-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to the target, when the binding constant ($K_d$) is ≤1 μM, in some embodiments ≤100 nM, in some embodiments ≤10 nM, and in some embodiments ≤100 μM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Green, Eds., Sinauer Associates, Sunderland, Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that can be used to define structural and functional domains in accordance with the disclosure.

Suitable amino acid substitutions are those that: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) can be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to the target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and can be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Antibodies and/or activatable antibodies of the disclosure specifically bind a given target, e.g., a human target protein. Also included in the disclosure are antibodies and/or activatable antibodies that bind to the same epitope as the antibodies and/or activatable antibodies described herein. Also included in the disclosure are antibodies and/or antibodies activatable antibodies that compete with an antibody and/or an activatable antibody described herein for binding to a target. Also included in the disclosure are antibodies and/or antibodies activatable antibodies that cross-compete with an antibody and/or an activatable antibody described herein for binding to a target.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the target. If the monoclonal antibody being tested competes with the monoclonal antibody of the disclosure, as shown by a decrease in binding by the monoclonal antibody of the disclosure, then the two monoclonal antibodies bind to the same, or a closely related, epitope. An alternative method for determining whether a monoclonal antibody has the specificity of a monoclonal antibody of the disclosure is to pre-incubate the monoclonal antibody of the disclosure with the target and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the disclosure.

Multispecific Activatable Antibodies

The disclosure also provides methods and compositions using multispecific activatable antibodies. The multispecific activatable antibodies provided herein are multispecific antibodies that recognize a target and at least one or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a cleavable moiety (CM) that functions as a substrate for at least one protease. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the multispecific activatable antibodies are designed to engage immune effector cells, also referred to herein as immune-effector cell engaging multispecific activatable antibodies. In some embodiments, the multispecific activatable antibodies are designed to engage leukocytes, also referred to herein as leukocyte engaging multispecific activatable antibodies. In some embodiments, the multispecific activatable antibodies are designed to engage T cells, also referred to herein as T-cell engaging multispecific activatable antibodies. In some embodiments, the multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific activatable antibodies are designed to bind or otherwise interact with more than one target and/or more than one epitope, also referred to herein as multi-antigen targeting activatable antibodies. As used herein, the terms "target" and "antigen" are used interchangeably.

In some embodiments, immune effector cell engaging multispecific activatable antibodies of the disclosure include a targeting antibody or antigen-binding fragment thereof that binds a target and an immune effector cell engaging antibody or antigen-binding portion thereof, where at least one of the targeting antibody or antigen-binding fragment thereof and/or the immune effector cell engaging antibody or antigen-binding portion thereof is masked. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a target, where the AB2 is attached to a masking moiety (MM2) such that coupling of the MM2 reduces the ability of the AB2 to binds the target. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a target, where the AB2 is attached to a masking moiety (MM2) such that coupling of the MM2 reduces the ability of the AB2 to binds the target. In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, T-cell engaging multispecific activatable antibodies of the disclosure include a targeting antibody or antigen-binding fragment thereof and a T-cell engaging antibody or antigen-binding portion thereof, where at least one of the targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a target, where the AB2 is attached to a masking moiety (MM2) such that coupling of the MM2 reduces the ability of the AB2 to binds the target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a target, where the AB2 is attached to a masking moiety (MM2) such that coupling of the MM2 reduces the ability of the AB2 to binds the target.

In some embodiments of an immune effector cell engaging multispecific activatable antibody, one antigen is the target, and another antigen is typically a stimulatory or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. In some embodiments, the antigen is a stimulatory receptor present on the surface of a T cell or NK cell; examples of such stimulatory receptors include, but are not limited to, CD3, CD27, CD28, CD137 (also referred to as 4-1BB), GITR, HVEM, ICOS, NKG2D, and OX40. In some embodiments, the antigen is an inhibitory receptor present on the surface of a T-cell; examples of such inhibitory receptors include, but are not limited to, BTLA, CTLA-4, LAG3, PD-1, TIGIT, TIM3, and NK-expressed KIRs. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PDL1, PDL2, or TNFSF9.

In some embodiments, the T-cell engaging multispecific activatable antibody includes an anti-CD3 epsilon (CD3ε, also referred to herein as CD3e and CD3) scFv and a targeting antibody or antigen-binding fragment thereof, where at least one of the anti-CD3ε scFv and/or the targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a target, where the AB2 is attached to a masking moiety (MM2) such that coupling of the MM2 reduces the ability of the AB2 to binds the target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a target, where the AB2 is attached to a masking moiety (MM2) such that coupling of the MM2 reduces the ability of the AB2 to binds the target.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In a multispecific activatable antibody, a scFv can be fused to the carboxyl terminus of the heavy chain of an IgG activatable antibody, to the carboxyl terminus of the light chain of an IgG activatable antibody, or to the carboxyl termini of both the heavy and light chains of an IgG activatable antibody. In a multispecific activatable antibody, a scFv can be fused to the amino terminus of the heavy chain of an IgG activatable antibody, to the amino terminus of the light chain of an IgG activatable antibody, or to the amino termini of both the heavy and light chains of an IgG activatable antibody. In a multispecific activatable antibody, a scFv can be fused to any combination of one or more carboxyl termini and one or more amino termini of an IgG activatable antibody. In some embodiments, a masking moiety (MM) linked to a cleavable moiety (CM) is attached to and masks an antigen binding domain of the IgG. In some embodiments, a masking moiety (MM) linked to a cleavable moiety (CM) is attached to and masks an antigen binding domain of at least one scFv. In some embodiments, a masking moiety (MM) linked to a cleavable moiety (CM) is attached to and masks an antigen binding domain of an IgG and a masking moiety (MM) linked to a cleavable moiety (CM) is attached to and masks an antigen binding domain of at least one scFv.

The disclosure provides examples of multispecific activatable antibody structures which include, but are not limited to, the following: (VL-CL)$_2$:(VH-CH1-CH2-CH3-L4-VH*-L3-VL*-L2-CM-L1-MM)$_2$; (VL-CL)$_2$: (VH-CH1-CH2-CH3-L4-VL*-L3-VH*-L2-CM-L1-MM)$_2$; (MM-L1-CM-L2-VL-CL)$_2$: (VH-CH1-CH2-CH3-L4-VH*-L3-VL*)$_2$; (MM-L1-CM-L2-VL-CL)$_2$: (VH-CH1-CH2-CH3-L4-VL*-L3-VH*)$_2$; (VL-CL)$_2$: (MM-L1-CM-L2-VL*-L3-VH*-L4-VH-CH1-CH2-CH3)$_2$; (VL-CL)$_2$: (MM-L1-CM-L2-VH*-L3-VL*-L4-VH-CH1-CH2-CH3)$_2$; (MM-L1-CM-L2-VL-CL)$_2$: (VL*-L3-VH*-L4-VH-CH1-CH2-CH3)$_2$; (MM-L1-CM-L2-VL-CL)$_2$:(VH*-L3-VL*-L4-VH-CH1-CH2-CH3)$_2$; (VL-CL-L4-VH*-L3-VL*-L2-CM-L1-MM)$_2$: (VH-CH1-CH2-CH3)$_2$; (VL-CL-L4-VL*-L3-VH*-L2-CM-L1-MM)$_2$:(VH-CH1-CH2-CH3)$_2$; (MM-L1-CM-L2-VL*-L3-VH*-L4-VL-CL)$_2$: (VH-CH1-CH2-CH3)$_2$; (MM-L1-CM-L2-VH*-L3-VL*-L4-VL-CL)$_2$: (VH-CH1-CH2-CH3)$_2$; (VL-CL-L4-VH*-L3-VL*-L2-CM-L1-MM)$_2$: (MM-L1-CM-L2-VL*-L3-VH*-L4-VH-CH1-CH2-CH3)$_2$; (VL-CL-L4-VH*-L3-VL*-L2-CM-L1-MM)$_2$: (MM-L1-CM-L2-VH*-L3-VL*-L4-VH-CH1-CH2-CH3)$_2$; (VL-CL-L4-VL*-L3-VH*-L2-CM-L1-MM)$_2$: (MM-L1-CM-L2-VL*-L3-VH*-L4-VH-CH1-CH2-CH3)$_2$; (VL-CL-L4-VL*-L3-VH*-L2-CM-L1-MM)$_2$: (MM-L1-CM-L2-VH*-L3-VL*-L4-VH-CH1-CH2-CH3)$_2$; (VL-CL-L4-VH*-L3-VL*)$_2$: (MM-L1-CM-L2-VL*-L3-VH*-L4-VH-CH1-CH2-CH3)$_2$; (VL-CL-L4-VH*-L3-VL*)$_2$: (MM-L1-CM-L2-VH*-L3-VL*-L4-VH-CH1-CH2-CH3)$_2$; (VL-CL-L4-VL*-L3-VH*)$_2$: (MM-L1-CM-L2-VL*-L3-VH*-L4-VH-CH1-CH2-CH3)$_2$; (VL-CL-L4-VL*-L3-VH*)$_2$: (MM-L1-CM-L2-VH*-L3-VL*-L4-VH-CH1-CH2-CH3)$_2$; (VL-CL-L4-VH*-L3-VL*-L2-CM-L1-MM)$_2$: (VL*-L3-VH*-L4-VH-CH1-CH2-CH3)$_2$; (VL-CL-L4-VH*-L3-VL*-L2-CM-L1-MM)$_2$: (VH*-L3-VL*-L4-VH-CH1-CH2-CH3)$_2$; (VL-CL-L4-VL*-L3-VH*-L2-CM-L1-MM)$_2$: (VL*-L3-VH*-L4-VH-CH1-CH2-CH3)$_2$; or (VL-CL-L4-VL*-L3-VH*-L2-CM-L1-MM)$_2$: (VH*-L3-VL*-L4-VH-CH1-CH2-CH3)$_2$, wherein: VL and VH represent the light and heavy variable domains of the first specificity, contained in the IgG; VL* and VH* represent the variable domains of the second specificity, contained in the scFv; L1 is a linker peptide connecting the masking moiety (MM) and the cleavable moiety (CM); L2 is a linker peptide connecting the cleavable moiety (CM), and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities can be toward any antigen or epitope.

In some embodiments of a T-cell engaging multispecific activatable antibody, one antigen is the target, and another antigen is typically a stimulatory (also referred to herein as activating) or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137 (also referred to as TNFRSF9), CTLA-4, GITR, HVEM, ICOS, LAG3, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor.

In some embodiments, the targeting antibody is an antibody disclosed herein. In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CD3ε, and comprises or is derived from an antibody or fragment thereof that binds CD3E, e.g., CH2527, FN18, H2C, OKT3, 2C11, UCHT1, or V9. In some embodiments, the scFv is specific for binding CTLA-4 (also referred to herein as CTLA and CTLA4).

In some embodiments, the anti-CTLA-4 scFv includes the amino acid sequence:

(SEQ ID NO: 643)

```
GGGSGGGGSGSGGGSGGGGSGGGEIVLTQSPGTLSLSPGERATLSCRASQ
SVSSSYLAWYQQKPGQAPRLLIYGASSRATGIPDRFSGSGSGTDFTLTIS
RLEPEDFAVYYCQQYGSSPLTFGGGTKVEIKRSGGSTITSYNVYYTKLSS
SGTQVQLVQTGGGVVQPGRSLRLSCAASGSTFSSYAMSWVRQAPGKGLEW
VSAISGSGGSTYYADSVKGRFTISRDNSKNTLYLQMNSLRAEDTAVYYCA
TNSLYWYFDLWGRGTLVTVSSAS
```

In some embodiments, the anti-CTLA-4 scFv includes the amino acid sequence that is at least 90%, 91%, 92%, 93%, 94%, 95%, 96%, 97%, 98%, 99% or more identical to the amino acid sequence of SEQ ID NO: 643.

In some embodiments, the anti-CD3ε scFv includes the amino acid sequence:

(SEQ ID NO: 644)

```
GGGSGGGGSGSGGGSGGGGSGGGQVQLQQSGAELARPGASVKMSCKASGY
TFTRYTMHWVKQRPGQGLEWIGYINPSRGYTNYNQKFKDKATLTTDKSSS
TAYMQLSSLTSEDSAVYYCARYYDDHYCLDYWGQGTTLTVSSGGGGSGGG
GSGGGGSQIVLTQSPAIMSASPGEKVTMTCSASSSVSYMNWYQQKSGTSP
KRWIYDTSKLASGVPAHFRGSGSGTSYSLTISGMEAEDAATYYCQQWSSN
PFTFGSGTKLEINR
```

In some embodiments, the anti-CD3ε scFv includes the amino acid sequence that is at least 90%, 91%, 92%, 93%, 94%, 95%, 96%, 97%, 98%, 99% or more identical to the amino acid sequence of SEQ ID NO: 644.

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA.

In some embodiments, the multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the multispecific activatable antibody via a linker. In some embodiments, the agent is conjugated to the AB via a cleavable linker. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 5. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the multispecific activatable antibody also includes a detectable moiety. In some embodiments, the detectable moiety is a diagnostic agent.

In some embodiments, the multispecific activatable antibody naturally contains one or more disulfide bonds. In some embodiments, the multispecific activatable antibody can be engineered to include one or more disulfide bonds.

The disclosure also provides an isolated nucleic acid molecule encoding a multispecific activatable antibody described herein, as well as vectors that include these isolated nucleic acid sequences. The disclosure provides methods of producing a multispecific activatable antibody by culturing a cell under conditions that lead to expression of the activatable antibody, wherein the cell comprises such a nucleic acid molecule. In some embodiments, the cell comprises such a vector.

The disclosure also provides a method of manufacturing multispecific activatable antibodies of the disclosure by (a) culturing a cell comprising a nucleic acid construct that encodes the multispecific activatable antibody under conditions that lead to expression of the multispecific activatable, and (b) recovering the multispecific activatable antibody. Suitable AB, MM, and/or CM include any of the AB, MM, and/or CM disclosed herein.

The disclosure also provides multispecific activatable antibodies and/or multispecific activatable antibody compositions that include at least a first antibody or antigen-binding fragment thereof (AB1) that specifically binds a first target or first epitope and a second antibody or antigen-biding fragment thereof (AB2) that binds a second target or a second epitope, where at least AB1 is coupled or otherwise attached to a masking moiety (MM1), such that coupling of the MM1 reduces the ability of AB1 to bind its target. In some embodiments, the MM1 is coupled to AB1 via a first cleavable moiety (CM1) sequence that includes a substrate for a protease, for example, a protease that is co-localized with the target of AB1 at a treatment site or a diagnostic site in a subject. The multispecific activatable antibodies provided herein are stable in circulation, activated at intended sites of therapy and/or diagnosis but not in normal, i.e., healthy tissue, and, when activated, exhibit binding to the target of AB1 that is at least comparable to the corresponding, unmodified multispecific antibody. Suitable AB, MM, and/or CM include any of the AB, MM, and/or CM disclosed herein.

The disclosure also provides compositions and methods that include a multispecific activatable antibody that includes at least a first antibody or antibody fragment (AB1) that specifically binds a target and a second antibody or antibody fragment (AB2), where at least the first AB in the multispecific activatable antibody is coupled to a masking moiety (MM1) that decreases the ability of AB1 to bind its target. In some embodiments, each AB is coupled to a MM that decreases the ability of its corresponding AB to each target. For example, in bispecific activatable antibody embodiments, AB1 is coupled to a first masking moiety (MM1) that decreases the ability of AB1 to bind its target, and AB2 is coupled to a second masking moiety (MM2) that decreases the ability of AB2 to bind its target. In some embodiments, the multispecific activatable antibody comprises more than two AB regions; in such embodiments, AB1 is coupled to a first masking moiety (MM1) that decreases the ability of AB1 to bind its target, AB2 is coupled to a second masking moiety (MM2) that decreases the ability of AB2 to bind its target, AB3 is coupled to a third masking moiety (MM3) that decreases the ability of AB3 to bind its target, and so on for each AB in the multispecific activatable antibody. Suitable AB, MM, and/or CM include any of the AB, MM, and/or CM disclosed herein.

In some embodiments, the multispecific activatable antibody further includes at least one cleavable moiety (CM) that is a substrate for a protease, where the CM links a MM to an AB. For example, in some embodiments, the multispecific activatable antibody includes at least a first antibody or antibody fragment (AB1) that specifically binds a target and a second antibody or antibody fragment (AB2), where at least the first AB in the multispecific activatable antibody is coupled via a first cleavable moiety (CM1) to a masking moiety (MM1) that decreases the ability of AB1 to bind its target. In some bispecific activatable antibody embodiments, AB1 is coupled via CM1 to MM1, and AB2 is coupled via a second cleavable moiety (CM2) to a second masking moiety (MM2) that decreases the ability of AB2 to bind its target. In some embodiments, the multispecific activatable antibody comprises more than two AB regions; in some of these embodiments, AB1 is coupled via CM1 to MM1, AB2 is coupled via CM2 to MM2, and AB3 is coupled via a third cleavable moiety (CM3) to a third masking moiety (MM3) that decreases the ability of AB3 to bind its target, and so on for each AB in the multispecific activatable antibody. Suitable AB, MM, and/or CM include any of the AB, MM, and/or CM disclosed herein.

Activatable antibodies Having Non-Binding Steric Moieties or Binding Partners for Non-Binding Steric Moieties In some embodiment, the compositions and methods provided herein are used with activatable antibodies that include non-binding steric moieties (NB) or binding partners (BP) for non-binding steric moieties, where the BP recruits or otherwise attracts the NB to the activatable antibody. The activatable antibodies provided herein include, for example, an activatable antibody that includes a non-binding steric moiety (NB), a cleavable linker (CL) and antibody or antibody fragment (AB) that binds a target; an activatable antibody that includes a binding partner for a non-binding steric moiety (BP), a CL and an AB; and an activatable antibody that includes a BP to which an NB has been recruited, a CL and an AB that binds the target. Activatable antibodies in which the NB is covalently linked to the CL and AB of the activatable antibody or is associated by interaction with a BP that is covalently linked to the CL and AB of the activatable antibody are referred to herein as "NB-containing activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the at non-treatment sites and/or non-diagnostic sites if the AB were not masked or otherwise inhibited from binding to such a site.

Activatable antibodies that include a non-binding steric moiety (NB) can be made using the methods set forth in PCT Publication No. WO 2013/192546, the contents of which are hereby incorporated by reference in their entirety.

Embodiments of the invention include the following:

1. A method of quantitating a level of activation of an activatable antibody-based therapeutic, the method comprising:

i) loading at least one capillary or a population of capillaries with a stacking matrix and a separation matrix;

ii) contacting the loaded capillary or population of loaded capillaries with a biological sample;

iii) separating high molecular weight (MW) components of the biological sample from low molecular weight (MW) components of the biological sample within each capillary;

iv) immobilizing the high MW components and the low MW components within each capillary;

v) immunoprobing each capillary with at least one detectable reagent that is specific for at least one activatable antibody, conjugated activatable antibody, multispecific activatable antibody, conjugated multispecific activatable antibody, or combination thereof; and vi) quantitating a level of detectable reagent in each capillary or population of capillaries.

2. The method of embodiment 1, wherein the at least one detectable reagent in step v) comprises at least a first reagent that is specific for at least one activatable antibody, conjugated activatable antibody, multispecific activatable antibody, conjugated multispecific activatable antibody, or combination thereof and a second reagent that specifically binds to or recognizes the first reagent, wherein the second reagent comprises a detectable label.

3. The method of embodiment 2, wherein step vi) comprises quantitating a level of detectable label in each capillary or population of capillaries.

4. The method of any one of embodiments 1 to 3, wherein step ii) comprises loading approximately 1-500 ng of biological sample.

5. The method of any one of embodiments 1 to 4, wherein step ii) comprises loading approximately 5-40 ng of biological sample.

6. The method of any one of embodiments 1 to 5, wherein the biological sample is prepared using one or more SDS-containing buffers in an amount sufficient to result in molecular weight separation.

7. The method of any one of embodiments 1 to 6, wherein step iv) comprises using UV light to immobilize the high MW components and the low MW components of the biological sample.

8. The method of any one of embodiments 1 to 7, wherein the first reagent in step v) is an antibody or antigen-binding fragment thereof that specifically binds to at least one activatable antibody, conjugated activatable antibody, multispecific activatable antibody, conjugated multispecific activatable antibody, or combination thereof.

9. The method of any one of embodiments 1 to 8, wherein the second reagent in step v) is a detectably labeled secondary antibody that specifically binds to the first reagent.

10. The method of any one of embodiments to 1 to 7, wherein the first reagent in step v) is a primary antibody or antigen-binding fragment thereof that specifically binds to at least one activatable antibody, conjugated activatable antibody, multispecific activatable antibody, conjugated multispecific activatable antibody, or combination thereof, and the second reagent in step v) is a detectably labeled secondary antibody that specifically binds to the primary antibody or antigen-binding fragment thereof.

11. The method of any one of embodiments 1 to 10, wherein the detectable label is conjugated to the second reagent.

12. The method of embodiment 11, wherein the detectable label is a fluorescent label, and step vi) comprises detecting a level of chemiluminescence in each capillary or population of capillaries.

13. The method of embodiment 12, wherein the detectable label is horseradish peroxidase (HRP).

14. The method of any one of embodiments 1 to 13, wherein the biological sample is a bodily fluid.

15. The method of embodiment 14, wherein the bodily fluid is blood, plasma, or serum.

16. The method of any one of embodiments 1 to 13, wherein the biological sample is a diseased tissue.

17. The method of embodiment 16, wherein the diseased tissue is a lysate.

18. The method of embodiment 16 or embodiment 17, wherein the disease tissue is tumor tissue.

19. The method of any of embodiments 1-18, wherein the method compares amounts of activated and intact activatable antibody or activatable antibody-based therapeutics.

20. The method of embodiment 19, wherein the activatable antibody-based therapeutic is a conjugated activatable antibody, a multispecific activatable antibody, a conjugated multispecific activatable antibody, or any combination thereof.

21. An isolated antibody or antigen-binding fragment thereof comprising a variable heavy chain complementarity determining region 1 (CDRH1) comprising the amino acid sequence SYGMS (SEQ ID NO: 438); a variable heavy chain complementarity determining region 2 (CDRH2) comprising the amino acid sequence TISPSGIYTYYPVTVKG (SEQ ID NO: 439); a variable heavy chain complementarity determining region 3

(CDRH3) comprising the amino acid sequence HHPNYGSTYLYYIDY (SEQ ID NO: 440); a variable light chain complementarity determining region 1 (CDRL1) comprising the amino acid sequence KSSQSVFSSSNQKNYLA (SEQ ID NO: 441); a variable light chain complementarity determining region 2 (CDRL2) comprising the amino acid sequence WAFTRES (SEQ ID NO: 442); and a variable light chain complementarity determining region 3 (CDRL3) comprising the amino acid sequence YQYLSSLT (SEQ ID NO: 443).

22. The antibody or antigen-binding fragment thereof of embodiment 21, wherein the antibody or antigen-binding fragment thereof comprises a variable heavy chain comprising the amino acid sequence of SEQ ID NO: 429.

23. The antibody or antigen-binding fragment thereof of embodiment 21 or embodiment 22, wherein the antibody or antigen-binding fragment thereof comprises a variable light chain comprising the amino acid sequence of SEQ ID NO: 431.

24. An isolated antibody or antigen-binding fragment thereof comprising a variable heavy chain comprising the amino acid sequence of SEQ ID NO: 429.

25. The isolated antibody or antigen-binding fragment thereof of embodiment 24 comprising a variable light chain comprising the amino acid sequence of SEQ ID NO: 431.

26. An isolated antibody or antigen-binding fragment thereof comprising a variable light chain comprising the amino acid sequence of SEQ ID NO: 431.

27. The isolated antibody or antigen-binding fragment thereof of embodiment 26 comprising a variable heavy chain comprising the amino acid sequence of SEQ ID NO: 429.

The invention will be further described in the following examples, which do not limit the scope of the invention described in the claims.

EXAMPLES

Example 1. Generation of Antibodies that Bind Activated and Intact Anti-PDL1 Activatable Antibodies The studies provided herein were designed to generate and evaluate antibodies that bind anti-PDL1 activatable antibodies of the disclosure.

The studies presented herein used the anti-PDL1 activatable antibody referred to herein as PL07-2001-C5H9v2, which comprises the heavy chain sequence of SEQ ID NO: 425 and the light chain sequence of SEQ ID NO: 426, as shown below.

```
PL07-2001-C5H9v2 Heavy Chain Amino Acid Sequence
                                        (SEQ ID NO: 425)
EVQLLESGGGLVQPGGSLRLSCAASGFTFSSYAMSWVRQAPGKGLEWVSS

IWRNGIVTVYADSVKGRFTISRDNSKNTLYLQMNSLRAEDTAVYYCAKWS

AAFDYWGQGTLVTVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS
```

-continued

```
QEEMTKNQVSLTCLVKGFYPSDIAVEWESNGQPENNYKTTPPVLDSDGSF

FLYSRLTVDKSRWQEGNVFSCSVMHEALHNHYTQKSLSLSLG

PL07-2001-C5H9v2 Light Chain Amino Acid Sequence
                                        (SEQ ID NO: 426)
QGQSGSGIALCPSHFCQLPQTGGGSSGGSGGSGGISSGLLSGRSDNHGGS

DIQMTQSPSSLSASVGDRVTITCRASQSISSYLNWYQQKPGKAPKLLIYA

ASSLQSGVPSRFSGSGSGTDFTLTISSLQPEDFATYYCQQDNGYPSTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Mice were immunized by GenScript Biotech Corporation with peptide antigen CQQDNGYPSTFGGGT (SEQ ID NO: 427), comprising the VL CDR3 of anti-PDL1 activatable antibody PL07-2001-C5H9v2, that was conjugated to the carrier protein Keyhole Limpet Hemocyanin (KLH) using the procedure shown below in Table 3. Six three-month old (3 Balb/c and 3 C56) mice were immunized according to the protocol listed below. At the time of each injection, the antigen aliquot was thawed and combined with Complete Freund's Adjuvant (CFA) for the first injection or with incomplete Freund's Adjuvant (IFA) for subsequent injections.

TABLE 3

Immunization Schedule

| Procedure | Schedule | Dosage and route |
|---|---|---|
| Pre-Immune Bleed | T = −4 days | |
| Primary immunization | T = 0 days | 50 μg/animal, s.c |
| Boost 1 | T = 14 days | 25 μg/animal, s.c |
| Test Bleed 1 | T = 21 days | |
| Boost 2 | T = 28 days | 25 μg/animal, s.c |
| Test Bleed 2 | T = 35 days | |
| Final Boost | T = 50 ± 7 days | 25 μg/animal, i.v. |
| Cell Fusion | 4 days after final boost | |

Serum titers against the free peptide as well as counter screen antigen (human IgG) were evaluated in test bleeds using a standard ELISA procedure. Leads were evaluated against full length activatable antibody in human plasma by Western blot. The results indicated that all mice had comparable titers against the respective immunogen. Antisera were tested against activatable antibody PL07-2001-C5H9v2 on the Wes™ system (ProteinSimple), and two mice were chosen for cell fusion.

Mouse monoclonal antibodies were generated as follows: Lymphocytes from the two mice were used for hybridoma fusion and plated on forty 96-well plates (400 million lymphocytes per mouse). The plates were kept in tissue culture incubators under standard conditions.

Example 2. Screening of Hybridoma Clones and Antibody Characterization

This Example describes the screening and characterization of hybridoma clones and resultant antibodies generated against anti-PDL1 activatable antibody PL07-2001-C5H9v2.

Figure 1B:
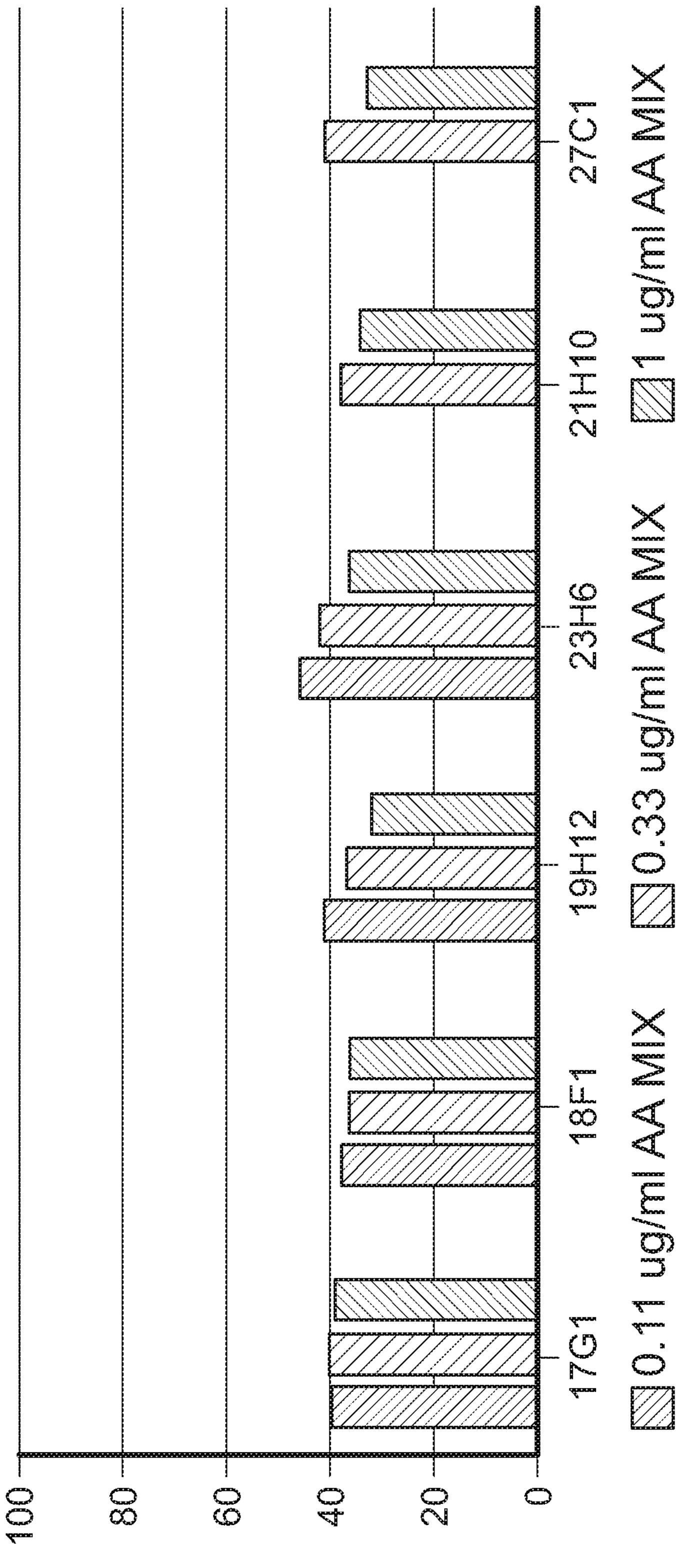

Hybridoma supernatant from parental clones were screened by GenScript against a short peptide containing the VL CDR3 of activatable antibody PL07-2001-C5H9v2 by indirect ELISA. Briefly, GenScript high binding plates were coated with peptide-BSA at 1 ug/mL concentration, 100 uL/well. Supernatant was used without dilution. Anti-serum at 1:1000 dilution was used as positive control. Peroxidase-AffiniPure Goat Anti-Mouse IgG, Fcγ Fragment Specific (minimum cross-reactive with human, bovine or horse serum albumin, also referred to as min X Hu,Bov,Hrs Sr Prot) was used as secondary. Twenty clones with positive signals were further screened against anti-PDL1 antibody C5H9v2, the parental antibody of activatable antibody PL07-2001-C5H9v2, and 5 ug/mL of human IgG. Anti-PDL1 antibody C5H9v2 was coated onto high binding plates at 1 ug/mL concentration, 100 uL/well. Human IgG was coated onto high-binding plates at 5 ug/mL concentration, 100 uL/well. Western blot analysis was also performed on these 20 clones using 200 ng of denatured and reduced anti-PDL1 antibody C5H9v2 as target. As a final screen, supernatants from the 20 clones were also assessed on the Wes™ system (ProteinSimple). Briefly, all 20 clones were tested against 1 ug/mL of one-arm activated activatable antibody PL07-2001-C5H9v2 in 0.1× sample buffer and 1 ug/mL of one-arm activated activatable antibody PL07-2001-C5H9v2 in 1:100 human plasma. The top 6 clones as assessed by intensity and specificity of binding to activatable antibody PL07-2001-C5H9v2, referred to as 17G1, 18F1, 19H12, and 23H6, 21H10 and 27C1, were further screened against one-arm activated activatable antibody PL07-2001-C5H9v2 at 0.11 and 0.33 ug/mL concentrations in 1:100 human plasma. Results are shown in FIG. 1A and FIG. 1B, which shows screening of activatable antibody PL07-2001-C5H9v2 anti-idiotypic (anti-id) clones against 37% one-arm activated activatable antibody PL07-2001-C5H9v2 at 0.11, 0.33 and 1 ug/ml in human plasma at 1:100. FIG. 1A is an electropherogram showing 17G1 detection of decreasing concentrations of one-arm activated activatable antibody PL07-2001-C5H9v2 (1, 0.33, and 0.11 ug/ml). FIG. 1B portrays the relative activation percent for the top 6 clones of one-arm activated activatable antibody PL07-2001-C5H9v2. The relative activation rate is preserved at different concentrations. Clones 21H10 and 27C1 have lower affinity resulting in no data for the 0.11 ug/ml concentration.

Clones 17G1, 18F1, 19H12, and 23H6 were selected for subcloning and characterization. Molecular cloning was performed using the following method. Total RNA was isolated from the fresh hybridoma cells recovered by GenScript following the techniques described in the TRIzol® Reagent technical manual (ThermoFisher). Total RNA was then reverse-transcribed into cDNA using either isotype-specific anti-sense primers or universal primers following the techniques described in the PrimeScript™ 1st Strand cDNA Synthesis Kit (Clontech). Variable heavy (VH), variable light (VL), heavy chain (HC) and light chain (LC) antibody fragments were amplified according to GenScript's rapid amplification of cDNA ends (RACE) protocol. Each of the amplified antibody fragments were cloned into separate standard cloning vectors. Colony PCR was performed to screen for clones with inserts of correct sizes. No less than five colonies with inserts of correct sizes were sequenced for each fragment. The sequences of different clones were aligned and the consensus sequence was determined.

The nucleic and amino acid sequences of antibody 17G1 are provided below. The 17G1 antibody includes a variable heavy chain complementarity determining region 1 (CDRH1) comprising the amino acid sequence SYGMS (SEQ ID NO: 438); a variable heavy chain complementarity determining region 2 (CDRH2) comprising the amino acid sequence TISPSGIYTYYPVTVKG (SEQ ID NO: 439); a variable heavy chain complementarity determining region 3 (CDRH3) comprising the amino acid sequence HHPNYGSTYLYYIDY (SEQ ID NO: 440); a variable light chain complementarity determining region 1 (CDRL1) comprising the amino acid sequence KSSQSVFSSSNQKNYLA (SEQ ID NO: 441); a variable light chain complementarity determining region 2 (CDRL2) comprising the amino acid sequence WAFTRES (SEQ ID NO: 442); and a variable light chain complementarity determining region 3 (CDRL3) comprising the amino acid sequence YQYLSSLT (SEQ ID NO: 443).

```
Mature Variable Heavy Region: DNA sequence
[FR1]-[CDR1]-[FR2]-[CDR2]-[FR3]-[CDR3]-[FR4]
                                        (SEQ ID NO: 428)
[GAGGTGCAGTTGGTGGAGTCTGGGGGAGACTTAGTGAAGCCTGGAGGG

TCCCTGAAAGTCTCCTGTGCAGCCTCTGGATTCACTTTCAGT][AGTTA

TGGCATGTCT][TGGGTTCGCCAGACTCCAGACAAAAGGCTGGAGTGGG

TCGCA][ACCATTAGTCCTAGTGGTATATACACCTACTATCCAGTCACT

GTGAAGGGG][CGATTCACCATCTCCAGAGACAATGCCAAGAACACCCT

GTACCTGCAAATGAGCAGTCTGAAGTCTGAGGACACAGCCATGTATTTC

TGTGCAAGA][CACCATCCAAACTATGGTAGTACGTACCTGTATTATAT

TGATTAC][TGGGGCCAAGGCACCGCTCTCACAGTCTCCTCA]

Mature Variable Heavy Region: Amino acid sequence
[FR1]-[CDR1]-[FR2]-[CDR2]-[FR3]-[CDR3]-[FR4]
                                        (SEQ ID NO: 429)
[EVQLVESGGDLVKPGGSLKVSCAASGFTFS][SYGMS][WVRQTPDKR

LEWVA][TISPSGIYTYYPVTVKG][RFTISRDNAKNTLYLQMSSLKSE

DTAMYFCAR]

Mature Heavy Chain: Amino acid sequence: 17G1_
Hc mIgG2a
                                        (SEQ ID NO: 444)
EVQLVESGGDLVKPGGSLKVSCAASGFTFSSYGMSWVRQTPDKRLEWVA

TISPSGIYTYYPVTVKGRFTISRDNAKNTLYLQMSSLKSEDTAMYFCAR

HHPNYGSTYLYYIDYWGQGTALTVSSAKTTAPSVYPLAPVCGDTTGSSV

TLGCLVKGYFPEPVTLTWNSGSLSSGVHTFPAVLQSDLYTLSSSVTVTS

STWPSQSITCNVAHPASSTKVDKKIEPRGPTIKPCPPCKCPAPNLLGGP

SVFIFPPKIKDVLMISLSPIVTCVVVDVSEDDPDVQISWFVNNVEVHTA

QTQTHREDYNSTLRVVSALPIQHQDWMSGKEFKCKVNNKDLPAPIERTI

SKPKGSVRAPQVYVLPPPEEEMTKKQVTLTCMVTDFMPEDIYVEWTNNG

KTELNYKNTEPVLDSDGSYFMYSKLRVEKKNWVERNSYSCSVVHEGLHN

HHTTKSFSRTPGK

Mature Variable Light Region: DNA sequence
[FR1]-[CDR1]-[FR2]-[CDR2]-[FR3]-[CDR3]-[FR4]
                                        (SEQ ID NO: 430)
[AACATTATGATGACACAGTCGCCATCATCTCTGGCTGTGTCTGCAGGA

GAAAAGGTCACTATGGCCTGT][AAGTCCAGTCAAAGTGTTTTTTCCAG

TTCAAATCAGAAGAACTACTTGGCC][TGGTACCAGCAGAAACCAGGGC

AGTCTCCTAAAATACTGATCTAC][TGGGCTTTCACTAGGGAATCT][G

GTGTCCCTGACCGCTTCTCAGGCAGTGGATCTGGGACAGATTTTACTCT

TACCATCAGCAGTGTGCAAGCTGAAGACCTGGCAGTTTATTACTGT][T

ATCAATACCTCTCCTCACTCACG][TTCGGTGCTGGGACCAAGCTGGAG

GTGAAA]
```

-continued

```
Mature Variable Light Region: Amino acid sequence
[FR1]-[CDR1]-[FR2]-[CDR2]-[FR3]-[CDR3]-[FR4]
                                       (SEQ ID NO: 431)
[NIMMTQSPSSLAVSAGEKVTMAC][KSSQSVFSSSNQKNYLA][WYQQ

KPGQSPKILIY][WAFTRES][GVPDRFSGSGSGTDFTLTISSVQAEDL

AVYYC][YQYLSSLT][FGAGTKLEVK]

Mature Light chain: Amino acid sequence: 17G1_
Lc mk
                                       (SEQ ID NO: 445)
NIMMTQSPSSLAVSAGEKVTMACKSSQSVFSSSNQKNYLAWYQQKPGQS

PKILIYWAFTRESGVPDRFSGSGSGTDFTLTISSVQAEDLAVYYCYQYL

SSLTFGAGTKLEVKADAAPTVSIFPPSSEQLTSGGASVVCFLNNFYPKD

INVKWKIDGSERQNGVLNSWTDQDSKDSTYSMSSTLTLTKDEYERHNSY

TCEATHKTSTSPIVKSFNRNEC
```

Example 3. Binding Specificity of Antibodies that Bind Anti-PDL1 Activatable Antibody This Example describes the ability of antibodies of the disclosure to bind anti-PDL1 activatable antibody PL07-2001-C5H9v2.

Figures 2A, 2B, 2C, 2D:
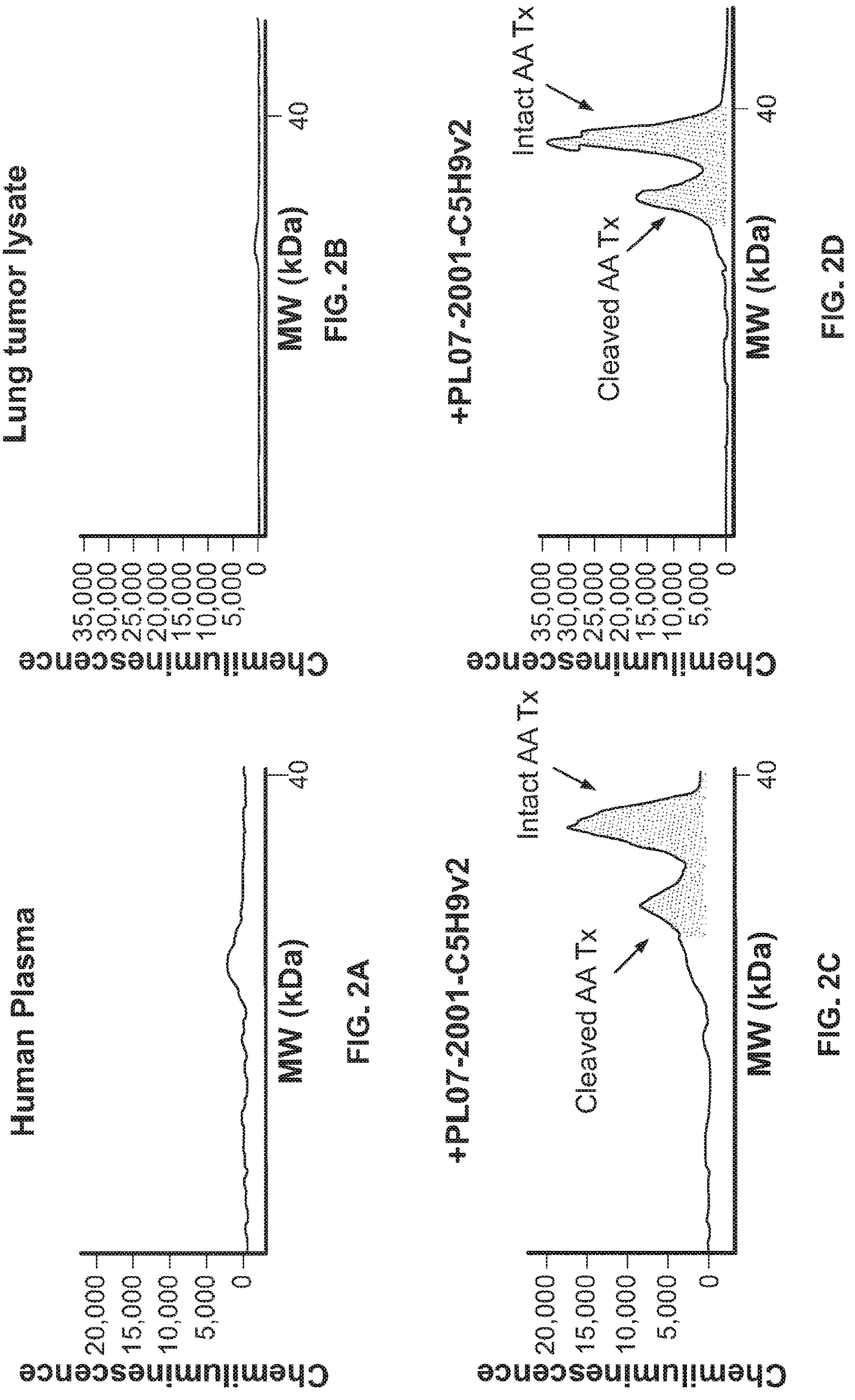
FIGS. 2A, 2B, 2C, and 2D are a series of graphs depicting that the antibody referred to herein as 17G1 has high specificity to the activatable antibody (AA) PL07-2001-C5H9v2. 17G1 was assessed on the Wes for specificity by spiking 160 ng/ml of one arm activated PL07-2001-C5H9v2 (activated AA) into either human plasma (FIG. 2C) or lung tumor lysates (FIG. 2D).

To test for specificity of antibody 17G1 binding to anti-PDL1 activatable antibody PL07-2001-C5H9v2, 160 ng/mL of one-arm activated anti-PDL1 activatable antibody PL07-2001-C5H9v2 were spiked into either human plasma (1 to 100 dilution in PBS) or lung tumor lysate. Briefly, tumor homogenates were prepared in Thermo Scientific Pierce™ IP Lysis Buffer (Catalog #87788) with added Thermo Scientific Halt™ Protease Inhibitor Single Use Cocktail Kit (Catalog #78430) using Barocycler (Pressure Biosciences). Anti-id antibody 17G1 was also tested against the same plasma and tumor that were not spiked with one-arm activated anti-PDL1 activatable antibody PL07-2001-C5H9v2. An HRP-conjugated anti-mouse secondary antibody was used in conjunction with luminol and peroxide and chemiluminescence was measured. The test samples were then analyzed on the Wes™ capillary electrophoresis immunoassay system (ProteinSimple), wherein separation was effected by SDS-based electrophoresis, also referred to as the Wes™ system. FIGS. 2A-2D demonstrate high binding specificity of antibody 17G1 to anti-PDL1 activatable antibody PL07-2001-C5H9v2 spiked into human plasma (FIG. 2C) and lung tumor lysate samples (FIG. 2D). FIGS. 2A and 2B demonstrate background binding of antibody 17G1 in human plasma and lung tumor lysate samples, respectively, in the absence of anti-PDL1 activatable antibody PL07-2001-C5H9v2.

Example 4. Quantification of Activated and Intact Anti-PDL1 Activatable Antibodies in Biological Samples This Example describes the ability of anti-id antibody 17G1 to detect activated and intact anti-PDL1 activatable antibody PL07-2001-C5H9v2 in plasma and xenograft tumor samples of mice administered anti-PDL1 activatable antibody PL07-2001-C5H9v2.

Anti-PDL1 activatable antibody PL07-2001-C5H9v2 is designed to be cleaved (i.e., activated) by a number of serine proteases and matrix metalloproteinases (MMPs) which are generally associated with human tumors (LeBeau et al, Imaging a functional tumorigenic biomarker in the transformed epithelium. Proc Natl Acad Sci 2013; 110: 93-98; Overall & Kleifeld, 2006, Validating Matrix Metalloproteinases as Drug Targets and Anti-Targets for Cancer Therapy. Nature Review Cancer, 6, 227-239), and which have low activity in blood or in normal tissues. To evaluate and measure activatable antibody activation in tumor and plasma samples, samples were analyzed by the Wes™ system that enables detection of intact and activated anti-PDL1 activatable antibody PL07-2001-C5H9v2 in the methods described herein. Using this system, it was shown that the activatable antibodies remain mostly intact (i.e., inactivated) in circulation, but are activated in mouse xenograft tumors.

In general, the following protocol was used: a mouse xenograft tumor model was developed by SC implantation of $3\times10^6$ MDA-MB-231-luc2-4D3LN cells in 30 uL serum-free medium containing matrigel (1:1) to 7-8 weeks old female nude mice. Body weights and tumor measurements were measured and recorded twice weekly for the duration of the study. After tumors achieved volume of 200-500 $mm^3$, mice were randomized into 3 groups of equivalent average tumor volume and dosed with anti-PDL1 activatable antibody PL07-2001-C5H9v2. Four days after treatment, tumor and plasma (heparin) were collected and stored at −80° C. prior to analysis. Tumor homogenates (i.e., lysates) were prepared in Thermo Scientific Pierce™ IP Lysis Buffer (Catalog #87788) with added Thermo Scientific Halt™ Protease Inhibitor Single Use Cocktail Kit (Catalog #78430) using Barocycler (Pressure Biosciences). Approximately 0.8 mg/mL of protein lysate in IP lysis buffer with HALT protease inhibitor/EDTA and plasma samples diluted 1 in 100 in PBS were analyzed by the Wes™ system as described herein.

Sample analysis was carried out in accordance with the methods described herein using the Wes™ capillary electrophoresis platform (ProteinSimple). See, the Simple Western Size Assay Development Guide (the world wide web at proteinsimple.com/documents/042-889_Rev1_Size_Assay_Development_Guide.pdf. In some embodiments, varying any one more of the following using the methods can be used to facilitate separate of intact and activated species: varying, e.g., increasing or decreasing, stacking time, varying, e.g., increasing or decreasing, sample time, and/or varying, e.g., increasing or decreasing, separation time.

In general, one part (e.g., 1 μL) 5× Fluorescent Master Mix (ProteinSimple) was combined with 4 parts (e.g., 4 μL) lysate to be tested in a microcentrifuge tube. A 1 ng to 5 ug range of anti-PDL1 activatable antibody PL07-2001-C5H9v2 was used for antibody screening and characterization. For biological samples comprising tumor tissue, 0.8 mg/mL of protein lysate in IP lysis buffer with HALT protease inhibitor/EDTA was used. Plasma samples were diluted 1 in 100 in PBS. Primary antibodies were used at a concentration of 1.7 ng/mL (diluted in Antibody diluent 2 (ProteinSimple Cat # 042-203). HRP-conjugated mouse secondary antibody (ProteinSimple) was used neat, in conjunction with luminol and peroxide and chemiluminescence was measured. Plates with samples prepared according to the Simple Western Size Assay Development Guide were centrifuged for 5 minutes at 2500 rpm (~1000× g) at room temperature before analyzing on the Wes™ system (ProteinSimple).

Figure 3A:
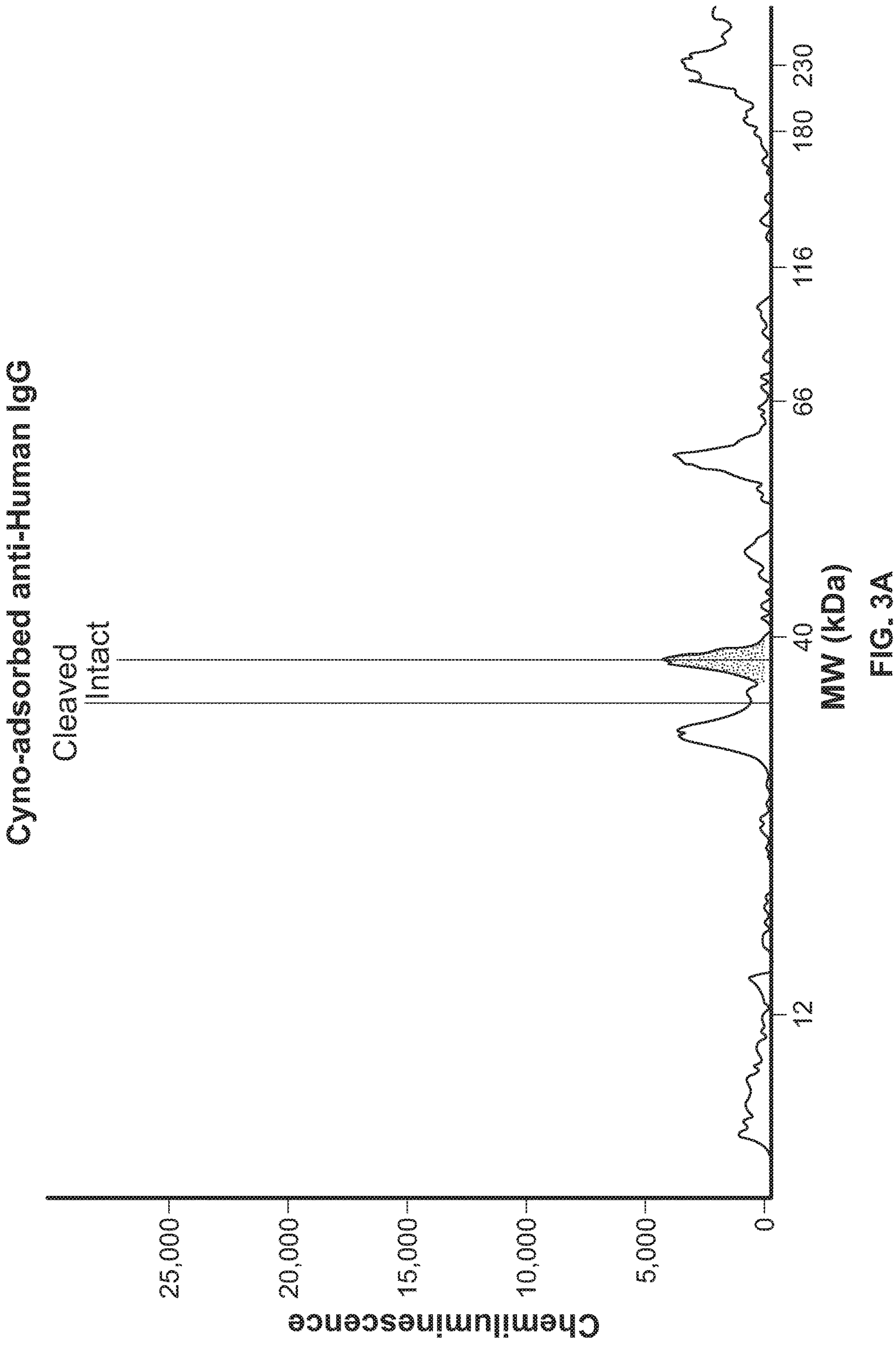
FIGS. 3A and 3B are a series of graphs depicting specific detection of activatable antibody (AA) therapeutics by selective anti-idiotypic antibodies.
Figure 3B:
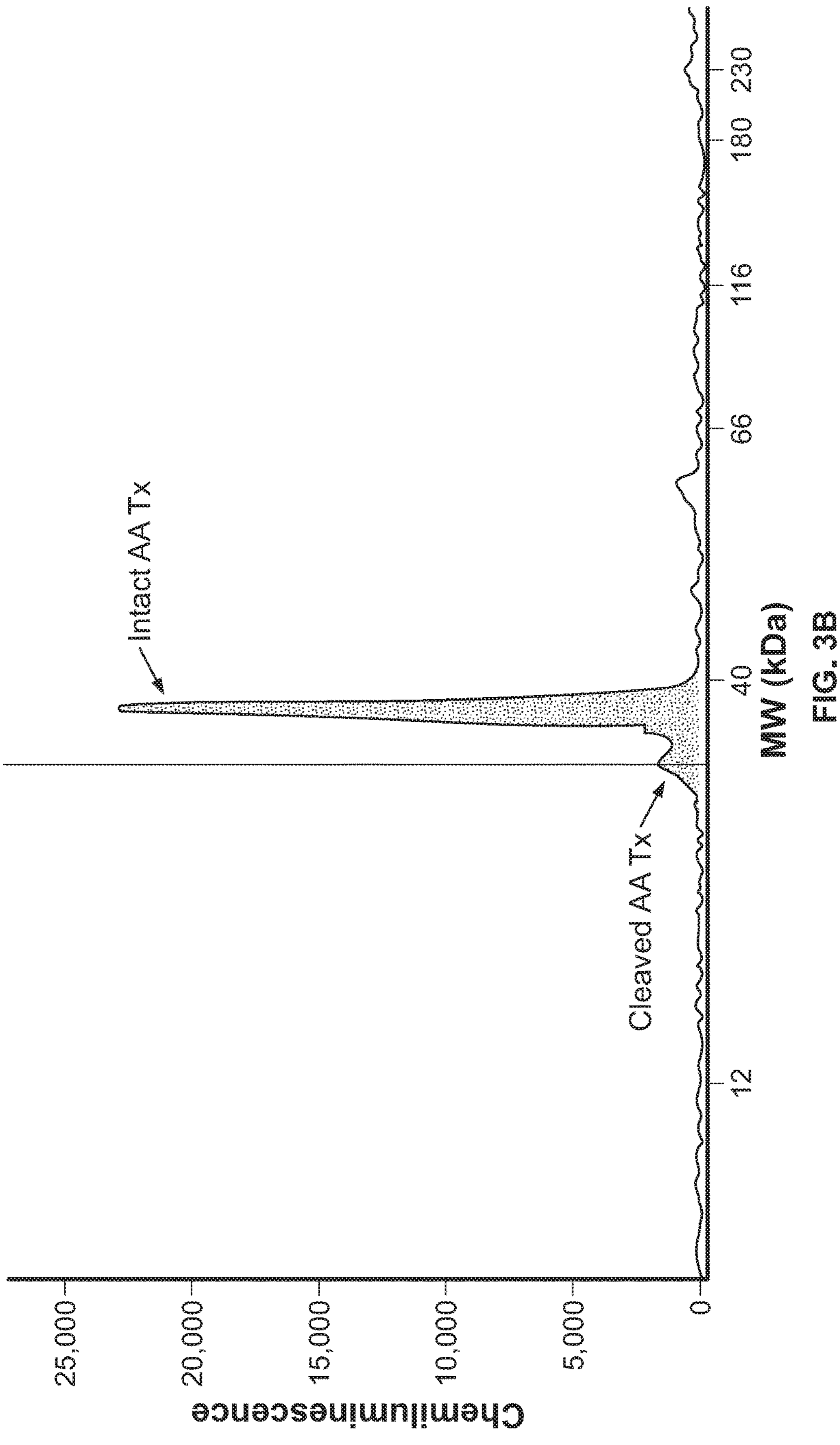

FIGS. 3A and 3B compare specific detection of intact and activated anti-PDL1 activatable antibody PL07-2001-C5H9v2 by anti-idiotypic antibody 17G1 of the disclosure and commercial anti-human IgG A110IJK (cynomolgus monkey adsorbed goat anti-human IgG) from American Qualex. Anti-id antibody 17G1 of the disclosure was able to detect anti-PDL1 activatable antibody PL07-2001-C5H9v2 in plasma of mice treated with only 0.1 mg/kg of anti-PDL1 activatable antibody PL07-2001-C5H9v2 (FIG. 3B) as compared to the commercial human IgG antibody only being able to minimally detect anti-PDL1 activatable antibody PL07-2001-C5H9v2 in plasma of mice treated with 10 mg/kg anti-PDL1 activatable antibody PL07-2001-C5H9v2 (FIG. 3A).

Figure 4B:
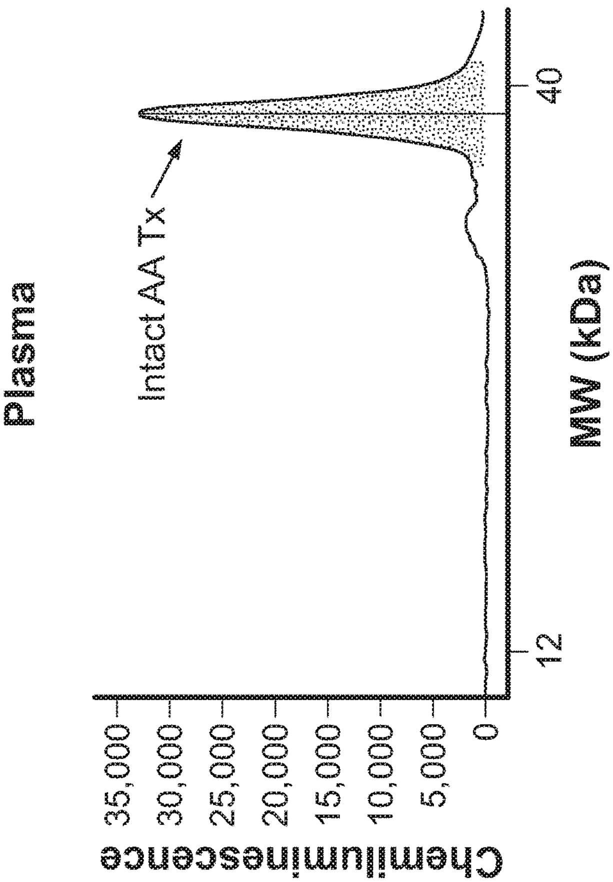
FIG. 4A and FIG. 4B are a series of graphs depicting preferential activation of activatable antibody (AA) therapeutics in tumor versus plasma detected in xenograft tumor model. MDA-MB-231 xenograft mice were treated with 1 mg/ml of the anti-PDL1 activatable antibody referred to herein as PL07-2001-C5H9v2. Tumor and plasma samples were collected on day 4.
Figure 4A:
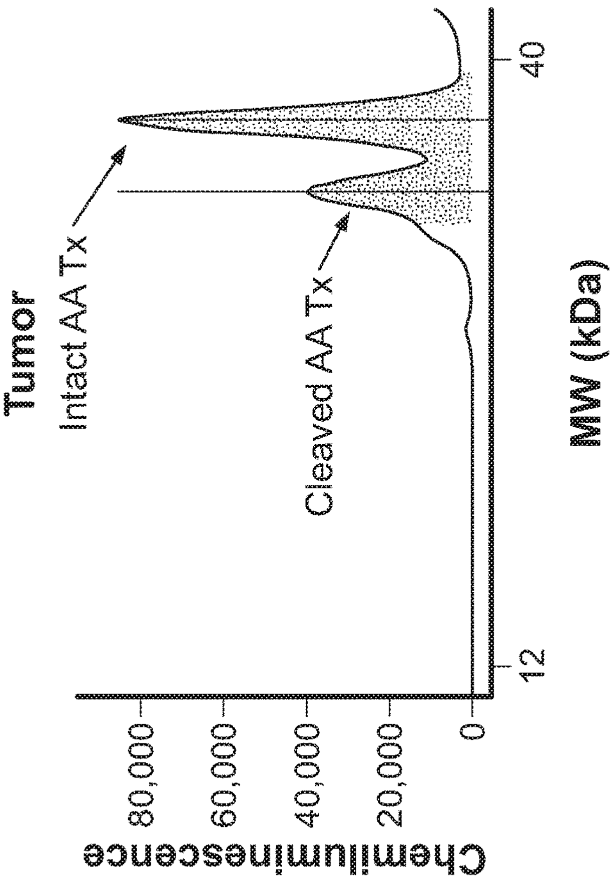

FIGS. 4A and 4B show preferential activation of anti-PDL1 activatable antibody PL07-2001-C5H9v2 in tumor versus plasma samples. In this study, MDA-MD-231 xenograft mice were treated with 1 mg/kg of anti-PDL1 activatable antibody PL07-2001-C5H9v2. Tumor and plasma samples were collected on day 4 (96 hours). Tumor homogenate and plasma samples were analyzed in the Wes™ system using the anti-id 17G1 antibody for detection. Plasma samples exhibited intact anti-PDL1 activatable antibody PL07-2001-C5H9v2 (FIG. 4B) whereas the tumor microenvironment activated at least a portion of the anti-PDL1 activatable antibody PL07-2001-C5H9v2 (FIG. 4A).

Example 5. Quantification of Activated and Intact Anti-PDL1 Activatable Antibodies in Biological Samples This Example demonstrates that the method of the present invention can be applied to different xenograph tumor types and different dosing concentrations.

Figure 5B:
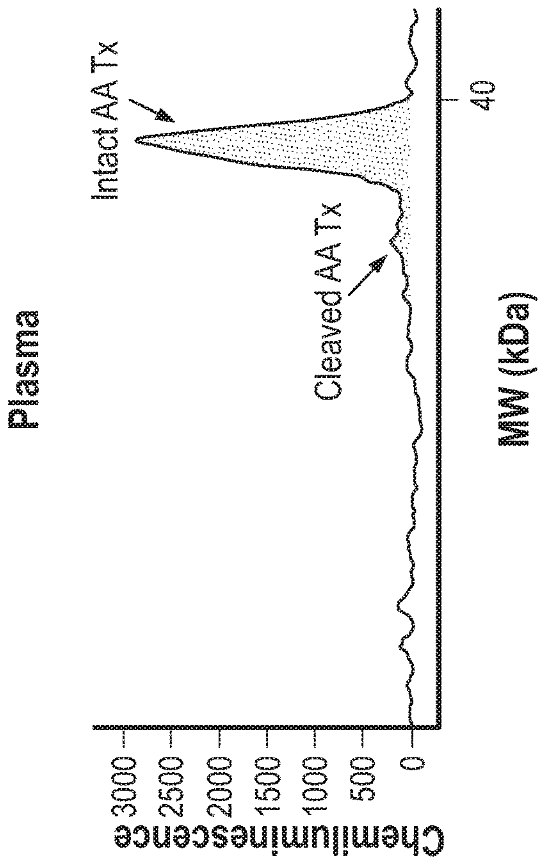
FIG. 5A and 5B are a series of graphs depicting preferential activation of activatable antibody therapeutics in tumor versus plasma detected in another xenograft tumor model. SAS xenograft mice were treated with 0.1 mg/kg of the anti-PDL1 activatable antibody referred to herein as PL07-2001-C5H9v2.
Figure 5A:
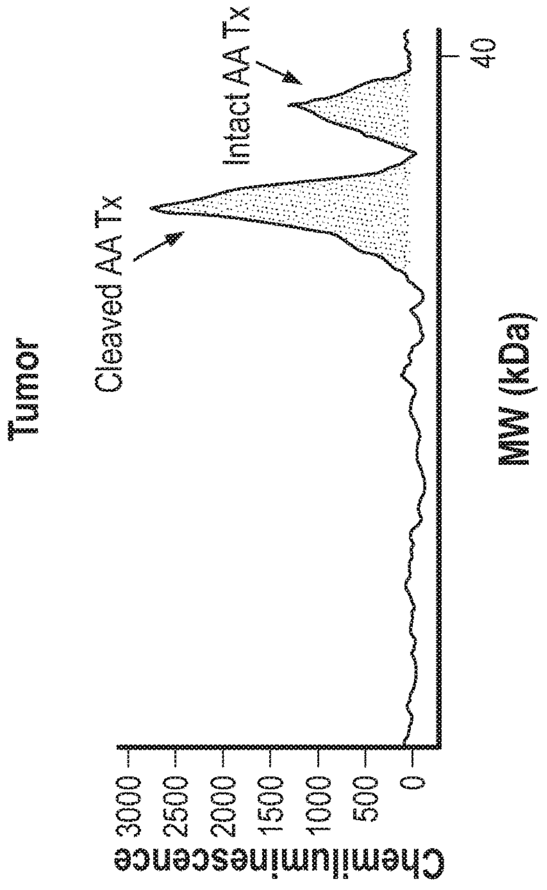

Briefly, a mouse xenograft tumor model was developed by SC implantation of $5 \times 10^6$ SAS cells in 100 uL serum-free medium to 7-8 week old female nude mice. Body weights and tumor measurements were measured and recorded twice weekly for the duration of the study. After tumors achieved volume of 450-550 $mm^3$, mice were randomized into 3 groups of equivalent average tumor volume and dosed with 0.1 mg/kg of anti-PDL1 activatable antibody PL07-2001-C5H9v2. Four days after treatment, tumor and plasma (heparin) samples were collected and stored at −80° C. prior to analysis. Tumor homogenates (i.e., lysates) were prepared in Thermo Scientific Pierce™ IP Lysis Buffer (Catalog #87788) with added Thermo Scientific Halt™ Protease Inhibitor Single Use Cocktail Kit (Catalog #78430) using Barocycler (Pressure Biosciences). Approximately 0.8 mg/mL of protein lysate in IP lysis buffer with HALT protease inhibitor/EDTA and plasma samples diluted 1 in 250 in PBS were analyzed in accordance with the methods of the present invention using the Wes™ system and the 17G1 antibody for detection. An HRP-conjugated anti-mouse secondary antibody was used in conjunction with luminol and peroxide and chemiluminescence was measured. FIGS. 5A and 5B indicate the preferential activation of activatable antibody therapeutics in tumor versus plasma samples.

Example 6. Quantification of Activated and Intact Anti-CD166 Activatable Antibodies in Biological Samples This Example describes the ability to detect activated and intact anti-CD166 activatable antibody 7614.6-3001-HuCD166 in plasma and xenograft tumor samples of mice administered 7614.6-3001-HuCD166.

The studies presented herein used the anti-CD166 activatable antibody referred to herein as 7614.6-3001-HuCD166, also referred to as HuCD166-7614.6-3001, which comprises the heavy chain sequence of SEQ ID NO: 432 and the light chain sequence of SEQ ID NO: 433, as shown below.

```
Anti-CD166 Activatable Antibody Sequences:
Heavy chain amino acid sequence
                                        (SEQ ID NO: 432)
QITLKESGPTLVKPTQTLTLTCTFSGFSLSTYGMGVGWIRQPPGKALEWL

ANIWWSEDKHYSPSLKSRLTITKDTSKNQVVLTITNVDPVDTATYYCVQI

DYGNDYAFTYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K

Light chain amino acid sequence
                                        (SEQ ID NO: 433)
LCHPAVLSAWESCSSGGGSSGGSAVGLLAPPGGLSGRSDNHGGSDIVMTQ

SPLSLPVTPGEPASISCRSSKSLLHSNGITYLYWYLQKPGQSPQLLIYQM

SNLASGVPDRFSGSGSGTDFTLKISRVEAEDVGVYYCAQNLELPYTFGQG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC
```

Figure 6A:
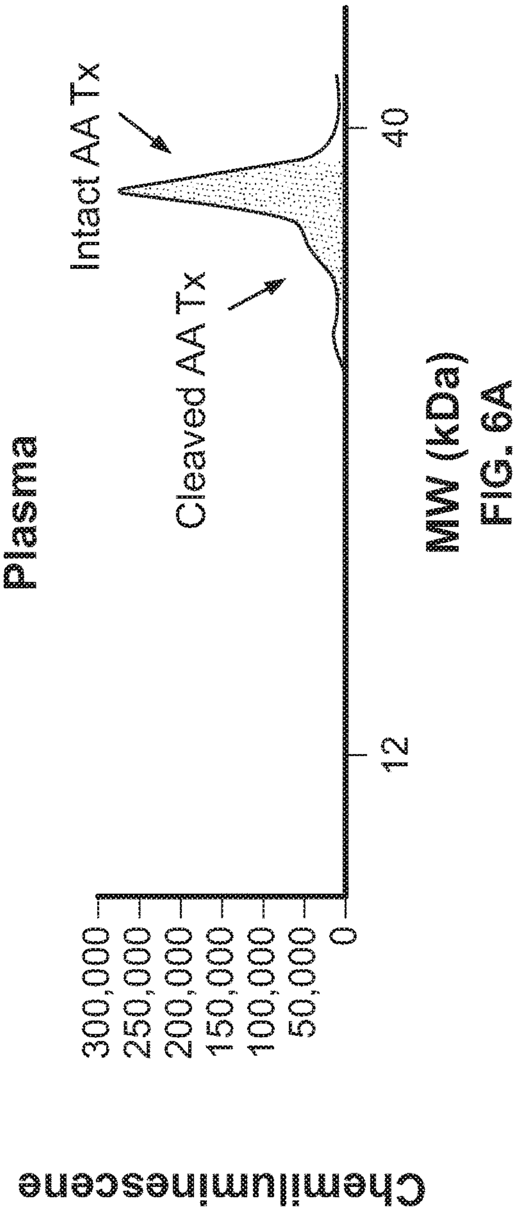
FIG. 6A and FIG. 6B are a series of graphs depicting preferential activation of activatable antibody therapeutics in tumor versus plasma detected in xenograft tumor model using the anti-CD166 activatable antibody referred to herein as 7614.6-3001-HuCD166. H292 xenograft mice were treated with 5 mg/kg of 7614.6-3001-HuCD166. Tumor and plasma samples were collected on day 1.
Figure 6B:
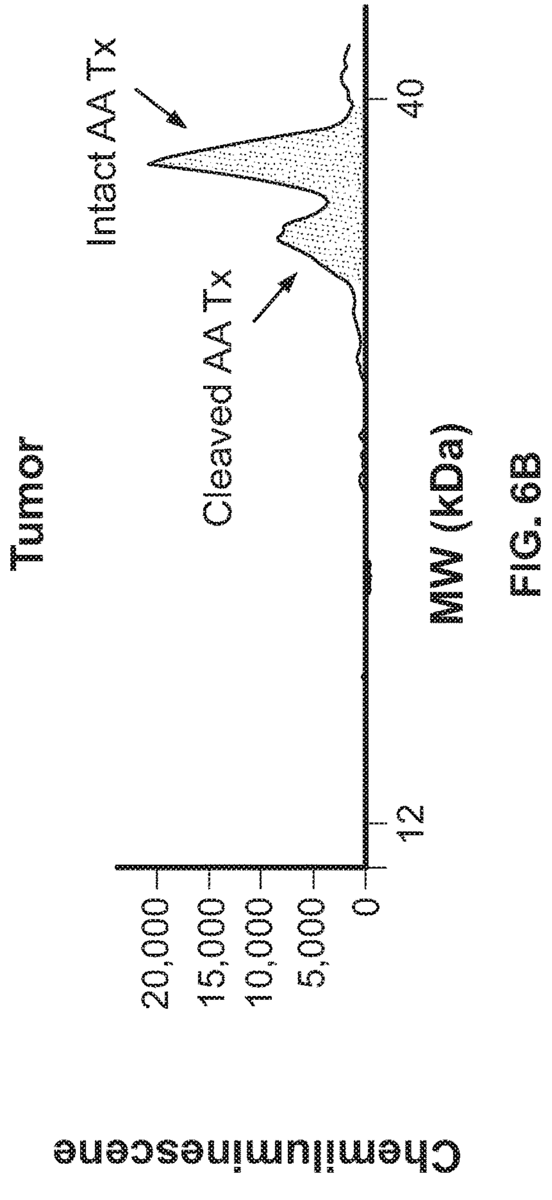

Quantification of activated and intact anti-CD166 activatable antibody 7614.6-3001-HuCD166 was assessed by the Wes™ system using anti-human IgG antibodies (anti-human IgG(H&L), American Qualex Catalog #A110UK). Nude mice were implanted subcutaneously with 5×10e6 H292 cells in serum-free medium mixed 1:1 with Matrigel™. Mice harboring 200-500 mm2 H292 xenographs were dosed with 5 mpk of anti-CD166 activatable antibody 7614.6-3001-HuCD166. One day after treatment, tumor and plasma (heparin) were collected and stored at −80° C. prior to analysis. Tumor homogenates were prepared in Thermo Scientific Pierce™ IP Lysis Buffer (Catalog #87788) with added Thermo Scientific Halt™ Protease Inhibitor Single Use Cocktail Kit (Catalog #78430) using Barocycler (Pressure Biosciences). One mg/mL of protein lysate in IP lysis buffer with HALT protease inhibitor/EDTA and plasma samples diluted 1 in 20 in PBS were analyzed by the Wes™, as described herein. An HRP-conjugated anti-mouse secondary antibody was used in conjunction with luminol and peroxide and chemiluminescence was measured. FIGS. 6A and 6B demonstrate preferential activation in tumor (FIG. 6B) as compared to plasma (FIG. 6A).

Example 7. Quantification of Activated and Intact Anti-EGFR Activatable Antibodies in Biological Samples This Example describes the ability to detect activated and intact anti-EGFR activatable antibodies 3954-2001-C225v5 and 3954-3001-C225v5 in plasma and xenograft tumor samples of mice administered anti-EGFR activatable antibodies 3954-2001-C225v5 or 3954-3001-C225v5.

The studies presented herein used the anti-EGFR activatable antibodies referred to herein as 3954-2001-C225v5 and 3954-3001-C225v5. Anti-EGFR activatable antibody 3954-2001-C225v5 comprises the C225v5 heavy chain amino acid sequence of SEQ ID NO: 446, shown below, and a light chain that comprises a masking moiety comprising the amino acid sequence CISPRGCPDGPYVMY (SEQ ID NO: 448), a cleavable moiety comprising the amino acid sequence ISSGLLSGRSDNH (SEQ ID NO: 406), and the C225v5 light chain antibody sequence comprising SEQ ID NO: 447, shown below. Anti-EGFR activatable antibody 3954-3001-C225v5 comprises the heavy chain sequence of SEQ ID NO: 446, shown below, and a light chain that comprises a masking moiety comprising the amino acid sequence CISPRGCPDGPYVMY (SEQ ID NO: 448), a cleavable moiety comprising the amino acid sequence AVGLLAPPGGLSGRSDNH (SEQ ID NO: 412), and the light chain sequence of SEQ ID NO: 447, shown below.

```
C225v5 Heavy Chain Antibody Amino Acid Sequence:
                                   (SEQ ID NO: 446)
QVQLKQSGPGLVQPSQSLSITCTVSGFSLTNYGVHWVRQSPGKGLEWLG

VIWSGGNTDYNTPFTSRLSINKDNSKSQVFFKMNSLQSQDTAIYYCARA

LTYYDYEFAYWGQGTLVTVSAASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

C225v5 Light Chain Antibody Amino Acid Sequence:
                                   (SEQ ID NO: 447)
QILLTQSPVILSVSPGERVSFSCRASQSIGTNIHWYQQRTNGSPRLLIK

YASESISGIPSRFSGSGSGTDFTLSINSVESEDIADYYCQQNNNWPTTF

GAGTKLELKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

Figure 7B:
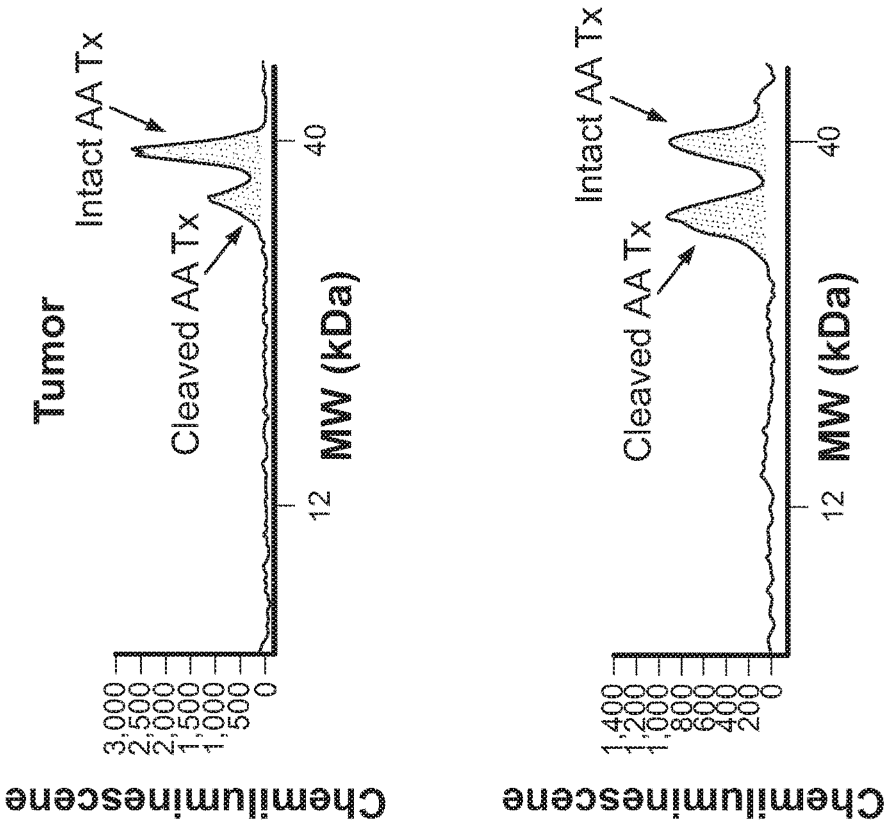
FIG. 7A and FIG. 7B are a series of graphs depicting preferential activation of activatable antibody therapeutics in tumor versus plasma detected in xenograft tumor model using EGFR activatable antibodies containing different substrates. H292 xenograft mice were treated with 25 mg/kg of either C225-3954-2001 or C225-3954-3001 activatable antibody therapeutics. Tumor and plasma samples were collected on day 4.
Figure 7A:
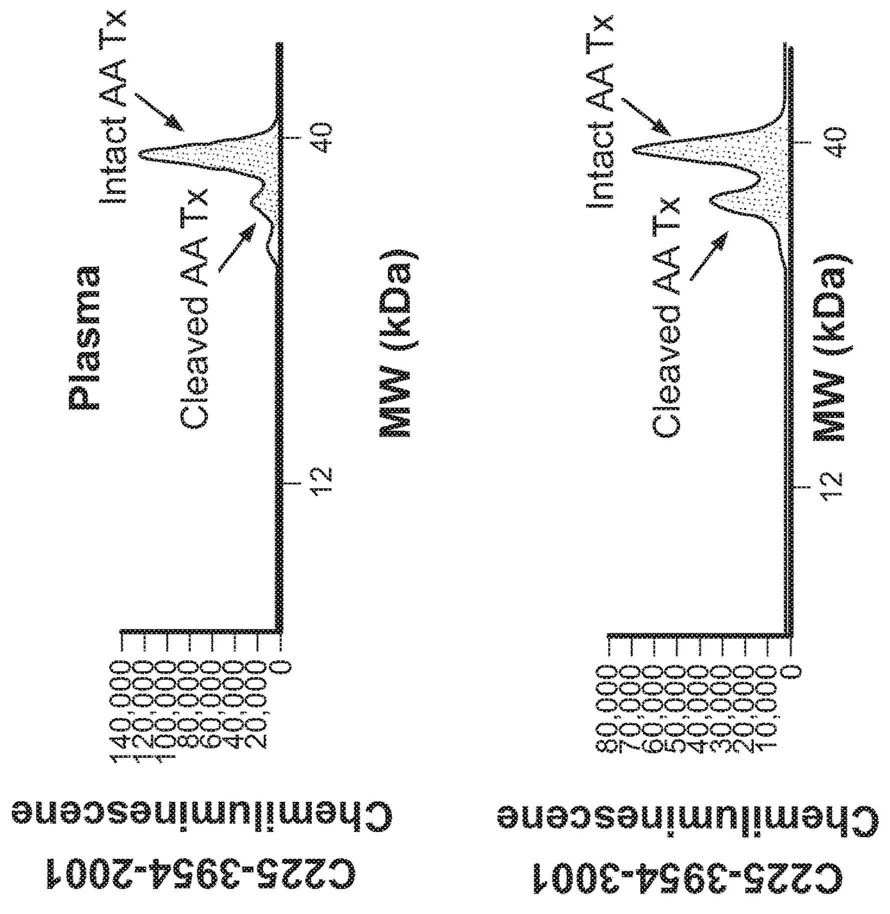

Quantification of activated and intact anti-EGFR activatable antibodies 3954-2001-C225v5 and 3954-3001-C225v5 was assessed by the Wes™ system using anti-human IgG antibodies (anti-human IgG(H&L), American Qualex Catalog #A110UK). Nude mice were implanted subcutaneously with 5x10e6 H292 cells in serum-free medium mixed 1:1 with Matrigel™. Mice harboring 200-500 mm2 H292 xenografts were dosed with 25 mg/kg of 3954-2001-C225v5 or 3954-3001-C225v5. Tumor and plasma (heparin) were collected 4 days after treatment and stored at −80° C. prior to analysis. Tumor homogenates were prepared in Thermo Scientific Pierce' IP Lysis Buffer (Catalog #87788) with added Thermo Scientific Halt™ Protease Inhibitor Single Use Cocktail Kit (Catalog #78430) using Barocycler (Pressure Biosciences). 0.4 mg/mL of protein lysate in IP lysis buffer with HALT protease inhibitor/EDTA and plasma samples diluted 1 in 500 in PBS were analyzed by the Wes™ system as described herein. An HRP-conjugated anti-goat secondary antibody was used in conjunction with luminol and peroxide and chemiluminescence was measured. FIGS. 7A and 7B demonstrate preferential activation in tumor (FIG. 7B) as compared to plasma (FIG. 7A).

Example 8. Quantification of Activated and Intact Anti-CD71 Activatable Antibodies in Biological Samples This Example describes the ability to detect activated and intact anti-CD71 activatable antibody TF02.13-2011-21.12.

The studies presented herein used the anti-CD71 activatable antibody referred to herein as TF02.13-2011-21.12, also referred to as 21.12-TF02.13-2011 and huCD71-TF02.13-2011, which comprises the heavy chain sequence of SEQ ID NO: 434 and the light chain sequence of SEQ ID NO: 435, as shown below.

```
Anti-CD71 Activatable Antibody Sequences:
Heavy chain amino acid sequence
                                   (SEQ ID NO: 434)
QVQLVQSGAEVKKPGASVKMSCKASGYTFTSYWMHWVRQAPGQGLEWIG

AIYPGNSETGYAQKFQGRATLTADTSTSTAYMELSSLRSEDTAVYYCTR

ENWDPGFAFWGQGTLITVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK

Light chain amino acid sequence
                                   (SEQ ID NO: 435)
NLCTEHSAALDCRSYGGGSSGGSISSGLLSGRSDNPGGGSDIQMTQSPS

SLSASVGDRVTITCSASSSVYYMYWFQQKPGKAPKLWIYSTSNLASGVP

SRFSGSGSGTDYTLTISSMQPEDFATYYCQQRRNYPYTFGQGTKLEIKR

TVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVT

KSFNRGEC
```

Figure 8:
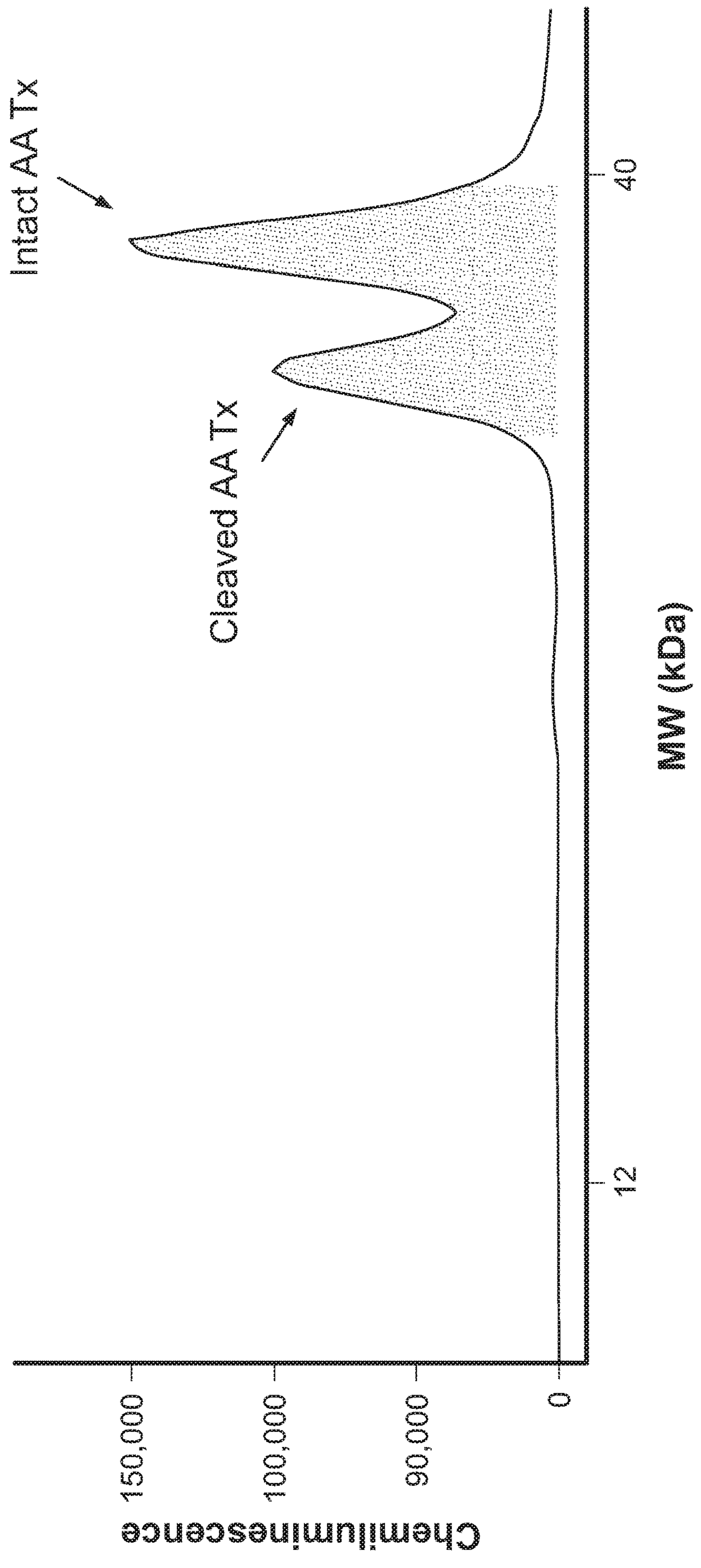
FIG. 8 is a graph of results obtained from the capillary electrophoresis immunoassay method of the present invention to assess the ratio between activated and non-activated anti-CD71 activatable antibody referred to herein as TF02.13-2011-21.12 in biological samples. The method was used to separate pre-activated activatable antibody mixed with non-activated, i.e., intact, activatable antibody in the presence of human plasma.

Anti-CD71 activatable antibody TF02.13-2011-21.12 was activated with 200 nM matriptase (R&D Systems Catalog # 3946-SE) overnight at 37° C. and mixed with intact anti-CD71 activatable antibody TF02.13-2011-21.12 in human plasma (Bioreclaimation). The mixture was then analyzed by the Wes™ system as described herein using a supernatant from a hybridoma clone derived from mice immunized with peptides comprising CDR1 and CDR3 of the light chain of anti-CD71 activatable antibody TF02.13-2011-21.12, and that supernatant specifically recognizes anti-CD71 activatable antibody TF02.13-2011-21.12. An HRP-conjugated anti-mouse secondary antibody was used in conjunction with luminol and peroxide and chemiluminescence was measured. FIG. 8 shows the ability to separate pre-activated from intact anti-CD71 activatable antibody TF02.13-2011-21.12 in plasma.

Example 9. Quantification of Activated and Intact Anti-PD1 Activatable Antibodies This Example describes the ability to detect activated and intact anti-PD1 activatable antibody PD34-2011-A1.5 hIgG4 S228P.

The studies presented herein used the anti-PD1 activatable antibody referred to herein as PD34-2011-A1.5 hIgG4 S228P, also referred to as A1.5-PD34-2011 and 1.5-PD34-2011, which comprises the heavy chain sequence of SEQ ID NO: 436 and the light chain sequence of SEQ ID NO: 437, as shown below.

Anti-CD71 Activatable Antibody Sequences:
Heavy chain amino acid sequence
(SEQ ID NO: 436)

EVQLVESGGGLVQPGGSLRLSCAASGFTFSGYAMSWVRQAPGKGLEWVAY

ISNSGGNAHYADSVKGRFTISRDNSKNTLYLQMNSLRAEDTAVYYCTRED

YGTSPFVYWGQGTLVTVSSASTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFLGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK

Light chain amino acid sequence
(SEQ ID NO: 437)

TSYCSIEHYPCNTHHGGGSSGGSISSGLLSGRSDNPGGGSDIQLTQSPSS

LSASVGDRVTITCRASESVDAYGISFMNWFQQKPGKAPKLLIYAASNQGS

GVPSRFSGSGSGTDFTLTISSMQPEDFATYYCQQSKDVPWTFGQGTKLEI

KRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVT

KSFNRGEC

Figure 9:
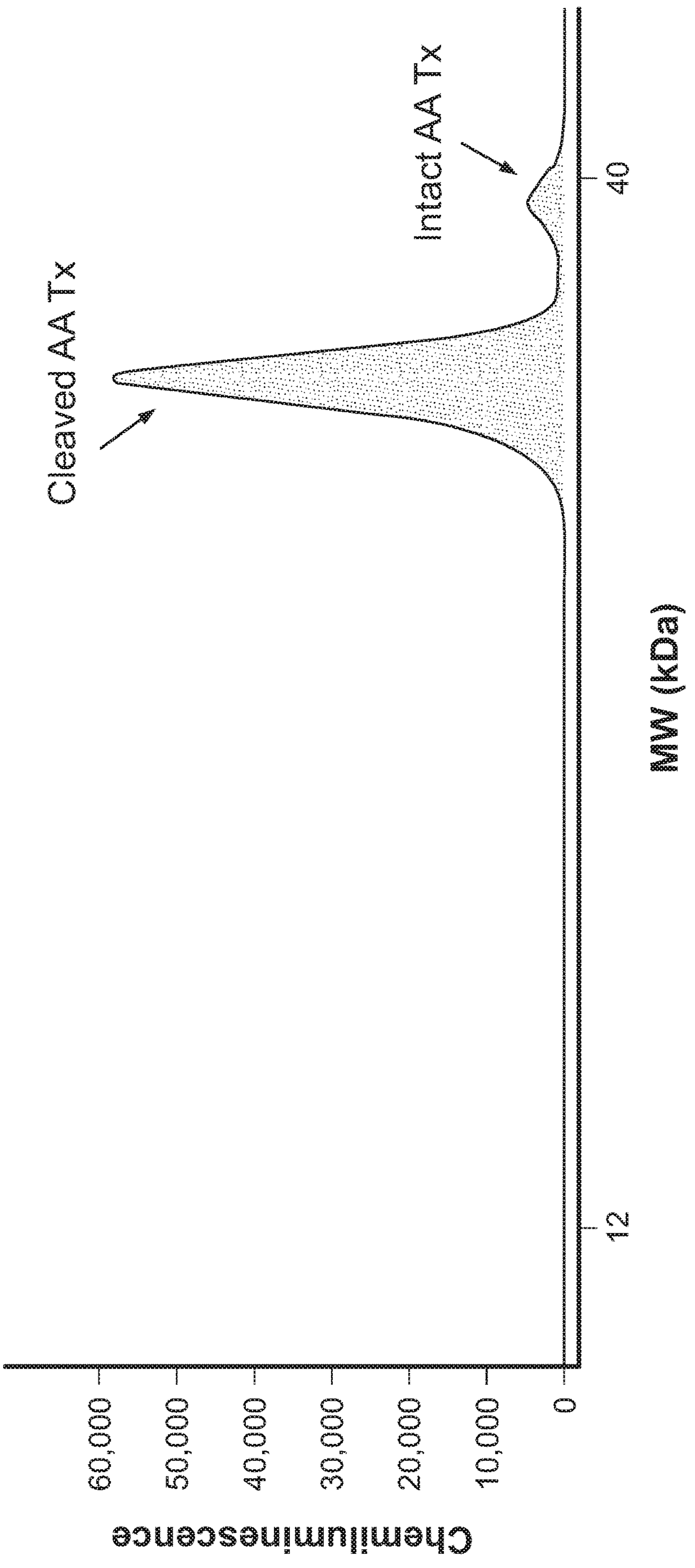
FIG. 9 is a graph depicting the results obtained using the capillary electrophoresis immunoassay method of the disclosure to assess the ratio between activated and non-activated anti-PD1 activatable antibody referred to herein as PD34-2011-A1.5 hIgG4 S228P in biological samples. The method was used to separate pre-activated activatable antibody mixed with non-activated, i.e., intact, activatable antibody in the presence of human plasma.

Anti-PD1 activatable antibody PD34-2011-A1.5 hIgG4 S228P was activated with 200 nM MMP14 (R&D Systems Catalog # 918-MP) overnight at 37° C. and mixed with intact anti-PD1 activatable antibody PD34-2011-A1.5 hIgG4 S228P. The mixture was then analyzed by Wes™ system (ProteinSimple) as described herein using anti-human IgG (H&L) (American Qualex Catalog #A110UK). An HRP-conjugated anti-goat secondary antibody was used in conjunction with luminol and peroxide and chemiluminescence was measured. FIG. 9 shows the ability to separate intact anti-PD1 activatable antibody PD34-2011-A1.5 hIgG4 S228P from the corresponding activated (cleaved) activatable antibody.

Example 10. Quantification of Activated and Intact Anti-CD166 Conjugated Activatable Antibodies This Example describes the ability to detect activated and intact anti-CD166 activatable antibody 7614.6-3001-HuCD166 conjugated to maytansinoid toxin DM4 through an SPDB linker.

The studies presented herein used a DM4-conjugated activatable antibody of the anti-CD166 activatable antibody referred to herein as 7614.6-3001-HuCD166, also referred to as HuCD166-7614.6-3001, which comprises the heavy chain sequence of SEQ ID NO: 432 and the light chain sequence of SEQ ID NO: 433, as shown below.

Anti-CD166 Activatable Antibody Sequences:
Heavy chain amino acid sequence
(SEQ ID NO: 432)

QITLKESGPTLVKPTQTLTLTCTFSGFSLSTYGMGVGWIRQPPGKALEWL

ANIWWSEDKHYSPSLKSRLTITKDTSKNQVVLTITNVDPVDTATYYCVQI

DYGNDYAFTYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K

Light chain amino acid sequence
(SEQ ID NO: 433)

LCHPAVLSAWESCSSGGGSSGGSAVGLLAPPGGLSGRSDNHGGSDIVMTQ

SPLSLPVTPGEPASISCRSSKSLLHSNGITYLYWYLQKPGQSPQLLIYQM

SNLASGVPDRFSGSGSGTDFTLKISRVEAEDVGVYYCAQNLELPYTFGQG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

Figure 10A:
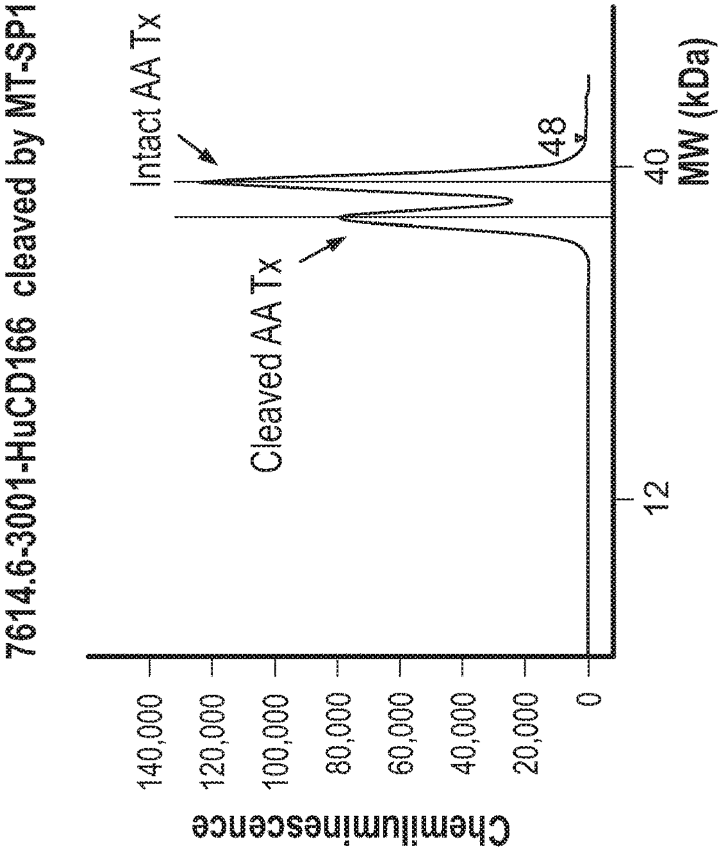
FIGS. 10A and 10B are a series of graphs depicting the results obtained using a capillary electrophoresis immunoassay method of the disclosure to assess activated and intact (i.e., non-activated) activatable antibody (AA) therapeutics (AA Tx) using the anti-CD166 activatable antibody referred to herein as 7614.6-3001-HuCD166. The capillary immunoassay method of the present invention was used to separate 7614.6-3001-HuCD166 activatable antibodies that have been partially activated with matriptase (FIG. 10A) or MMP-14 (FIG. 10B) from intact 7614.6-3001-HuCD166 activatable antibodies.
Figure 10B:
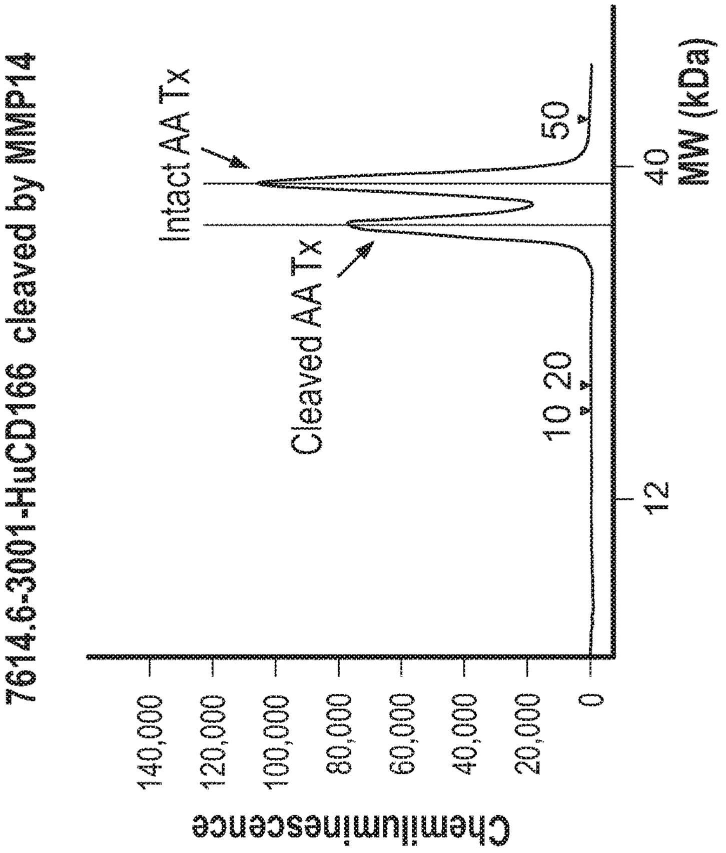

The anti-CD166 conjugated activatable antibody was activated with either 80 ug/ml of matriptase (R&D Systems Catalog # 3946-SE) or 80 ug/ml of MMP14 (R&D Systems Catalog # 918-MP) for 2 hours at 37° C. and mixed with intact conjugated activatable antibody. The mixture was then analyzed by the Wes™ system as described above using anti-human IgG (H&L) (American Qualex Catalog #A110UK). An HRP-conjugated anti-goat secondary antibody was used in conjunction with luminol and peroxide and chemiluminescence was measured. FIGS. 10A and 10B show the ability to separate matriptase-activated (FIG. 10A) or MMP14-activated (FIG. 10B) conjugated activatable antibodies from intact conjugated activatable antibodies.

Example 11. Tertiary Detection Protocol

The signal associated with (intact) activatable antibody and/or activated (cleaved) activatable antibody can be amplified using an additional antibody detection step. In this protocol, a secondary antibody that is not conjugated to horse radish peroxidase (HRP) is used to detect the primary antibody, a tertiary detection antibody conjugated with HRP is then used to amplify the signal. In this example, activatable anti-CD166, 7614.6-3001-HuCD166 was detected by probing with anti-id antibody clone 22B8 (not conjugated to HRP) followed by biotinlyated anti-rat IgG FCgamma (Jackson Immunology 112-035-008), and then streptavidin HRP (043-459-2) (i.e., an example of the tertiary detection protocol) or clone 22B8 followed by HRP conjugated anti-rat IgG FCgamma (Jackson Immunology 112-065-008) (i.e., an example of the two step protocol). Luminol and peroxide reagents were used, and chemiluminescence was measured. Nude mice were implanted subcutaneously with H292 cells in serum-free medium mixed 1:1 with Matrigel™. Mice bearing H292 xenografts were treated with 5 mg/kg of 7614.6-3001-HuCD166. Tissues were collected at 4 day post-dose. Tumor homogenates were prepared in Thermo Scientific Pierce™ IP Lysis Buffer (Catalog #87788) with added Thermo Scientific Halt™ Protease Inhibitor Single Use Cocktail Kit (Catalog #78430) using Barocycler (Pressure Biosciences). 1.5 mg/mL of proteins were analyzed on the Wes™ capillary electrophoresis immunoassay system, as described herein.

Figure 11A:
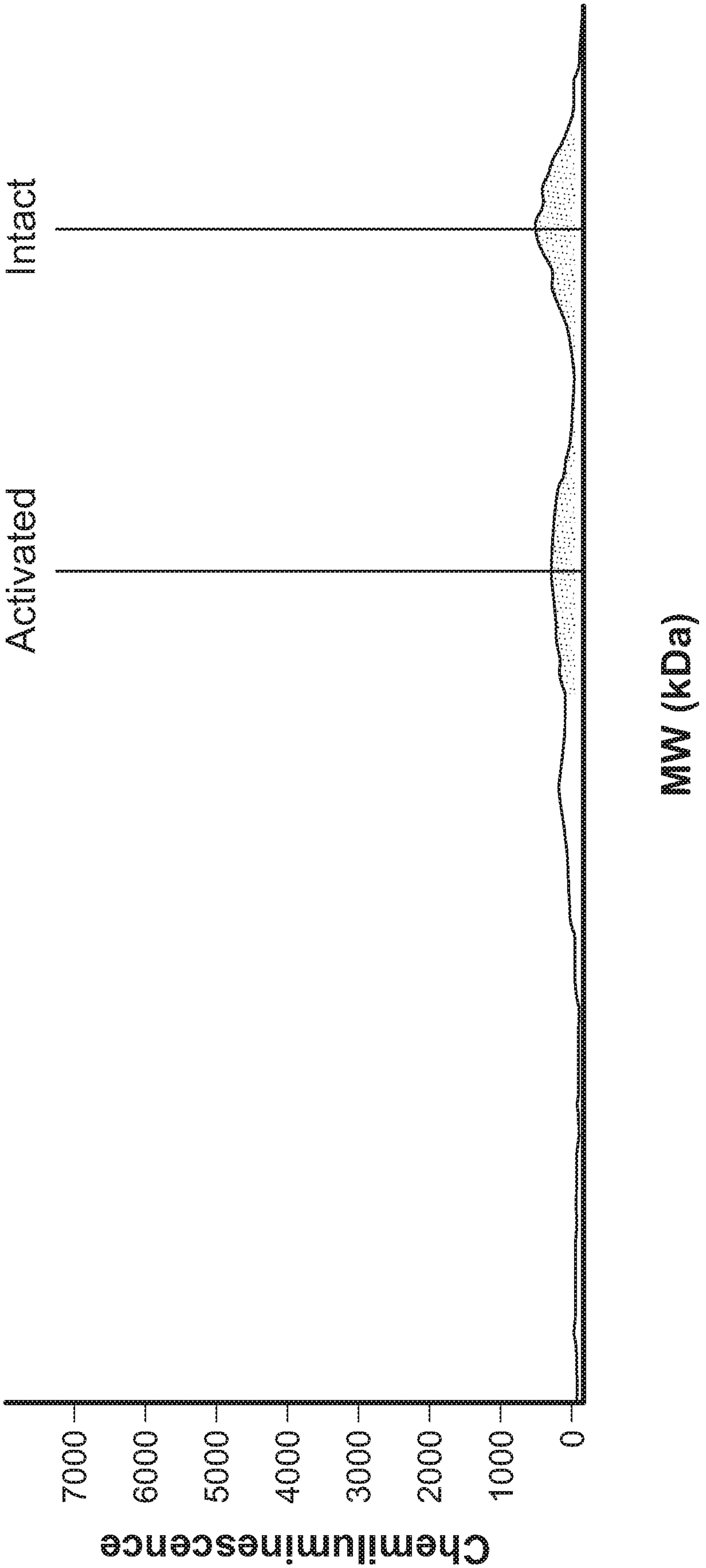
FIGS. 11A and 11B depict chemiluminescence signal for activated activatable antibody (cleavage product of 7614.6-3001-HuCD166) and intact/activated activatable antibody (intact 7614.6-3001-HuCD166), using a two step detection protocol and a tertiary detection protocol, respectively, as described in Example 11.
Figure 11B:
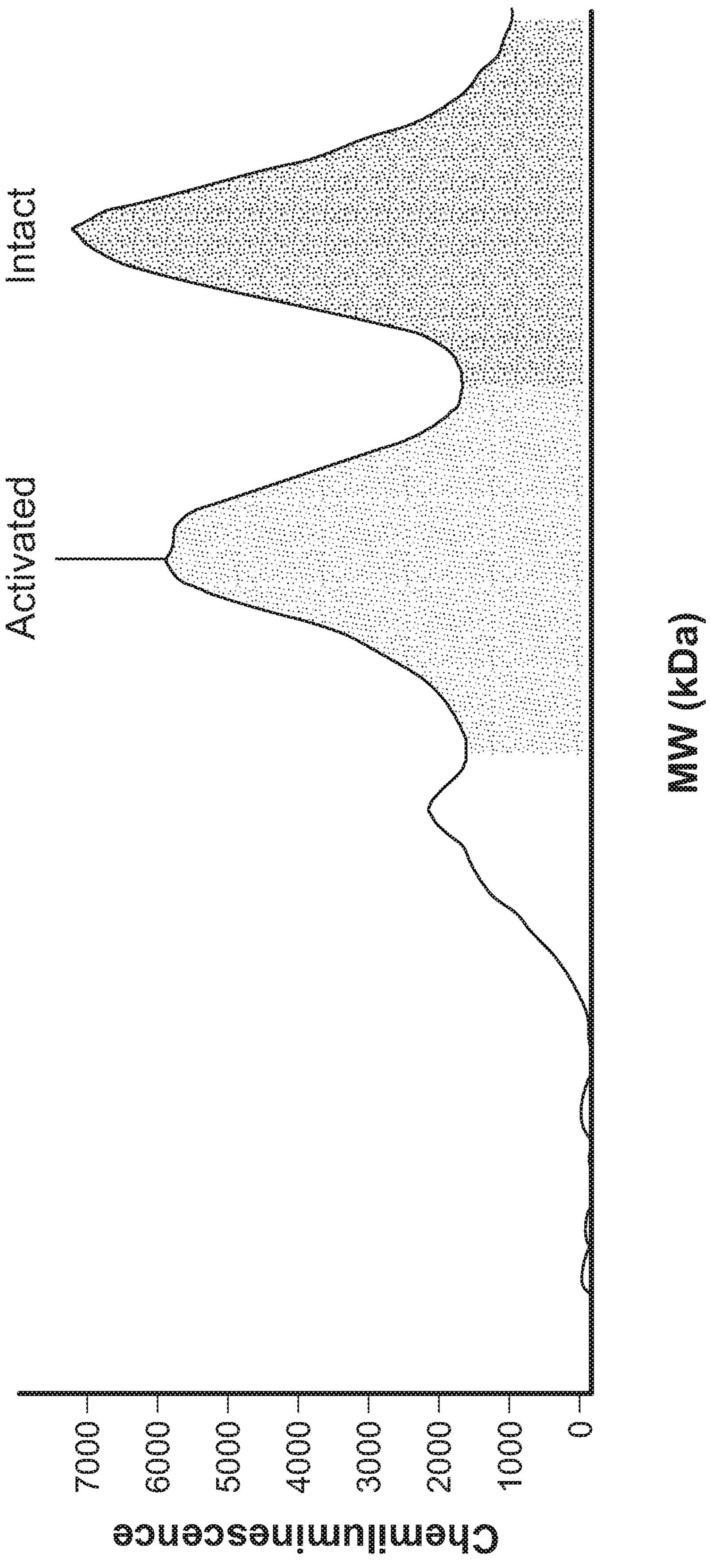

FIG. 11A depicts the magnitude of chemiluminescence signal associated with molecular species having different molecular weights in the biological sample using the two step detection protocol. The plot shows the peaks detected for activated activatable antibody (cleavage product of 7614.6-3001-HuCD166) and for intact/activated activatable antibody (intact 7614.6-3001-HuCD166). FIG. 11B depicts the magnitude of chemiluminescence signal associated with molecular species having different molecular weights in the biological sample using the tertiary detection protocol. Use of the tertiary detection protocol resulted in a much greater signal for both 7614.6-3001-HuCD166 (intact activatable antibody) and its cleavage product (activated activatable antibody). The results illustrate the amplification of signal obtained using the tertiary protocol as compared to the signal obtained using the two step protocol, thus facilitating detection of each species.

Example 12. Quantification of Activated and Intact Anti-Jagged Activatable Antibodies in Biological Samples This Example describes the ability to detect activated and intact anti-Jagged activatable antibodies 5342-3001-4D11 tumor samples of mice administered anti-Jagged activatable antibodies 5342-3001-4D11

The studies presented herein used the anti-Jagged activatable antibodies referred to herein as 5342-3001-4D11. Anti-Jagged activatable antibody 5342-3001-4D11 comprises the heavy chain sequence of SEQ ID NO:950 and the light chain sequence of SEQ ID NO:951. Both sets of sequences are shown below:

```
4D11-Heavy Chain:
                                        (SEQ ID NO: 950)
EVQLLESGGGLVQPGGSLRLSCAASGFTFSSYAMSWVRQAPGKGLEWVSS

IDPEGRQTYYADSVKGRFTISRDNSKNTLYLQMNSLRAEDTAVYYCAKDI

GGRSAFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK*

4D11-5342-8504-Light Chain
                                        (SEQ ID NO: 951)
QGQSGQCNIWLVGGDCRGWQGGSSGGSGGSGGAVGLLAPPGGLSGRSDNH

GGGSDIQMTQSPSSLSASVGDRVTITCRASQSISSYLNWYQQKPGKAPKL

LIYAASSLQSGVPSRFSGSGSGTDFTLTISSLQPEDFATYYCQQTVVAPP

LFGQGTKVEIKRTVAAPSVFIFPPSDEQLKSGTASVVCLLNNFYPREAKV
```

-continued

```
QWKVDNALQSGNSQESVTEQDSKDSTYSLSSTLTLSKADYEKHKVYACEV

THQGLSSPVTKSFNRGEC*
```

Figure 12:
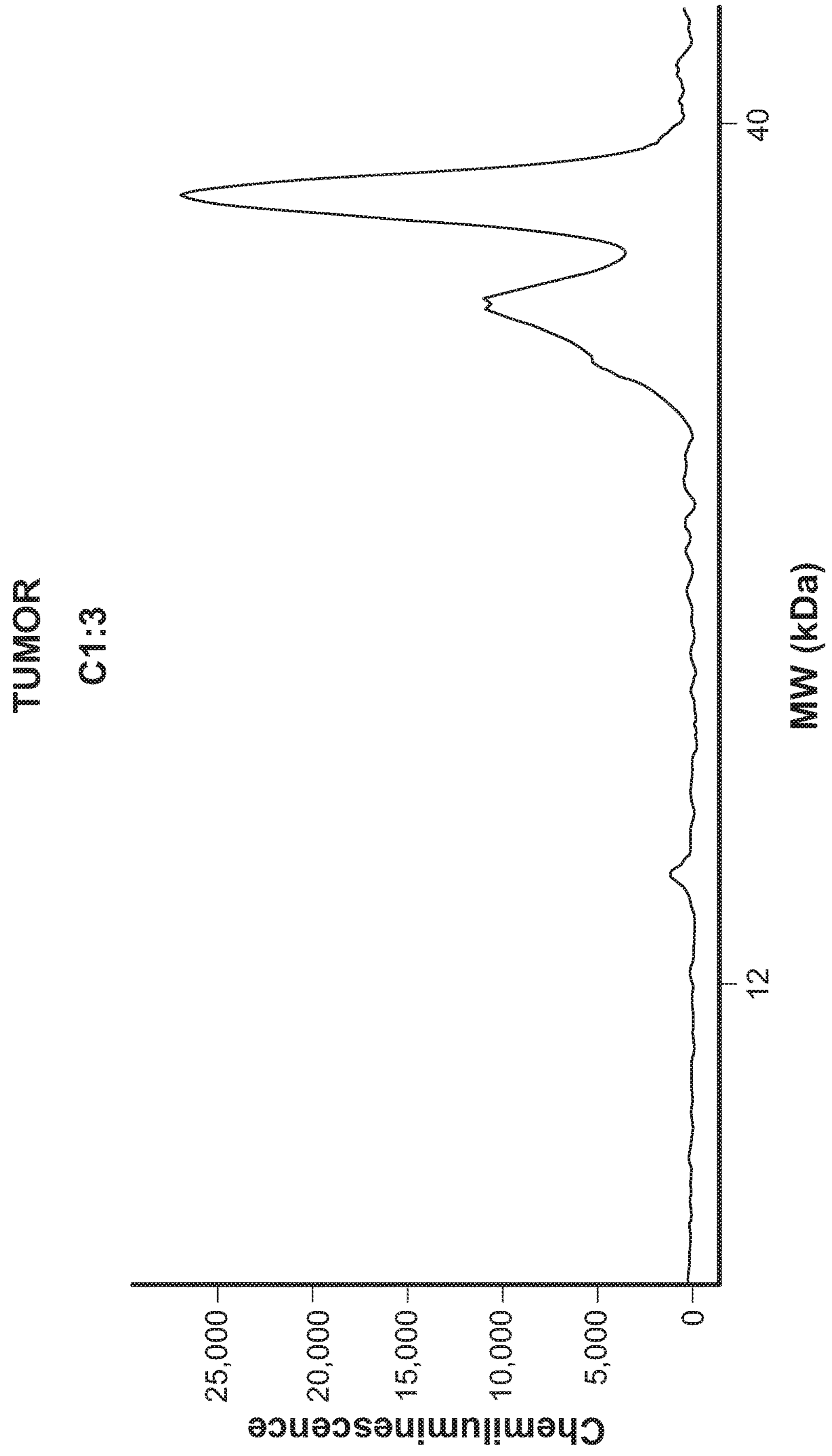
FIG. 12 depicts the chemiluminscence signals detected for anti-Jagged (intact) activatable antibody 5342-3001-4D11 and the corresponding activated activatable antibody in tumor tissue.

Quantification of activated and intact anti-Jagged activatable antibodies 5342-3001-4D11 was assessed in accordance with the methods of the present invention using the Wes™ system (Protein Simple, and anti-human IgG antibodies (anti-human IgG (H&L), American Qualex Catalog #A110UK). Nude mice were implanted subcutaneously with BxPC3 cells in serum-free medium mixed 1:1 with Matrigel™. Mice harboring 200-500 mm2 BxPC3 xenographs were dosed with 10 mg/kg of 5342-3001-4D11. Tumor tissues were collected 4 days after treatment and stored at −80° C. prior to analysis. Tumor homogenates were prepared in Thermo Scientific Pierce™ IP Lysis Buffer (Catalog #87788) with added Thermo Scientific Halt™ Protease Inhibitor Single Use Cocktail Kit (Catalog #78430) using Barocycler (Pressure Biosciences). 1.5 mg/mL of protein lysate in IP lysis buffer with HALT protease inhibitor/EDTA and plasma samples diluted 1 in 100 in PBS were analyzed on the Wes™ system. An HRP-conjugated anti-goat secondary antibody was used in conjunction with luminol and peroxide and chemiluminescence was measured. FIG. 12 depicts the chemiluminscence signal detected for each species, thus demonstrating detection of activation of 5342-3001-4D11 anti-Jagged activatable antibody in tumor tissue.

Example 13. Quantification of Activated and Intact Anti-PDL1 Activatable Antibodies in Biological Samples using Standard Curves This example illustrates the protocol for quantifying intact activatable antibody and activated activatable antibody in a biological sample by generating and using standard curves.

Tumor lysate or plasma samples believed to contain activatable antibody and/or activated activatable antibody are prepared. The samples are evaluated on the Wes™ system (ProteinSimple), as described herein, and the results are compared to standard curves of purified recombinant intact activatable antibody PL07-2001-C5H9v2 and the corresponding activated antibody. Concentrations of activatable antibody and activated activatable antibody are determined using the standard curves.

Plasma is diluted in the 1:10 to 1:100 range, and tumor lysate is diluted in the 1:1 to 1:10 range. Capillaries are reserved for standard curve materials and undergo electrophoresis and immunoblotting in parallel with samples loaded with the biological samples. Samples for the standard curves are prepared using (1) pooled normal K2-EDTA plasma for the plasma samples (see below) or (2) Pierce IP lysis buffer (see below). The set of capillaries used for the standard curves contain intact activatable antibody and activated activatable antibody at the same dilution used to test the samples. A pool of normal-donor K2-EDTA plasma (Bioreclamation) is used for standard curve preparation for plasma samples.

K2-EDTA plasma from 7 human donors was collected and combined in equal volumes to make a normal-donor pool. A sample from one subject was not included in the pool because of the milky appearance of the plasma. Tumor lysate was prepared.

Materials: 10.7 mg/ml intact activatable antibody PL07-2001-C5H9v2, buffer: 8% sucrose, 30 mM NaCl, 0.02% Tween 80, 25 mM succinate pH 6; 11.35 mg/ml of corresponding activated activatable antibody, PBS buffer, pH 7.2.

Dilution series were prepared in a full-skirt PCR plate (Axygen PCR96FSC; ~100 ul wells) or a 450 ul V-bottom plate (Axygen P-96-450V-C-S; ~500 ul wells)), depending on the volume, starting at 17,500 ng/ml down to 8 ng/ml (in 3-fold increments), with one zero/blank sample per curve. Dilutions were stored on ice prior to loading into Wes™ system capillary cartridges (ProteinSimple). Anti-id antibody 17G1 (1.3 mg/ml) (see Example 2) was used as the primary antibody at a dilution of 1:1200. Anti-mouse secondary antibody-HRP conjugate (neat, ProteinSimple), 10 ul/well, as specified in the vendor's plate layout (part # 042-205).

Once samples were prepared and the Wes™ cartridge (ProteinSimple) was loaded with the reagents needed for the assay, the samples (biological samples (4 replicates) and the samples for the standard curves (2 replicates, including 2 zero/blanks), as well as biotinylated molecular weight standards reagent from the Wes™ kit (ProteinSimple)) were loaded into the Wes™ cartridge (ProteinSimple).

Operation of the Wes™ system was conducted in accordance with the manufacturer's instructions. The results showed that the sample separated into intact (~38 kD) or "activated" (~35 kD) peaks on the Wes™ platform. The intact and active peaks were then quantified against the standard curves prepared for intact activatable antibody PL07-2001-C5H9v2 and the corresponding activated antibody, and the concentrations for each were determined in ng/ml.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed:

1. A method of quantitating a level of activation of an activatable antibody, the method comprising:

i) contacting a loaded capillary or population of loaded capillaries with a biological sample comprising one or more components selected from the group consisting of an uncleaved activatable antibody, a cleaved activated antibody, and a combination thereof, wherein the uncleaved activatable antibody comprises an antibody or an antigen binding fragment thereof (AB) that specifically binds a target, a masking moiety (MM) coupled to the AB, and a cleavable moiety (CM) coupled to the AB, wherein the MM inhibits the binding of the AB to the target, wherein the CM is a polypeptide that functions as a substrate for a protease, wherein protease cleavage of the CM generates the cleaved activated antibody;

wherein the loaded capillary or population of loaded capillaries is/are pre-loaded with a stacking matrix and a separation matrix;

ii) separating one or more high molecular weight (MW) components of the biological sample from one or more low molecular weight (MW) components of the biological sample within each capillary, wherein at least one high MW component comprises the uncleaved activatable antibody and wherein at least one low MW component comprises the cleaved activated antibody;

iii) immobilizing the high MW components and the low MW components within each capillary;

iv) immunoprobing each capillary with at least a first reagent that is specific for at least one activatable antibody, wherein the first reagent comprises an anti-idiotypic antibody or antigen-binding fragment thereof, wherein when the MM and CM are conjugated to a heavy chain, the anti-idiotypic antibody or antigen-binding fragment thereof binds to a variable heavy chain region of the uncleaved activatable antibody and the cleaved activated antibody, and wherein when the MM and CM are conjugated to a light chain, the anti-idiotypic antibody or antigen-binding fragment thereof binds to a variable light chain region of the uncleaved activatable antibody and the cleaved activated antibody; and v) detecting and quantitating a level of the first reagent in each capillary or population of capillaries to determine relative levels of cleaved activated antibody and uncleaved activatable antibody in each capillary or population of capillaries, thereby determining the level of activation of the activatable antibody.

2. The method of claim 1, further comprising, prior to step i), loading at least one capillary or a population of capillaries with a stacking matrix and a separation matrix to generate the at least one loaded capillary or a population of loaded capillaries.

3. The method of claim 1, wherein the separating step is carried out for a separation time of at least about 35 minutes, at least about 36 minutes, at least about 37 minutes, or at least about 38 minutes.

4. The method of claim 1, wherein step iii) comprises using UV light to immobilize the high MW components and the low MW components of the biological sample.

5. The method of claim 1, wherein the activatable antibody is selected from the group consisting of a conjugated activatable antibody, a multispecific activatable antibody, and a conjugated multispecific activatable antibody.

6. The method of claim 1, wherein the anti-idiotypic antibody or antigen-binding fragment thereof, binds to a variable light chain (VL) CDR of the at least one activatable antibody, conjugated activatable antibody, multispecific activatable antibody, conjugated multispecific activatable antibody, or combination thereof, wherein the VL CDR is selected from the group consisting of VL CDR1, VL CDR2, and VL CDR3.

7. The method of claim 1, wherein the first reagent is a detectable reagent.

8. The method of claim 1, wherein step iv) further comprises loading each capillary with a second reagent that specifically binds to the first reagent.

9. The method of claim 8, wherein the second reagent comprises a secondary antibody.

10. The method of claim 8, wherein the secondary reagent comprises a detectable label.

11. The method of claim 9, wherein the second reagent comprises a secondary antibody conjugated to a detectable label.

12. The method of claim 9, wherein the secondary antibody is not conjugated to a detectable label.

13. The method of claim 12, wherein the secondary antibody is conjugated to a first binding tag of a set of a first binding tag and a second binding tag, wherein the first binding tag is capable of binding to the second binding tag.

14. The method of claim 13, wherein step iv) further comprises loading each capillary with a third reagent that specifically binds to the second reagent.

15. The method of claim 14, wherein the third reagent comprises a reporter enzyme conjugated to the second binding tag.

16. The method of claim 15, wherein the reporter enzyme is selected from the group consisting of horseradish peroxidase and alkaline phosphatase.

17. The method of claim 15, wherein the first and second binding tags are selected from the group consisting of biotin and streptavidin; streptavidin and biotin; biotin and avidin; and avidin and biotin; respectively.

18. The method of claim 14, wherein the third reagent comprises a detectable tertiary antibody.

19. The method of claim 1, wherein step iv) further comprises loading each capillary with a substrate selected from the group consisting of a chemiluminescent substrate and a colorimetric substrate.

20. The method of claim 19, wherein the substrate is a chemiluminescent substrate, and step v) comprises detecting a level of chemiluminescence in each capillary or population of capillaries.

21. The method of claim 20, wherein the chemiluminescent substrate is luminol, and wherein step iv) further comprises loading each capillary with peroxide.

22. The method of claim 1 wherein step i) comprises loading approximately 1-500 ng of biological sample.

23. The method of claim 22, wherein step i) comprises loading approximately 5-40 ng of biological sample.

24. The method of claim 1, wherein the biological sample is a bodily fluid.

25. The method of claim 24, wherein the bodily fluid is selected from the group consisting of blood, plasma, and serum.

26. The method of claim 1, wherein the biological sample is a diseased tissue.

27. The method of claim 26, wherein the diseased tissue is a lysate.

28. The method of claim 27, wherein the disease tissue is tumor tissue.

29. The method of claim 1, wherein the uncleaved activatable antibody has the structure from N-terminus to C-terminus as follows: MM-CM-AB or AB-CM-MM.

30. The method of claim 29, wherein the AB is linked directly to the CM, the CM is linked directly to the AB, or both.

31. The method of claim 29, wherein the AB is linked to the CM via a linking peptide, the CM is linked to the AB via a linking peptide, or both.

32. The method of claim 29, wherein the uncleaved activatable antibody comprises a first linking peptide (LP1) and a second linking peptide (LP2), and wherein the uncleaved activatable antibody has the structural arrangement from N-terminus to C-terminus as follows: MM-LP1-CM-LP2-AB or AB-LP2-CM-LP1-MM.

33. The method of claim 32, wherein the two linking peptides need not be identical to each other.

34. The method of claim 32, wherein each of LP1 and LP2 is a peptide of about 1 to 20 amino acids in length.

* * * * *

SEQUENCE LISTING

```
<160> NUMBER OF SEQ ID NOS: 1037

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8
```

-continued

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

-continued

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

-continued

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

-continued

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

-continued

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

-continued

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127
<211> LENGTH: 7
<212> TYPE: PRT
<213> ORGANISM: Homo sapiens

<400> SEQUENCE: 127

Ser Lys Ile Pro Pro Glu Asp
1               5

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

-continued

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

-continued

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

-continued

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

-continued

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223
<400> SEQUENCE: 223
000

<210> SEQ ID NO 224
<400> SEQUENCE: 224
000

<210> SEQ ID NO 225
<400> SEQUENCE: 225
000

<210> SEQ ID NO 226
<400> SEQUENCE: 226
000

<210> SEQ ID NO 227
<400> SEQUENCE: 227
000

<210> SEQ ID NO 228
<400> SEQUENCE: 228
000

<210> SEQ ID NO 229
<400> SEQUENCE: 229
000

<210> SEQ ID NO 230
<400> SEQUENCE: 230
000

<210> SEQ ID NO 231
<400> SEQUENCE: 231
000

<210> SEQ ID NO 232
<400> SEQUENCE: 232
000

<210> SEQ ID NO 233
<400> SEQUENCE: 233
000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

-continued

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

-continued

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339
<211> LENGTH: 100
<212> TYPE: PRT
<213> ORGANISM: Artificial Sequence
<220> FEATURE:
<223> OTHER INFORMATION: chemimcally synthesized
<220> FEATURE:
<221> NAME/KEY: MISC_FEATURE
<222> LOCATION: (6)..(100)
<223> OTHER INFORMATION: May be absent

<400> SEQUENCE: 339

```
Gly Ser Gly Gly Ser Gly Ser Gly Gly Ser Gly Ser Gly Gly Ser Gly
1               5                   10                  15

Ser Gly Gly Ser Gly Ser Gly Gly Ser Gly Ser Gly Gly Ser Gly Ser
            20                  25                  30

Gly Gly Ser Gly Ser Gly Gly Ser Gly Ser Gly Gly Ser Gly Ser Gly
        35                  40                  45

Gly Ser Gly Ser Gly Gly Ser Gly Ser Gly Gly Ser Gly Ser Gly Gly
    50                  55                  60

Ser Gly Ser Gly Gly Ser Gly Ser Gly Gly Ser Gly Ser Gly Gly Ser
65                  70                  75                  80

Gly Ser Gly Gly Ser Gly Ser Gly Gly Ser Gly Ser Gly Gly Ser Gly
                85                  90                  95

Ser Gly Gly Ser
            100
```

<210> SEQ ID NO 340
<211> LENGTH: 80
<212> TYPE: PRT
<213> ORGANISM: Artificial Sequence
<220> FEATURE:
<223> OTHER INFORMATION: chemimcally synthesized
<220> FEATURE:
<221> NAME/KEY: MISC_FEATURE
<222> LOCATION: (5)..(80)
<223> OTHER INFORMATION: May be absent

<400> SEQUENCE: 340

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30
```

```
Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80
```

<210> SEQ ID NO 341
<211> LENGTH: 4
<212> TYPE: PRT
<213> ORGANISM: Artificial Sequence
<220> FEATURE:
<223> OTHER INFORMATION: chemimcally synthesized

<400> SEQUENCE: 341

```
Gly Gly Ser Gly
1
```

<210> SEQ ID NO 342
<211> LENGTH: 5
<212> TYPE: PRT
<213> ORGANISM: Artificial Sequence
<220> FEATURE:
<223> OTHER INFORMATION: chemimcally synthesized

<400> SEQUENCE: 342

```
Gly Gly Ser Gly Gly
1               5
```

<210> SEQ ID NO 343
<211> LENGTH: 5
<212> TYPE: PRT
<213> ORGANISM: Artificial Sequence
<220> FEATURE:
<223> OTHER INFORMATION: chemimcally synthesized

<400> SEQUENCE: 343

```
Gly Ser Gly Ser Gly
1               5
```

<210> SEQ ID NO 344
<211> LENGTH: 5
<212> TYPE: PRT
<213> ORGANISM: Artificial Sequence
<220> FEATURE:
<223> OTHER INFORMATION: chemimcally synthesized

<400> SEQUENCE: 344

```
Gly Ser Gly Gly Gly
1               5
```

<210> SEQ ID NO 345
<211> LENGTH: 5
<212> TYPE: PRT
<213> ORGANISM: Artificial Sequence
<220> FEATURE:
<223> OTHER INFORMATION: chemimcally synthesized

<400> SEQUENCE: 345

```
Gly Gly Gly Ser Gly
1               5
```

<210> SEQ ID NO 346
<211> LENGTH: 5
<212> TYPE: PRT

-continued

<213> ORGANISM: Artificial Sequence
<220> FEATURE:
<223> OTHER INFORMATION: chemimcally synthesized

<400> SEQUENCE: 346

Gly Ser Ser Ser Gly
1 5

<210> SEQ ID NO 347
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 347

Gly Ser Ser Gly Gly Ser Gly Gly Ser Gly Gly Ser Gly
1 5 10

<210> SEQ ID NO 348
<211> LENGTH: 11
<212> TYPE: PRT
<213> ORGANISM: Artificial Sequence
<220> FEATURE:
<223> OTHER INFORMATION: chemimcally synthesized

<400> SEQUENCE: 348

Gly Ser Ser Gly Gly Ser Gly Gly Ser Gly Gly
1 5 10

<210> SEQ ID NO 349
<211> LENGTH: 12
<212> TYPE: PRT
<213> ORGANISM: Artificial Sequence
<220> FEATURE:
<223> OTHER INFORMATION: chemimcally synthesized

<400> SEQUENCE: 349

Gly Ser Ser Gly Gly Ser Gly Gly Ser Gly Gly Ser
1 5 10

<210> SEQ ID NO 350
<211> LENGTH: 16
<212> TYPE: PRT
<213> ORGANISM: Artificial Sequence
<220> FEATURE:
<223> OTHER INFORMATION: chemimcally synthesized

<400> SEQUENCE: 350

Gly Ser Ser Gly Gly Ser Gly Gly Ser Gly Gly Ser Gly Gly Gly Ser
1 5 10 15

<210> SEQ ID NO 351
<211> LENGTH: 10
<212> TYPE: PRT
<213> ORGANISM: Artificial Sequence
<220> FEATURE:
<223> OTHER INFORMATION: chemimcally synthesized

<400> SEQUENCE: 351

Gly Ser Ser Gly Gly Ser Gly Gly Ser Gly
1 5 10

<210> SEQ ID NO 352
<211> LENGTH: 11
<212> TYPE: PRT
<213> ORGANISM: Artificial Sequence
<220> FEATURE:
<223> OTHER INFORMATION: chemimcally synthesized

<400> SEQUENCE: 352

Gly Ser Ser Gly Gly Ser Gly Gly Ser Gly Ser
1 5 10

<210> SEQ ID NO 353
<211> LENGTH: 4
<212> TYPE: PRT
<213> ORGANISM: Artificial Sequence
<220> FEATURE:
<223> OTHER INFORMATION: chemimcally synthesized

<400> SEQUENCE: 353

Gly Gly Gly Ser
1

<210> SEQ ID NO 354
<211> LENGTH: 5
<212> TYPE: PRT
<213> ORGANISM: Artificial Sequence
<220> FEATURE:
<223> OTHER INFORMATION: chemimcally synthesized

<400> SEQUENCE: 354

Gly Ser Ser Gly Thr
1 5

<210> SEQ ID NO 355
<211> LENGTH: 4
<212> TYPE: PRT
<213> ORGANISM: Artificial Sequence
<220> FEATURE:
<223> OTHER INFORMATION: chemimcally synthesized

<400> SEQUENCE: 355

Gly Ser Ser Gly
1

<210> SEQ ID NO 356
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 356

Thr Gly Arg Gly Pro Ser Trp Val
1 5

<210> SEQ ID NO 357
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 357

Ser Ala Arg Gly Pro Ser Arg Trp
1 5

<210> SEQ ID NO 358
<211> LENGTH: 8
<212> TYPE: PRT
<213> ORGANISM: Artificial Sequence
<220> FEATURE:

<223> OTHER INFORMATION: chemimcally synthesized

<400> SEQUENCE: 358

Thr Ala Arg Gly Pro Ser Phe Lys
1               5

<210> SEQ ID NO 359
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 359

Leu Ser Gly Arg Ser Asp Asn His
1               5

<210> SEQ ID NO 360
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 360

Gly Gly Trp His Thr Gly Arg Asn
1               5

<210> SEQ ID NO 361
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 361

His Thr Gly Arg Ser Gly Ala Leu
1               5

<210> SEQ ID NO 362
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 362

Pro Leu Thr Gly Arg Ser Gly Gly
1               5

<210> SEQ ID NO 363
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 363

Ala Ala Arg Gly Pro Ala Ile His
1               5

<210> SEQ ID NO 364
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 364

Arg Gly Pro Ala Phe Asn Pro Met
1               5

<210> SEQ ID NO 365
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 365

Ser Ser Arg Gly Pro Ala Tyr Leu
1               5

<210> SEQ ID NO 366
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 366

Arg Gly Pro Ala Thr Pro Ile Met
1               5

<210> SEQ ID NO 367
<211> LENGTH: 4
<212> TYPE: PRT
<213> ORGANISM: Artificial Sequence
<220> FEATURE:
<223> OTHER INFORMATION: chemimcally synthesized

<400> SEQUENCE: 367

Arg Gly Pro Ala
1

<210> SEQ ID NO 368
<211> LENGTH: 10
<212> TYPE: PRT
<213> ORGANISM: Artificial Sequence
<220> FEATURE:
<223> OTHER INFORMATION: chemimcally synthesized

<400> SEQUENCE: 368

Gly Gly Gln Pro Ser Gly Met Trp Gly Trp
1               5                   10

<210> SEQ ID NO 369
<211> LENGTH: 10
<212> TYPE: PRT
<213> ORGANISM: Artificial Sequence
<220> FEATURE:
<223> OTHER INFORMATION: chemimcally synthesized

<400> SEQUENCE: 369

Phe Pro Arg Pro Leu Gly Ile Thr Gly Leu
1               5                   10

<210> SEQ ID NO 370
<211> LENGTH: 10
<212> TYPE: PRT
<213> ORGANISM: Artificial Sequence
<220> FEATURE:
<223> OTHER INFORMATION: chemimcally synthesized

<400> SEQUENCE: 370

Val His Met Pro Leu Gly Phe Leu Gly Pro
1 5 10

<210> SEQ ID NO 371
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 371

Ser Pro Leu Thr Gly Arg Ser Gly
1 5

<210> SEQ ID NO 372
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 372

Ser Ala Gly Phe Ser Leu Pro Ala
1 5

<210> SEQ ID NO 373
<211> LENGTH: 9
<212> TYPE: PRT
<213> ORGANISM: Artificial Sequence
<220> FEATURE:
<223> OTHER INFORMATION: chemimcally synthesized

<400> SEQUENCE: 373

Leu Ala Pro Leu Gly Leu Gln Arg Arg
1 5

<210> SEQ ID NO 374
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 374

Ser Gly Gly Pro Leu Gly Val Arg
1 5

<210> SEQ ID NO 375
<211> LENGTH: 4
<212> TYPE: PRT
<213> ORGANISM: Artificial Sequence
<220> FEATURE:
<223> OTHER INFORMATION: chemimcally synthesized

<400> SEQUENCE: 375

Pro Leu Gly Leu
1

<210> SEQ ID NO 376
<211> LENGTH: 7
<212> TYPE: PRT
<213> ORGANISM: Artificial Sequence
<220> FEATURE:
<223> OTHER INFORMATION: chemimcally synthesized

<400> SEQUENCE: 376

Ile Ser Ser Gly Leu Ser Ser
1               5

<210> SEQ ID NO 377
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 377

Gln Asn Gln Ala Leu Arg Met Ala
1               5

<210> SEQ ID NO 378
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 378

Ala Gln Asn Leu Leu Gly Met Val
1               5

<210> SEQ ID NO 379
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 379

Ser Thr Phe Pro Phe Gly Met Phe
1               5

<210> SEQ ID NO 380
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 380

Pro Val Gly Tyr Thr Ser Ser Leu
1               5

<210> SEQ ID NO 381
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 381

Asp Trp Leu Tyr Trp Pro Gly Ile
1               5

<210> SEQ ID NO 382
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 382

```
Ile Ser Ser Gly Leu Leu Ser Ser
1               5


<210> SEQ ID NO 383
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 383

Leu Lys Ala Ala Pro Arg Trp Ala
1               5


<210> SEQ ID NO 384
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 384

Gly Pro Ser His Leu Val Leu Thr
1               5


<210> SEQ ID NO 385
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 385

Leu Pro Gly Gly Leu Ser Pro Trp
1               5


<210> SEQ ID NO 386
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 386

Met Gly Leu Phe Ser Glu Ala Gly
1               5


<210> SEQ ID NO 387
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 387

Ser Pro Leu Pro Leu Arg Val Pro
1               5


<210> SEQ ID NO 388
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 388

Arg Met His Leu Arg Ser Leu Gly
```

1 5

<210> SEQ ID NO 389
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 389

Leu Ala Ala Pro Leu Gly Leu Leu
1 5

<210> SEQ ID NO 390
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 390

Ala Val Gly Leu Leu Ala Pro Pro
1 5

<210> SEQ ID NO 391
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 391

Leu Leu Ala Pro Ser His Arg Ala
1 5

<210> SEQ ID NO 392
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 392

Pro Ala Gly Leu Trp Leu Asp Pro
1 5

<210> SEQ ID NO 393
<211> LENGTH: 7
<212> TYPE: PRT
<213> ORGANISM: Artificial Sequence
<220> FEATURE:
<223> OTHER INFORMATION: chemimcally synthesized

<400> SEQUENCE: 393

Gly Pro Arg Ser Phe Gly Leu
1 5

<210> SEQ ID NO 394
<211> LENGTH: 6
<212> TYPE: PRT
<213> ORGANISM: Artificial Sequence
<220> FEATURE:
<223> OTHER INFORMATION: chemimcally synthesized

<400> SEQUENCE: 394

Gly Pro Arg Ser Phe Gly
1 5

<210> SEQ ID NO 395
<211> LENGTH: 12
<212> TYPE: PRT
<213> ORGANISM: Artificial Sequence
<220> FEATURE:
<223> OTHER INFORMATION: chemimcally synthesized

<400> SEQUENCE: 395

Asn Thr Leu Ser Gly Arg Ser Glu Asn His Ser Gly
1               5                   10

<210> SEQ ID NO 396
<211> LENGTH: 12
<212> TYPE: PRT
<213> ORGANISM: Artificial Sequence
<220> FEATURE:
<223> OTHER INFORMATION: chemimcally synthesized

<400> SEQUENCE: 396

Asn Thr Leu Ser Gly Arg Ser Gly Asn His Gly Ser
1               5                   10

<210> SEQ ID NO 397
<211> LENGTH: 12
<212> TYPE: PRT
<213> ORGANISM: Artificial Sequence
<220> FEATURE:
<223> OTHER INFORMATION: chemimcally synthesized

<400> SEQUENCE: 397

Thr Ser Thr Ser Gly Arg Ser Ala Asn Pro Arg Gly
1               5                   10

<210> SEQ ID NO 398
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 398

Thr Ser Gly Arg Ser Ala Asn Pro
1               5

<210> SEQ ID NO 399
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 399

Val Ala Gly Arg Ser Met Arg Pro
1               5

<210> SEQ ID NO 400
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 400

Val Val Pro Glu Gly Arg Arg Ser
1               5

<210> SEQ ID NO 401
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 401

Ile Leu Pro Arg Ser Pro Ala Phe
1               5

<210> SEQ ID NO 402
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 402

Met Val Leu Gly Arg Ser Leu Leu
1               5

<210> SEQ ID NO 403
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 403

Gln Gly Arg Ala Ile Thr Phe Ile
1               5

<210> SEQ ID NO 404
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 404

Ser Pro Arg Ser Ile Met Leu Ala
1               5

<210> SEQ ID NO 405
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 405

Ser Met Leu Arg Ser Met Pro Leu
1               5

<210> SEQ ID NO 406
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 406

Ile Ser Ser Gly Leu Leu Ser Gly Arg Ser Asp Asn His
1               5                   10

<210> SEQ ID NO 407
<211> LENGTH: 22
<212> TYPE: PRT
<213> ORGANISM: Artificial Sequence
<220> FEATURE:
<223> OTHER INFORMATION: chemimcally synthesized

<400> SEQUENCE: 407

Ile Ser Ser Gly Leu Leu Ser Ser Gly Gly Ser Gly Gly Ser Leu Ser
1 5 10 15

Gly Arg Ser Asp Asn His
20

<210> SEQ ID NO 408
<211> LENGTH: 22
<212> TYPE: PRT
<213> ORGANISM: Artificial Sequence
<220> FEATURE:
<223> OTHER INFORMATION: chemimcally synthesized

<400> SEQUENCE: 408

Ala Val Gly Leu Leu Ala Pro Pro Gly Gly Thr Ser Thr Ser Gly Arg
1 5 10 15

Ser Ala Asn Pro Arg Gly
20

<210> SEQ ID NO 409
<211> LENGTH: 22
<212> TYPE: PRT
<213> ORGANISM: Artificial Sequence
<220> FEATURE:
<223> OTHER INFORMATION: chemimcally synthesized

<400> SEQUENCE: 409

Thr Ser Thr Ser Gly Arg Ser Ala Asn Pro Arg Gly Gly Gly Ala Val
1 5 10 15

Gly Leu Leu Ala Pro Pro
20

<210> SEQ ID NO 410
<211> LENGTH: 24
<212> TYPE: PRT
<213> ORGANISM: Artificial Sequence
<220> FEATURE:
<223> OTHER INFORMATION: chemimcally synthesized

<400> SEQUENCE: 410

Val His Met Pro Leu Gly Phe Leu Gly Pro Gly Gly Thr Ser Thr Ser
1 5 10 15

Gly Arg Ser Ala Asn Pro Arg Gly
20

<210> SEQ ID NO 411
<211> LENGTH: 24
<212> TYPE: PRT
<213> ORGANISM: Artificial Sequence
<220> FEATURE:
<223> OTHER INFORMATION: chemimcally synthesized

<400> SEQUENCE: 411

Thr Ser Thr Ser Gly Arg Ser Ala Asn Pro Arg Gly Gly Gly Val His
1 5 10 15

Met Pro Leu Gly Phe Leu Gly Pro
20

<210> SEQ ID NO 412
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 412

Ala Val Gly Leu Leu Ala Pro Pro Gly Gly Leu Ser Gly Arg Ser Asp
1               5                   10                  15

Asn His

<210> SEQ ID NO 413
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 413

Leu Ser Gly Arg Ser Asp Asn His Gly Gly Ala Val Gly Leu Leu Ala
1               5                   10                  15

Pro Pro

<210> SEQ ID NO 414
<211> LENGTH: 20
<212> TYPE: PRT
<213> ORGANISM: Artificial Sequence
<220> FEATURE:
<223> OTHER INFORMATION: chemimcally synthesized

<400> SEQUENCE: 414

Val His Met Pro Leu Gly Phe Leu Gly Pro Gly Gly Leu Ser Gly Arg
1               5                   10                  15

Ser Asp Asn His
            20

<210> SEQ ID NO 415
<211> LENGTH: 20
<212> TYPE: PRT
<213> ORGANISM: Artificial Sequence
<220> FEATURE:
<223> OTHER INFORMATION: chemimcally synthesized

<400> SEQUENCE: 415

Leu Ser Gly Arg Ser Asp Asn His Gly Gly Val His Met Pro Leu Gly
1               5                   10                  15

Phe Leu Gly Pro
            20

<210> SEQ ID NO 416
<211> LENGTH: 22
<212> TYPE: PRT
<213> ORGANISM: Artificial Sequence
<220> FEATURE:
<223> OTHER INFORMATION: chemimcally synthesized

<400> SEQUENCE: 416

Leu Ser Gly Arg Ser Asp Asn His Gly Gly Ser Gly Gly Ser Ile Ser
1               5                   10                  15

Ser Gly Leu Leu Ser Ser
            20

-continued

<210> SEQ ID NO 417
<211> LENGTH: 22
<212> TYPE: PRT
<213> ORGANISM: Artificial Sequence
<220> FEATURE:
<223> OTHER INFORMATION: chemimcally synthesized

<400> SEQUENCE: 417

Leu Ser Gly Arg Ser Gly Asn His Gly Gly Ser Gly Gly Ser Ile Ser
1 5 10 15

Ser Gly Leu Leu Ser Ser
20

<210> SEQ ID NO 418
<211> LENGTH: 22
<212> TYPE: PRT
<213> ORGANISM: Artificial Sequence
<220> FEATURE:
<223> OTHER INFORMATION: chemimcally synthesized

<400> SEQUENCE: 418

Ile Ser Ser Gly Leu Leu Ser Ser Gly Gly Ser Gly Gly Ser Leu Ser
1 5 10 15

Gly Arg Ser Gly Asn His
20

<210> SEQ ID NO 419
<211> LENGTH: 22
<212> TYPE: PRT
<213> ORGANISM: Artificial Sequence
<220> FEATURE:
<223> OTHER INFORMATION: chemimcally synthesized

<400> SEQUENCE: 419

Leu Ser Gly Arg Ser Asp Asn His Gly Gly Ser Gly Gly Ser Gln Asn
1 5 10 15

Gln Ala Leu Arg Met Ala
20

<210> SEQ ID NO 420
<211> LENGTH: 22
<212> TYPE: PRT
<213> ORGANISM: Artificial Sequence
<220> FEATURE:
<223> OTHER INFORMATION: chemimcally synthesized

<400> SEQUENCE: 420

Gln Asn Gln Ala Leu Arg Met Ala Gly Gly Ser Gly Gly Ser Leu Ser
1 5 10 15

Gly Arg Ser Asp Asn His
20

<210> SEQ ID NO 421
<211> LENGTH: 22
<212> TYPE: PRT
<213> ORGANISM: Artificial Sequence
<220> FEATURE:
<223> OTHER INFORMATION: chemimcally synthesized

<400> SEQUENCE: 421

Leu Ser Gly Arg Ser Gly Asn His Gly Gly Ser Gly Gly Ser Gln Asn
1 5 10 15

Gln Ala Leu Arg Met Ala
20

<210> SEQ ID NO 422
<211> LENGTH: 22
<212> TYPE: PRT
<213> ORGANISM: Artificial Sequence
<220> FEATURE:
<223> OTHER INFORMATION: chemimcally synthesized

<400> SEQUENCE: 422

```
Gln Asn Gln Ala Leu Arg Met Ala Gly Gly Ser Gly Gly Ser Leu Ser
1               5                   10                  15

Gly Arg Ser Gly Asn His
            20
```

<210> SEQ ID NO 423
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 423

```
Ile Ser Ser Gly Leu Leu Ser Gly Arg Ser Gly Asn His
1               5                   10
```

<210> SEQ ID NO 424
<211> LENGTH: 6
<212> TYPE: PRT
<213> ORGANISM: Artificial Sequence
<220> FEATURE:
<223> OTHER INFORMATION: chemimcally synthesized

<400> SEQUENCE: 424

```
Gln Gly Gln Ser Gly Gln
1               5
```

<210> SEQ ID NO 425
<211> LENGTH: 442
<212> TYPE: PRT
<213> ORGANISM: Artificial Sequence
<220> FEATURE:
<223> OTHER INFORMATION: chemimcally synthesized

<400> SEQUENCE: 425

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Trp Arg Asn Gly Ile Val Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ala Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140
```

-continued

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440


<210> SEQ ID NO 426
<211> LENGTH: 264
<212> TYPE: PRT
<213> ORGANISM: Artificial Sequence
<220> FEATURE:
<223> OTHER INFORMATION: chemimcally synthesized

<400> SEQUENCE: 426

Gln Gly Gln Ser Gly Ser Gly Ile Ala Leu Cys Pro Ser His Phe Cys
1               5                   10                  15

Gln Leu Pro Gln Thr Gly Gly Gly Ser Ser Gly Gly Ser Gly Gly Ser
            20                  25                  30

Gly Gly Ile Ser Ser Gly Leu Leu Ser Gly Arg Ser Asp Asn His Gly
        35                  40                  45

Gly Ser Asp Ile Gln Met Thr Gln Ser Pro Ser Ser Leu Ser Ala Ser
    50                  55                  60
```

-continued

```
Val Gly Asp Arg Val Thr Ile Thr Cys Arg Ala Ser Gln Ser Ile Ser
65                  70                  75                  80

Ser Tyr Leu Asn Trp Tyr Gln Gln Lys Pro Gly Lys Ala Pro Lys Leu
                85                  90                  95

Leu Ile Tyr Ala Ala Ser Ser Leu Gln Ser Gly Val Pro Ser Arg Phe
            100                 105                 110

Ser Gly Ser Gly Ser Gly Thr Asp Phe Thr Leu Thr Ile Ser Ser Leu
        115                 120                 125

Gln Pro Glu Asp Phe Ala Thr Tyr Tyr Cys Gln Gln Asp Asn Gly Tyr
    130                 135                 140

Pro Ser Thr Phe Gly Gly Gly Thr Lys Val Glu Ile Lys Arg Thr Val
145                 150                 155                 160

Ala Ala Pro Ser Val Phe Ile Phe Pro Pro Ser Asp Glu Gln Leu Lys
                165                 170                 175

Ser Gly Thr Ala Ser Val Val Cys Leu Leu Asn Asn Phe Tyr Pro Arg
            180                 185                 190

Glu Ala Lys Val Gln Trp Lys Val Asp Asn Ala Leu Gln Ser Gly Asn
        195                 200                 205

Ser Gln Glu Ser Val Thr Glu Gln Asp Ser Lys Asp Ser Thr Tyr Ser
    210                 215                 220

Leu Ser Ser Thr Leu Thr Leu Ser Lys Ala Asp Tyr Glu Lys His Lys
225                 230                 235                 240

Val Tyr Ala Cys Glu Val Thr His Gln Gly Leu Ser Ser Pro Val Thr
                245                 250                 255

Lys Ser Phe Asn Arg Gly Glu Cys
            260


<210> SEQ ID NO 427
<211> LENGTH: 15
<212> TYPE: PRT
<213> ORGANISM: Artificial Sequence
<220> FEATURE:
<223> OTHER INFORMATION: chemimcally synthesized

<400> SEQUENCE: 427

Cys Gln Gln Asp Asn Gly Tyr Pro Ser Thr Phe Gly Gly Gly Thr
1               5                   10                  15


<210> SEQ ID NO 428
<211> LENGTH: 372
<212> TYPE: DNA
<213> ORGANISM: Artificial Sequence
<220> FEATURE:
<223> OTHER INFORMATION: chemimcally synthesized

<400> SEQUENCE: 428

gaggtgcagt tggtggagtc tgggggagac ttagtgaagc ctggagggtc cctgaaagtc      60

tcctgtgcag cctctggatt cactttcagt agttatggca tgtcttgggt tcgccagact     120

ccagacaaaa ggctggagtg ggtcgcaacc attagtccta gtggtatata cacctactat     180

ccagtcactg tgaaggggcg attcaccatc tccagagaca atgccaagaa caccctgtac     240

ctgcaaatga gcagtctgaa gtctgaggac acagccatgt atttctgtgc aagacaccat     300

ccaaactatg gtagtacgta cctgtattat attgattact ggggccaagg caccgctctc     360

acagtctcct ca                                                         372


<210> SEQ ID NO 429
<211> LENGTH: 124
```

```
<212> TYPE: PRT
<213> ORGANISM: Artificial Sequence
<220> FEATURE:
<223> OTHER INFORMATION: chemimcally synthesized

<400> SEQUENCE: 429

Glu Val Gln Leu Val Glu Ser Gly Gly Asp Leu Val Lys Pro Gly Gly
1               5                   10                  15

Ser Leu Lys Val Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Pro Ser Gly Ile Tyr Thr Tyr Tyr Pro Val Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Phe Cys
                85                  90                  95

Ala Arg His His Pro Asn Tyr Gly Ser Thr Tyr Leu Tyr Tyr Ile Asp
            100                 105                 110

Tyr Trp Gly Gln Gly Thr Ala Leu Thr Val Ser Ser
        115                 120


<210> SEQ ID NO 430
<211> LENGTH: 336
<212> TYPE: DNA
<213> ORGANISM: Artificial Sequence
<220> FEATURE:
<223> OTHER INFORMATION: chemimcally synthesized

<400> SEQUENCE: 430

aacattatga tgacacagtc gccatcatct ctggctgtgt ctgcaggaga aaaggtcact      60

atggcctgta agtccagtca aagtgttttt tccagttcaa atcagaagaa ctacttggcc     120

tggtaccagc agaaaccagg gcagtctcct aaaatactga tctactgggc tttcactagg     180

gaatctggtg tccctgaccg cttctcaggc agtggatctg ggacagattt tactcttacc     240

atcagcagtg tgcaagctga agacctggca gtttattact gttatcaata cctctcctca     300

ctcacgttcg gtgctgggac caagctggag gtgaaa                               336


<210> SEQ ID NO 431
<211> LENGTH: 112
<212> TYPE: PRT
<213> ORGANISM: Artificial Sequence
<220> FEATURE:
<223> OTHER INFORMATION: chemimcally synthesized

<400> SEQUENCE: 431

Asn Ile Met Met Thr Gln Ser Pro Ser Ser Leu Ala Val Ser Ala Gly
1               5                   10                  15

Glu Lys Val Thr Met Ala Cys Lys Ser Ser Gln Ser Val Phe Ser Ser
            20                  25                  30

Ser Asn Gln Lys Asn Tyr Leu Ala Trp Tyr Gln Gln Lys Pro Gly Gln
        35                  40                  45

Ser Pro Lys Ile Leu Ile Tyr Trp Ala Phe Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys Tyr Gln
```

-continued

```
                85                  90                  95

Tyr Leu Ser Ser Leu Thr Phe Gly Ala Gly Thr Lys Leu Glu Val Lys
            100                 105                 110


<210> SEQ ID NO 432
<211> LENGTH: 451
<212> TYPE: PRT
<213> ORGANISM: Artificial Sequence
<220> FEATURE:
<223> OTHER INFORMATION: chemimcally synthesized

<400> SEQUENCE: 432

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Ser Glu Asp Lys His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Val Gln Ile Asp Tyr Gly Asn Asp Tyr Ala Phe Thr Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

```
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 433
<211> LENGTH: 263
<212> TYPE: PRT
<213> ORGANISM: Artificial Sequence
<220> FEATURE:
<223> OTHER INFORMATION: chemimcally synthesized

<400> SEQUENCE: 433

Leu Cys His Pro Ala Val Leu Ser Ala Trp Glu Ser Cys Ser Ser Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Ser Asp Ile Val Met
        35                  40                  45

Thr Gln Ser Pro Leu Ser Leu Pro Val Thr Pro Gly Glu Pro Ala Ser
    50                  55                  60

Ile Ser Cys Arg Ser Ser Lys Ser Leu Leu His Ser Asn Gly Ile Thr
65                  70                  75                  80

Tyr Leu Tyr Trp Tyr Leu Gln Lys Pro Gly Gln Ser Pro Gln Leu Leu
                85                  90                  95

Ile Tyr Gln Met Ser Asn Leu Ala Ser Gly Val Pro Asp Arg Phe Ser
            100                 105                 110

Gly Ser Gly Ser Gly Thr Asp Phe Thr Leu Lys Ile Ser Arg Val Glu
        115                 120                 125

Ala Glu Asp Val Gly Val Tyr Tyr Cys Ala Gln Asn Leu Glu Leu Pro
    130                 135                 140

Tyr Thr Phe Gly Gln Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
```

-continued

```
                245                 250                 255

Ser Phe Asn Arg Gly Glu Cys
            260


<210> SEQ ID NO 434
<211> LENGTH: 448
<212> TYPE: PRT
<213> ORGANISM: Artificial Sequence
<220> FEATURE:
<223> OTHER INFORMATION: chemimcally synthesized

<400> SEQUENCE: 434

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Ala Ile Tyr Pro Gly Asn Ser Glu Thr Gly Tyr Ala Gln Lys Phe
    50                  55                  60

Gln Gly Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Asn Trp Asp Pro Gly Phe Ala Phe Trp Gly Gln Gly Thr
            100                 105                 110

Leu Ile Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
```

```
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 435
<211> LENGTH: 253
<212> TYPE: PRT
<213> ORGANISM: Artificial Sequence
<220> FEATURE:
<223> OTHER INFORMATION: chemimcally synthesized

<400> SEQUENCE: 435

Asn Leu Cys Thr Glu His Ser Ala Ala Leu Asp Cys Arg Ser Tyr Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Gln Met Thr Gln Ser Pro
        35                  40                  45

Ser Ser Leu Ser Ala Ser Val Gly Asp Arg Val Thr Ile Thr Cys Ser
    50                  55                  60

Ala Ser Ser Ser Val Tyr Tyr Met Tyr Trp Phe Gln Gln Lys Pro Gly
65                  70                  75                  80

Lys Ala Pro Lys Leu Trp Ile Tyr Ser Thr Ser Asn Leu Ala Ser Gly
                85                  90                  95

Val Pro Ser Arg Phe Ser Gly Ser Gly Ser Gly Thr Asp Tyr Thr Leu
            100                 105                 110

Thr Ile Ser Ser Met Gln Pro Glu Asp Phe Ala Thr Tyr Tyr Cys Gln
        115                 120                 125

Gln Arg Arg Asn Tyr Pro Tyr Thr Phe Gly Gln Gly Thr Lys Leu Glu
    130                 135                 140

Ile Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250
```

<210> SEQ ID NO 436
<211> LENGTH: 446
<212> TYPE: PRT
<213> ORGANISM: Artificial Sequence
<220> FEATURE:
<223> OTHER INFORMATION: chemimcally synthesized

<400> SEQUENCE: 436

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ala Tyr Ile Ser Asn Ser Gly Gly Asn Ala His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Asp Tyr Gly Thr Ser Pro Phe Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
```

```
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 437
<211> LENGTH: 258
<212> TYPE: PRT
<213> ORGANISM: Artificial Sequence
<220> FEATURE:
<223> OTHER INFORMATION: chemimcally synthesized

<400> SEQUENCE: 437

Thr Ser Tyr Cys Ser Ile Glu His Tyr Pro Cys Asn Thr His His Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Gln Leu Thr Gln Ser Pro
        35                  40                  45

Ser Ser Leu Ser Ala Ser Val Gly Asp Arg Val Thr Ile Thr Cys Arg
    50                  55                  60

Ala Ser Glu Ser Val Asp Ala Tyr Gly Ile Ser Phe Met Asn Trp Phe
65                  70                  75                  80

Gln Gln Lys Pro Gly Lys Ala Pro Lys Leu Leu Ile Tyr Ala Ala Ser
                85                  90                  95

Asn Gln Gly Ser Gly Val Pro Ser Arg Phe Ser Gly Ser Gly Ser Gly
            100                 105                 110

Thr Asp Phe Thr Leu Thr Ile Ser Ser Met Gln Pro Glu Asp Phe Ala
        115                 120                 125

Thr Tyr Tyr Cys Gln Gln Ser Lys Asp Val Pro Trp Thr Phe Gly Gln
    130                 135                 140

Gly Thr Lys Leu Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys


<210> SEQ ID NO 438
<211> LENGTH: 5
<212> TYPE: PRT
<213> ORGANISM: Artificial Sequence
```

<220> FEATURE:
<223> OTHER INFORMATION: chemimcally synthesized

<400> SEQUENCE: 438

Ser Tyr Gly Met Ser
1 5

<210> SEQ ID NO 439
<211> LENGTH: 17
<212> TYPE: PRT
<213> ORGANISM: Artificial Sequence
<220> FEATURE:
<223> OTHER INFORMATION: chemimcally synthesized

<400> SEQUENCE: 439

Thr Ile Ser Pro Ser Gly Ile Tyr Thr Tyr Tyr Pro Val Thr Val Lys
1 5 10 15

Gly

<210> SEQ ID NO 440
<211> LENGTH: 15
<212> TYPE: PRT
<213> ORGANISM: Artificial Sequence
<220> FEATURE:
<223> OTHER INFORMATION: chemimcally synthesized

<400> SEQUENCE: 440

His His Pro Asn Tyr Gly Ser Thr Tyr Leu Tyr Tyr Ile Asp Tyr
1 5 10 15

<210> SEQ ID NO 441
<211> LENGTH: 17
<212> TYPE: PRT
<213> ORGANISM: Artificial Sequence
<220> FEATURE:
<223> OTHER INFORMATION: chemimcally synthesized

<400> SEQUENCE: 441

Lys Ser Ser Gln Ser Val Phe Ser Ser Ser Asn Gln Lys Asn Tyr Leu
1 5 10 15

Ala

<210> SEQ ID NO 442
<211> LENGTH: 7
<212> TYPE: PRT
<213> ORGANISM: Artificial Sequence
<220> FEATURE:
<223> OTHER INFORMATION: chemimcally synthesized

<400> SEQUENCE: 442

Trp Ala Phe Thr Arg Glu Ser
1 5

<210> SEQ ID NO 443
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 443

Tyr Gln Tyr Leu Ser Ser Leu Thr
1 5

<210> SEQ ID NO 444

<211> LENGTH: 454
<212> TYPE: PRT
<213> ORGANISM: Artificial Sequence
<220> FEATURE:
<223> OTHER INFORMATION: chemimcally synthesized

<400> SEQUENCE: 444

Glu Val Gln Leu Val Glu Ser Gly Gly Asp Leu Val Lys Pro Gly Gly
1 5 10 15

Ser Leu Lys Val Ser Cys Ala Ala Ser Gly Phe Thr Phe Ser Ser Tyr
20 25 30

Gly Met Ser Trp Val Arg Gln Thr Pro Asp Lys Arg Leu Glu Trp Val
35 40 45

Ala Thr Ile Ser Pro Ser Gly Ile Tyr Thr Tyr Tyr Pro Val Thr Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr Phe Cys
85 90 95

Ala Arg His His Pro Asn Tyr Gly Ser Thr Tyr Leu Tyr Tyr Ile Asp
100 105 110

Tyr Trp Gly Gln Gly Thr Ala Leu Thr Val Ser Ser Ala Lys Thr Thr
115 120 125

Ala Pro Ser Val Tyr Pro Leu Ala Pro Val Cys Gly Asp Thr Thr Gly
130 135 140

Ser Ser Val Thr Leu Gly Cys Leu Val Lys Gly Tyr Phe Pro Glu Pro
145 150 155 160

Val Thr Leu Thr Trp Asn Ser Gly Ser Leu Ser Ser Gly Val His Thr
165 170 175

Phe Pro Ala Val Leu Gln Ser Asp Leu Tyr Thr Leu Ser Ser Ser Val
180 185 190

Thr Val Thr Ser Ser Thr Trp Pro Ser Gln Ser Ile Thr Cys Asn Val
195 200 205

Ala His Pro Ala Ser Ser Thr Lys Val Asp Lys Lys Ile Glu Pro Arg
210 215 220

Gly Pro Thr Ile Lys Pro Cys Pro Pro Cys Lys Cys Pro Ala Pro Asn
225 230 235 240

Leu Leu Gly Gly Pro Ser Val Phe Ile Phe Pro Pro Lys Ile Lys Asp
245 250 255

Val Leu Met Ile Ser Leu Ser Pro Ile Val Thr Cys Val Val Val Asp
260 265 270

Val Ser Glu Asp Asp Pro Asp Val Gln Ile Ser Trp Phe Val Asn Asn
275 280 285

Val Glu Val His Thr Ala Gln Thr Gln Thr His Arg Glu Asp Tyr Asn
290 295 300

Ser Thr Leu Arg Val Val Ser Ala Leu Pro Ile Gln His Gln Asp Trp
305 310 315 320

Met Ser Gly Lys Glu Phe Lys Cys Lys Val Asn Asn Lys Asp Leu Pro
325 330 335

Ala Pro Ile Glu Arg Thr Ile Ser Lys Pro Lys Gly Ser Val Arg Ala
340 345 350

Pro Gln Val Tyr Val Leu Pro Pro Pro Glu Glu Glu Met Thr Lys Lys
355 360 365

Gln Val Thr Leu Thr Cys Met Val Thr Asp Phe Met Pro Glu Asp Ile
370 375 380

```
Tyr Val Glu Trp Thr Asn Asn Gly Lys Thr Glu Leu Asn Tyr Lys Asn
385                 390                 395                 400

Thr Glu Pro Val Leu Asp Ser Asp Gly Ser Tyr Phe Met Tyr Ser Lys
                405                 410                 415

Leu Arg Val Glu Lys Lys Asn Trp Val Glu Arg Asn Ser Tyr Ser Cys
            420                 425                 430

Ser Val Val His Glu Gly Leu His Asn His His Thr Thr Lys Ser Phe
        435                 440                 445

Ser Arg Thr Pro Gly Lys
    450
```

```
<210> SEQ ID NO 445
<211> LENGTH: 218
<212> TYPE: PRT
<213> ORGANISM: Artificial Sequence
<220> FEATURE:
<223> OTHER INFORMATION: chemimcally synthesized

<400> SEQUENCE: 445

Asn Ile Met Met Thr Gln Ser Pro Ser Ser Leu Ala Val Ser Ala Gly
1               5                   10                  15

Glu Lys Val Thr Met Ala Cys Lys Ser Ser Gln Ser Val Phe Ser Ser
            20                  25                  30

Ser Asn Gln Lys Asn Tyr Leu Ala Trp Tyr Gln Gln Lys Pro Gly Gln
        35                  40                  45

Ser Pro Lys Ile Leu Ile Tyr Trp Ala Phe Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Leu Ala Val Tyr Tyr Cys Tyr Gln
                85                  90                  95

Tyr Leu Ser Ser Leu Thr Phe Gly Ala Gly Thr Lys Leu Glu Val Lys
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

```
<210> SEQ ID NO 446
<211> LENGTH: 449
<212> TYPE: PRT
<213> ORGANISM: Artificial Sequence
<220> FEATURE:
<223> OTHER INFORMATION: chemimcally synthesized

<400> SEQUENCE: 446

Gln Val Gln Leu Lys Gln Ser Gly Pro Gly Leu Val Gln Pro Ser Gln
```

-continued

```
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
435 440 445

Lys

<210> SEQ ID NO 447
<211> LENGTH: 214
<212> TYPE: PRT
<213> ORGANISM: Artificial Sequence
<220> FEATURE:
<223> OTHER INFORMATION: chemimcally synthesized

<400> SEQUENCE: 447

Gln Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Asn Asn Asn Trp Pro Thr
85 90 95

Thr Phe Gly Ala Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 448
<211> LENGTH: 15
<212> TYPE: PRT
<213> ORGANISM: Artificial Sequence
<220> FEATURE:
<223> OTHER INFORMATION: chemimcally synthesized

<400> SEQUENCE: 448

Cys Ile Ser Pro Arg Gly Cys Pro Asp Gly Pro Tyr Val Met Tyr
1 5 10 15

<210> SEQ ID NO 449
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 449

Gly Gly Gly Ser Ser Gly Gly Ser
1               5

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

-continued

000

<210> SEQ ID NO 461
<400> SEQUENCE: 461
000

<210> SEQ ID NO 462
<400> SEQUENCE: 462
000

<210> SEQ ID NO 463
<400> SEQUENCE: 463
000

<210> SEQ ID NO 464
<400> SEQUENCE: 464
000

<210> SEQ ID NO 465
<400> SEQUENCE: 465
000

<210> SEQ ID NO 466
<400> SEQUENCE: 466
000

<210> SEQ ID NO 467
<400> SEQUENCE: 467
000

<210> SEQ ID NO 468
<400> SEQUENCE: 468
000

<210> SEQ ID NO 469
<400> SEQUENCE: 469
000

<210> SEQ ID NO 470
<400> SEQUENCE: 470
000

<210> SEQ ID NO 471
<400> SEQUENCE: 471
000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

-continued

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501

<400> SEQUENCE: 501

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

-continued

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

-continued

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

-continued

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

-continued

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 615

Pro Arg Phe Lys Ile Ile Gly Gly
1               5

<210> SEQ ID NO 616
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 616

Pro Arg Phe Arg Ile Ile Gly Gly
1               5

<210> SEQ ID NO 617
<211> LENGTH: 9
<212> TYPE: PRT
<213> ORGANISM: Artificial Sequence
<220> FEATURE:
<223> OTHER INFORMATION: chemimcally synthesized

<400> SEQUENCE: 617

Ser Ser Arg His Arg Arg Ala Leu Asp
1               5

<210> SEQ ID NO 618
<211> LENGTH: 14
<212> TYPE: PRT
<213> ORGANISM: Artificial Sequence
<220> FEATURE:
<223> OTHER INFORMATION: chemimcally synthesized

<400> SEQUENCE: 618

Arg Lys Ser Ser Ile Ile Ile Arg Met Arg Asp Val Val Leu
1               5                   10

<210> SEQ ID NO 619
<211> LENGTH: 15
<212> TYPE: PRT
<213> ORGANISM: Artificial Sequence
<220> FEATURE:
<223> OTHER INFORMATION: chemimcally synthesized

<400> SEQUENCE: 619

Ser Ser Ser Phe Asp Lys Gly Lys Tyr Lys Lys Gly Asp Asp Ala
1               5                   10                  15

<210> SEQ ID NO 620
<211> LENGTH: 15
<212> TYPE: PRT
<213> ORGANISM: Artificial Sequence
<220> FEATURE:
<223> OTHER INFORMATION: chemimcally synthesized

<400> SEQUENCE: 620

Ser Ser Ser Phe Asp Lys Gly Lys Tyr Lys Arg Gly Asp Asp Ala
1               5                   10                  15

<210> SEQ ID NO 621
<211> LENGTH: 4
<212> TYPE: PRT
<213> ORGANISM: Artificial Sequence
<220> FEATURE:
<223> OTHER INFORMATION: chemimcally synthesized

<400> SEQUENCE: 621

Ile Glu Gly Arg
1

<210> SEQ ID NO 622
<211> LENGTH: 4
<212> TYPE: PRT
<213> ORGANISM: Artificial Sequence
<220> FEATURE:
<223> OTHER INFORMATION: chemimcally synthesized

<400> SEQUENCE: 622

Ile Asp Gly Arg
1

-continued

<210> SEQ ID NO 623
<211> LENGTH: 7
<212> TYPE: PRT
<213> ORGANISM: Artificial Sequence
<220> FEATURE:
<223> OTHER INFORMATION: chemimcally synthesized

<400> SEQUENCE: 623

Gly Gly Ser Ile Asp Gly Arg
1               5

<210> SEQ ID NO 624
<211> LENGTH: 6
<212> TYPE: PRT
<213> ORGANISM: Artificial Sequence
<220> FEATURE:
<223> OTHER INFORMATION: chemimcally synthesized

<400> SEQUENCE: 624

Pro Leu Gly Leu Trp Ala
1               5

<210> SEQ ID NO 625
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 625

Gly Pro Gln Gly Ile Ala Gly Gln
1               5

<210> SEQ ID NO 626
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 626

Gly Pro Gln Gly Leu Leu Gly Ala
1               5

<210> SEQ ID NO 627
<211> LENGTH: 5
<212> TYPE: PRT
<213> ORGANISM: Artificial Sequence
<220> FEATURE:
<223> OTHER INFORMATION: chemimcally synthesized

<400> SEQUENCE: 627

Gly Ile Ala Gly Gln
1               5

<210> SEQ ID NO 628
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 628

Gly Pro Leu Gly Ile Ala Gly Ile
1               5

-continued

<210> SEQ ID NO 629
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 629

Gly Pro Glu Gly Leu Arg Val Gly
1               5

<210> SEQ ID NO 630
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 630

Tyr Gly Ala Gly Leu Gly Val Val
1               5

<210> SEQ ID NO 631
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 631

Ala Gly Leu Gly Val Val Glu Arg
1               5

<210> SEQ ID NO 632
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 632

Ala Gly Leu Gly Ile Ser Ser Thr
1               5

<210> SEQ ID NO 633
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 633

Glu Pro Gln Ala Leu Ala Met Ser
1               5

<210> SEQ ID NO 634
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 634

Gln Ala Leu Ala Met Ser Ala Ile
1               5

<210> SEQ ID NO 635

<211> LENGTH: 8
<212> TYPE: PRT
<213> ORGANISM: Artificial Sequence
<220> FEATURE:
<223> OTHER INFORMATION: chemimcally synthesized

<400> SEQUENCE: 635

Ala Ala Tyr His Leu Val Ser Gln
1               5

<210> SEQ ID NO 636
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 636

Met Asp Ala Phe Leu Glu Ser Ser
1               5

<210> SEQ ID NO 637
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 637

Glu Ser Leu Pro Val Val Ala Val
1               5

<210> SEQ ID NO 638
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 638

Ser Ala Pro Ala Val Glu Ser Glu
1               5

<210> SEQ ID NO 639
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 639

Asp Val Ala Gln Phe Val Leu Thr
1               5

<210> SEQ ID NO 640
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 640

Val Ala Gln Phe Val Leu Thr Glu
1               5

<210> SEQ ID NO 641
<211> LENGTH: 8

<212> TYPE: PRT
<213> ORGANISM: Artificial Sequence
<220> FEATURE:
<223> OTHER INFORMATION: chemimcally synthesized

<400> SEQUENCE: 641

Ala Gln Phe Val Leu Thr Glu Gly
1 5

<210> SEQ ID NO 642
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 642

Pro Val Gln Pro Ile Gly Pro Gln
1 5

<210> SEQ ID NO 643
<211> LENGTH: 273
<212> TYPE: PRT
<213> ORGANISM: Artificial Sequence
<220> FEATURE:
<223> OTHER INFORMATION: chemimcally synthesized

<400> SEQUENCE: 643

Gly Gly Gly Ser Gly Gly Gly Gly Ser Gly Ser Gly Gly Gly Ser Gly
1 5 10 15

Gly Gly Gly Ser Gly Gly Gly Glu Ile Val Leu Thr Gln Ser Pro Gly
20 25 30

Thr Leu Ser Leu Ser Pro Gly Glu Arg Ala Thr Leu Ser Cys Arg Ala
35 40 45

Ser Gln Ser Val Ser Ser Ser Tyr Leu Ala Trp Tyr Gln Gln Lys Pro
50 55 60

Gly Gln Ala Pro Arg Leu Leu Ile Tyr Gly Ala Ser Ser Arg Ala Thr
65 70 75 80

Gly Ile Pro Asp Arg Phe Ser Gly Ser Gly Ser Gly Thr Asp Phe Thr
85 90 95

Leu Thr Ile Ser Arg Leu Glu Pro Glu Asp Phe Ala Val Tyr Tyr Cys
100 105 110

Gln Gln Tyr Gly Ser Ser Pro Leu Thr Phe Gly Gly Gly Thr Lys Val
115 120 125

Glu Ile Lys Arg Ser Gly Gly Ser Thr Ile Thr Ser Tyr Asn Val Tyr
130 135 140

Tyr Thr Lys Leu Ser Ser Ser Gly Thr Gln Val Gln Leu Val Gln Thr
145 150 155 160

Gly Gly Gly Val Val Gln Pro Gly Arg Ser Leu Arg Leu Ser Cys Ala
165 170 175

Ala Ser Gly Ser Thr Phe Ser Ser Tyr Ala Met Ser Trp Val Arg Gln
180 185 190

Ala Pro Gly Lys Gly Leu Glu Trp Val Ser Ala Ile Ser Gly Ser Gly
195 200 205

Gly Ser Thr Tyr Tyr Ala Asp Ser Val Lys Gly Arg Phe Thr Ile Ser
210 215 220

Arg Asp Asn Ser Lys Asn Thr Leu Tyr Leu Gln Met Asn Ser Leu Arg
225 230 235 240

Ala Glu Asp Thr Ala Val Tyr Tyr Cys Ala Thr Asn Ser Leu Tyr Trp 245 250 255

Tyr Phe Asp Leu Trp Gly Arg Gly Thr Leu Val Thr Val Ser Ser Ala
260 265 270

Ser

<210> SEQ ID NO 644
<211> LENGTH: 264
<212> TYPE: PRT
<213> ORGANISM: Artificial Sequence
<220> FEATURE:
<223> OTHER INFORMATION: chemimcally synthesized

<400> SEQUENCE: 644

Gly Gly Gly Ser Gly Gly Gly Gly Ser Gly Ser Gly Gly Gly Ser Gly
1 5 10 15

Gly Gly Gly Ser Gly Gly Gly Gln Val Gln Leu Gln Gln Ser Gly Ala
20 25 30

Glu Leu Ala Arg Pro Gly Ala Ser Val Lys Met Ser Cys Lys Ala Ser
35 40 45

Gly Tyr Thr Phe Thr Arg Tyr Thr Met His Trp Val Lys Gln Arg Pro
50 55 60

Gly Gln Gly Leu Glu Trp Ile Gly Tyr Ile Asn Pro Ser Arg Gly Tyr
65 70 75 80

Thr Asn Tyr Asn Gln Lys Phe Lys Asp Lys Ala Thr Leu Thr Thr Asp
85 90 95

Lys Ser Ser Ser Thr Ala Tyr Met Gln Leu Ser Ser Leu Thr Ser Glu
100 105 110

Asp Ser Ala Val Tyr Tyr Cys Ala Arg Tyr Tyr Asp Asp His Tyr Cys
115 120 125

Leu Asp Tyr Trp Gly Gln Gly Thr Thr Leu Thr Val Ser Ser Gly Gly
130 135 140

Gly Gly Ser Gly Gly Gly Gly Ser Gly Gly Gly Gly Ser Gln Ile Val
145 150 155 160

Leu Thr Gln Ser Pro Ala Ile Met Ser Ala Ser Pro Gly Glu Lys Val
165 170 175

Thr Met Thr Cys Ser Ala Ser Ser Ser Val Ser Tyr Met Asn Trp Tyr
180 185 190

Gln Gln Lys Ser Gly Thr Ser Pro Lys Arg Trp Ile Tyr Asp Thr Ser
195 200 205

Lys Leu Ala Ser Gly Val Pro Ala His Phe Arg Gly Ser Gly Ser Gly
210 215 220

Thr Ser Tyr Ser Leu Thr Ile Ser Gly Met Glu Ala Glu Asp Ala Ala
225 230 235 240

Thr Tyr Tyr Cys Gln Gln Trp Ser Ser Asn Pro Phe Thr Phe Gly Ser
245 250 255

Gly Thr Lys Leu Glu Ile Asn Arg
260

<210> SEQ ID NO 645
<211> LENGTH: 7
<212> TYPE: PRT
<213> ORGANISM: Artificial Sequence
<220> FEATURE:
<223> OTHER INFORMATION: chemimcally synthesized

<400> SEQUENCE: 645

Gln Gly Gln Ser Gly Gln Gly 1 5

<210> SEQ ID NO 646
<211> LENGTH: 5
<212> TYPE: PRT
<213> ORGANISM: Artificial Sequence
<220> FEATURE:
<223> OTHER INFORMATION: chemimcally synthesized

<400> SEQUENCE: 646

Gln Gly Gln Ser Gly
1 5

<210> SEQ ID NO 647
<211> LENGTH: 4
<212> TYPE: PRT
<213> ORGANISM: Artificial Sequence
<220> FEATURE:
<223> OTHER INFORMATION: chemimcally synthesized

<400> SEQUENCE: 647

Gln Gly Gln Ser
1

<210> SEQ ID NO 648
<211> LENGTH: 3
<212> TYPE: PRT
<213> ORGANISM: Artificial Sequence
<220> FEATURE:
<223> OTHER INFORMATION: chemimcally synthesized

<400> SEQUENCE: 648

Gln Gly Gln
1

<210> SEQ ID NO 649
<211> LENGTH: 2
<212> TYPE: PRT
<213> ORGANISM: Artificial Sequence
<220> FEATURE:
<223> OTHER INFORMATION: chemimcally synthesized

<400> SEQUENCE: 649

Gln Gly
1

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

-continued

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666
<211> LENGTH: 6
<212> TYPE: PRT
<213> ORGANISM: Artificial Sequence
<220> FEATURE:
<223> OTHER INFORMATION: chemimcally synthesized

<400> SEQUENCE: 666

Gly Gln Ser Gly Gln Gly
1               5

<210> SEQ ID NO 667
<211> LENGTH: 5
<212> TYPE: PRT
<213> ORGANISM: Artificial Sequence
<220> FEATURE:
<223> OTHER INFORMATION: chemimcally synthesized

<400> SEQUENCE: 667

Gln Ser Gly Gln Gly
1               5

<210> SEQ ID NO 668
<211> LENGTH: 4
<212> TYPE: PRT
<213> ORGANISM: Artificial Sequence
<220> FEATURE:
<223> OTHER INFORMATION: chemimcally synthesized

<400> SEQUENCE: 668

Ser Gly Gln Gly
1

<210> SEQ ID NO 669
<211> LENGTH: 3
<212> TYPE: PRT
<213> ORGANISM: Artificial Sequence
<220> FEATURE:
<223> OTHER INFORMATION: chemimcally synthesized

<400> SEQUENCE: 669

Gly Gln Gly
1

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680
<211> LENGTH: 15
<212> TYPE: PRT
<213> ORGANISM: Artificial Sequence
<220> FEATURE:
<223> OTHER INFORMATION: chemimcally synthesized

<400> SEQUENCE: 680

```
Ile Ser Ser Gly Leu Leu Ser Gly Arg Ser Ala Asn Pro Arg Gly
1               5                   10                  15
```

<210> SEQ ID NO 681
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 681

```
Ala Val Gly Leu Leu Ala Pro Pro Thr Ser Gly Arg Ser Ala Asn Pro
1               5                   10                  15

Arg Gly
```

<210> SEQ ID NO 682
<211> LENGTH: 17
<212> TYPE: PRT
<213> ORGANISM: Artificial Sequence
<220> FEATURE:
<223> OTHER INFORMATION: chemimcally synthesized

<400> SEQUENCE: 682

Ala Val Gly Leu Leu Ala Pro Pro Ser Gly Arg Ser Ala Asn Pro Arg
1 5 10 15

Gly

<210> SEQ ID NO 683
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 683

Ile Ser Ser Gly Leu Leu Ser Gly Arg Ser Asp Asp His
1 5 10

<210> SEQ ID NO 684
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 684

Ile Ser Ser Gly Leu Leu Ser Gly Arg Ser Asp Ile His
1 5 10

<210> SEQ ID NO 685
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 685

Ile Ser Ser Gly Leu Leu Ser Gly Arg Ser Asp Gln His
1 5 10

<210> SEQ ID NO 686
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 686

Ile Ser Ser Gly Leu Leu Ser Gly Arg Ser Asp Thr His
1 5 10

<210> SEQ ID NO 687
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 687

Ile Ser Ser Gly Leu Leu Ser Gly Arg Ser Asp Tyr His
1 5 10

-continued

<210> SEQ ID NO 688
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 688

Ile Ser Ser Gly Leu Leu Ser Gly Arg Ser Asp Asn Pro
1 5 10

<210> SEQ ID NO 689
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 689

Ile Ser Ser Gly Leu Leu Ser Gly Arg Ser Ala Asn Pro
1 5 10

<210> SEQ ID NO 690
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 690

Ile Ser Ser Gly Leu Leu Ser Gly Arg Ser Ala Asn Ile
1 5 10

<210> SEQ ID NO 691
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 691

Ala Val Gly Leu Leu Ala Pro Pro Gly Gly Leu Ser Gly Arg Ser Asp
1 5 10 15

Asp His

<210> SEQ ID NO 692
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 692

Ala Val Gly Leu Leu Ala Pro Pro Gly Gly Leu Ser Gly Arg Ser Asp
1 5 10 15

Ile His

<210> SEQ ID NO 693
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 693

Ala Val Gly Leu Leu Ala Pro Pro Gly Gly Leu Ser Gly Arg Ser Asp
1 5 10 15

Gln His

<210> SEQ ID NO 694
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 694

Ala Val Gly Leu Leu Ala Pro Pro Gly Gly Leu Ser Gly Arg Ser Asp
1 5 10 15

Thr His

<210> SEQ ID NO 695
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 695

Ala Val Gly Leu Leu Ala Pro Pro Gly Gly Leu Ser Gly Arg Ser Asp
1 5 10 15

Tyr His

<210> SEQ ID NO 696
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 696

Ala Val Gly Leu Leu Ala Pro Pro Gly Gly Leu Ser Gly Arg Ser Asp
1 5 10 15

Asn Pro

<210> SEQ ID NO 697
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 697

Ala Val Gly Leu Leu Ala Pro Pro Gly Gly Leu Ser Gly Arg Ser Ala
1 5 10 15

Asn Pro

<210> SEQ ID NO 698
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 698

Ala Val Gly Leu Leu Ala Pro Pro Gly Gly Leu Ser Gly Arg Ser Ala
1 5 10 15

Asn Ile

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713
<211> LENGTH: 13
<212> TYPE: PRT
<213> ORGANISM: Artificial Sequence
<220> FEATURE:
<223> OTHER INFORMATION: chemimcally synthesized

<400> SEQUENCE: 713

Ile Ser Ser Gly Leu Leu Ser Gly Arg Ser Asp Asn Ile
1               5                   10

<210> SEQ ID NO 714
<211> LENGTH: 18
<212> TYPE: PRT
<213> ORGANISM: Artificial Sequence
<220> FEATURE:
<223> OTHER INFORMATION: chemimcally synthesized

<400> SEQUENCE: 714

Ala Val Gly Leu Leu Ala Pro Pro Gly Gly Leu Ser Gly Arg Ser Asp
1               5                   10                  15

Asn Ile

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

-continued

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

<400> SEQUENCE: 759

000

<210> SEQ ID NO 760

<400> SEQUENCE: 760

000

<210> SEQ ID NO 761

<400> SEQUENCE: 761

000

<210> SEQ ID NO 762

<400> SEQUENCE: 762

000

<210> SEQ ID NO 763

<400> SEQUENCE: 763

000

<210> SEQ ID NO 764

<400> SEQUENCE: 764

000

<210> SEQ ID NO 765

<400> SEQUENCE: 765

000

<210> SEQ ID NO 766

<400> SEQUENCE: 766

000

<210> SEQ ID NO 767

<400> SEQUENCE: 767

000

<210> SEQ ID NO 768

<400> SEQUENCE: 768

000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 789

Leu Ser Gly Arg Ser Gly Asn His
1               5

<210> SEQ ID NO 790
<211> LENGTH: 9
<212> TYPE: PRT
<213> ORGANISM: Artificial Sequence
<220> FEATURE:
<223> OTHER INFORMATION: chemimcally synthesized

<400> SEQUENCE: 790

Ser Gly Arg Ser Ala Asn Pro Arg Gly
1               5

<210> SEQ ID NO 791
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 791

Leu Ser Gly Arg Ser Asp Asp His
1               5

<210> SEQ ID NO 792
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 792

Leu Ser Gly Arg Ser Asp Ile His
1               5

<210> SEQ ID NO 793
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 793

Leu Ser Gly Arg Ser Asp Gln His
1               5

<210> SEQ ID NO 794
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 794

Leu Ser Gly Arg Ser Asp Thr His
1 5

<210> SEQ ID NO 795
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 795

Leu Ser Gly Arg Ser Asp Tyr His
1 5

<210> SEQ ID NO 796
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 796

Leu Ser Gly Arg Ser Asp Asn Pro
1 5

<210> SEQ ID NO 797
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 797

Leu Ser Gly Arg Ser Ala Asn Pro
1 5

<210> SEQ ID NO 798
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 798

Leu Ser Gly Arg Ser Ala Asn Ile
1 5

<210> SEQ ID NO 799
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 799

Leu Ser Gly Arg Ser Asp Asn Ile
1 5

<210> SEQ ID NO 800
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 800

Met Ile Ala Pro Val Ala Tyr Arg
1               5

<210> SEQ ID NO 801
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 801

Arg Pro Ser Pro Met Trp Ala Tyr
1               5

<210> SEQ ID NO 802
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 802

Trp Ala Thr Pro Arg Pro Met Arg
1               5

<210> SEQ ID NO 803
<211> LENGTH: 8
<212> TYPE: PRT
<213> ORGANISM: Artificial Sequence
<220> FEATURE:
<223> OTHER INFORMATION: chemimcally synthesized

<400> SEQUENCE: 803

Phe Arg Leu Leu Asp Trp Gln Trp
1               5

<210> SEQ ID NO 804
<211> LENGTH: 5
<212> TYPE: PRT
<213> ORGANISM: Artificial Sequence
<220> FEATURE:
<223> OTHER INFORMATION: chemimcally synthesized

<400> SEQUENCE: 804

Ile Ser Ser Gly Leu
1               5

<210> SEQ ID NO 805
<211> LENGTH: 7
<212> TYPE: PRT
<213> ORGANISM: Artificial Sequence
<220> FEATURE:
<223> OTHER INFORMATION: chemimcally synthesized

<400> SEQUENCE: 805

Ile Ser Ser Gly Leu Leu Ser
1               5

<210> SEQ ID NO 806

<211> LENGTH: 6
<212> TYPE: PRT
<213> ORGANISM: Artificial Sequence
<220> FEATURE:
<223> OTHER INFORMATION: chemimcally synthesized

<400> SEQUENCE: 806

Ile Ser Ser Gly Leu Leu
1 5

<210> SEQ ID NO 807
<211> LENGTH: 19
<212> TYPE: PRT
<213> ORGANISM: Artificial Sequence
<220> FEATURE:
<223> OTHER INFORMATION: chemimcally synthesized

<400> SEQUENCE: 807

Gly Leu Ser Gly Arg Ser Asp Asn His Gly Gly Ala Val Gly Leu Leu
1 5 10 15

Ala Pro Pro

<210> SEQ ID NO 808
<211> LENGTH: 21
<212> TYPE: PRT
<213> ORGANISM: Artificial Sequence
<220> FEATURE:
<223> OTHER INFORMATION: chemimcally synthesized

<400> SEQUENCE: 808

Gly Leu Ser Gly Arg Ser Asp Asn His Gly Gly Val His Met Pro Leu
1 5 10 15

Gly Phe Leu Gly Pro
20

<210> SEQ ID NO 809

<400> SEQUENCE: 809

000

<210> SEQ ID NO 810

<400> SEQUENCE: 810

000

<210> SEQ ID NO 811

<400> SEQUENCE: 811

000

<210> SEQ ID NO 812

<400> SEQUENCE: 812

000

<210> SEQ ID NO 813

<400> SEQUENCE: 813

000

<210> SEQ ID NO 814

<400> SEQUENCE: 814

000

<210> SEQ ID NO 815

<400> SEQUENCE: 815

000

<210> SEQ ID NO 816

<400> SEQUENCE: 816

000

<210> SEQ ID NO 817

<400> SEQUENCE: 817

000

<210> SEQ ID NO 818

<400> SEQUENCE: 818

000

<210> SEQ ID NO 819

<400> SEQUENCE: 819

000

<210> SEQ ID NO 820

<400> SEQUENCE: 820

000

<210> SEQ ID NO 821

<400> SEQUENCE: 821

000

<210> SEQ ID NO 822

<400> SEQUENCE: 822

000

<210> SEQ ID NO 823

<400> SEQUENCE: 823

000

<210> SEQ ID NO 824

<400> SEQUENCE: 824

000

<210> SEQ ID NO 825

<400> SEQUENCE: 825

-continued

000

<210> SEQ ID NO 826

<400> SEQUENCE: 826

000

<210> SEQ ID NO 827

<400> SEQUENCE: 827

000

<210> SEQ ID NO 828

<400> SEQUENCE: 828

000

<210> SEQ ID NO 829

<400> SEQUENCE: 829

000

<210> SEQ ID NO 830

<400> SEQUENCE: 830

000

<210> SEQ ID NO 831

<400> SEQUENCE: 831

000

<210> SEQ ID NO 832

<400> SEQUENCE: 832

000

<210> SEQ ID NO 833

<400> SEQUENCE: 833

000

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879

<400> SEQUENCE: 879

000

<210> SEQ ID NO 880

<400> SEQUENCE: 880

000

<210> SEQ ID NO 881

<400> SEQUENCE: 881

000

<210> SEQ ID NO 882

<400> SEQUENCE: 882

000

<210> SEQ ID NO 883

<400> SEQUENCE: 883

000

<210> SEQ ID NO 884

<400> SEQUENCE: 884

000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901

<400> SEQUENCE: 901

000

<210> SEQ ID NO 902

<400> SEQUENCE: 902

000

<210> SEQ ID NO 903

<400> SEQUENCE: 903

000

<210> SEQ ID NO 904

<400> SEQUENCE: 904

000

<210> SEQ ID NO 905

<400> SEQUENCE: 905

000

<210> SEQ ID NO 906

<400> SEQUENCE: 906

000

<210> SEQ ID NO 907

<400> SEQUENCE: 907

000

<210> SEQ ID NO 908

<400> SEQUENCE: 908

000

<210> SEQ ID NO 909

<400> SEQUENCE: 909

000

<210> SEQ ID NO 910

<400> SEQUENCE: 910

000

<210> SEQ ID NO 911

<400> SEQUENCE: 911

000

<210> SEQ ID NO 912

<400> SEQUENCE: 912

000

<210> SEQ ID NO 913

<400> SEQUENCE: 913

000

<210> SEQ ID NO 914

<400> SEQUENCE: 914

000

<210> SEQ ID NO 915

<400> SEQUENCE: 915

000

<210> SEQ ID NO 916

<400> SEQUENCE: 916

000

<210> SEQ ID NO 917

<400> SEQUENCE: 917

000

<210> SEQ ID NO 918

<400> SEQUENCE: 918

000

<210> SEQ ID NO 919

<400> SEQUENCE: 919

000

<210> SEQ ID NO 920

<400> SEQUENCE: 920

000

<210> SEQ ID NO 921

<400> SEQUENCE: 921

000

<210> SEQ ID NO 922

<400> SEQUENCE: 922

000

<210> SEQ ID NO 923

<400> SEQUENCE: 923

000

<210> SEQ ID NO 924

<400> SEQUENCE: 924

000

<210> SEQ ID NO 925

<400> SEQUENCE: 925

000

<210> SEQ ID NO 926

<400> SEQUENCE: 926

000

-continued

<210> SEQ ID NO 927

<400> SEQUENCE: 927

000

<210> SEQ ID NO 928

<400> SEQUENCE: 928

000

<210> SEQ ID NO 929

<400> SEQUENCE: 929

000

<210> SEQ ID NO 930

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

<210> SEQ ID NO 941

<400> SEQUENCE: 941

000

<210> SEQ ID NO 942

<400> SEQUENCE: 942

000

<210> SEQ ID NO 943

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

000

<210> SEQ ID NO 948

<400> SEQUENCE: 948

000

<210> SEQ ID NO 949

<400> SEQUENCE: 949

000

<210> SEQ ID NO 950
<211> LENGTH: 449
<212> TYPE: PRT
<213> ORGANISM: Artificial Sequence
<220> FEATURE:
<223> OTHER INFORMATION: chemimcally synthesized

<400> SEQUENCE: 950

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
```

-continued

```
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 951
<211> LENGTH: 268
<212> TYPE: PRT
<213> ORGANISM: Artificial Sequence
<220> FEATURE:
<223> OTHER INFORMATION: chemimcally synthesized

<400> SEQUENCE: 951

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Gly Ser Gly Gly
            20                  25                  30

Ala Val Gly Leu Leu Ala Pro Pro Gly Gly Leu Ser Gly Arg Ser Asp
        35                  40                  45

Asn His Gly Gly Gly Ser Asp Ile Gln Met Thr Gln Ser Pro Ser Ser
    50                  55                  60

Leu Ser Ala Ser Val Gly Asp Arg Val Thr Ile Thr Cys Arg Ala Ser
65                  70                  75                  80

Gln Ser Ile Ser Ser Tyr Leu Asn Trp Tyr Gln Gln Lys Pro Gly Lys
                85                  90                  95

Ala Pro Lys Leu Leu Ile Tyr Ala Ala Ser Ser Leu Gln Ser Gly Val
            100                 105                 110

Pro Ser Arg Phe Ser Gly Ser Gly Ser Gly Thr Asp Phe Thr Leu Thr
        115                 120                 125

Ile Ser Ser Leu Gln Pro Glu Asp Phe Ala Thr Tyr Tyr Cys Gln Gln
    130                 135                 140

Thr Val Val Ala Pro Pro Leu Phe Gly Gln Gly Thr Lys Val Glu Ile
145                 150                 155                 160

Lys Arg Thr Val Ala Ala Pro Ser Val Phe Ile Phe Pro Pro Ser Asp
                165                 170                 175

Glu Gln Leu Lys Ser Gly Thr Ala Ser Val Val Cys Leu Leu Asn Asn
            180                 185                 190

Phe Tyr Pro Arg Glu Ala Lys Val Gln Trp Lys Val Asp Asn Ala Leu
        195                 200                 205

Gln Ser Gly Asn Ser Gln Glu Ser Val Thr Glu Gln Asp Ser Lys Asp
    210                 215                 220

Ser Thr Tyr Ser Leu Ser Ser Thr Leu Thr Leu Ser Lys Ala Asp Tyr
225                 230                 235                 240

Glu Lys His Lys Val Tyr Ala Cys Glu Val Thr His Gln Gly Leu Ser
                245                 250                 255

Ser Pro Val Thr Lys Ser Phe Asn Arg Gly Glu Cys
            260                 265
```

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959

<400> SEQUENCE: 959

000

<210> SEQ ID NO 960

<400> SEQUENCE: 960

000

<210> SEQ ID NO 961

<400> SEQUENCE: 961

000

<210> SEQ ID NO 962

<400> SEQUENCE: 962

000

<210> SEQ ID NO 963

<400> SEQUENCE: 963

000

<210> SEQ ID NO 964

<400> SEQUENCE: 964

000

<210> SEQ ID NO 965

<400> SEQUENCE: 965

000

<210> SEQ ID NO 966

<400> SEQUENCE: 966

000

<210> SEQ ID NO 967

<400> SEQUENCE: 967

000

<210> SEQ ID NO 968

<400> SEQUENCE: 968

000

<210> SEQ ID NO 969

<400> SEQUENCE: 969

000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998

<400> SEQUENCE: 998

000

<210> SEQ ID NO 999

<400> SEQUENCE: 999

000

<210> SEQ ID NO 1000

<400> SEQUENCE: 1000

000

<210> SEQ ID NO 1001

<400> SEQUENCE: 1001

000

<210> SEQ ID NO 1002

<400> SEQUENCE: 1002

000

<210> SEQ ID NO 1003

<400> SEQUENCE: 1003

000

<210> SEQ ID NO 1004

<400> SEQUENCE: 1004

000

<210> SEQ ID NO 1005

<400> SEQUENCE: 1005

000

<210> SEQ ID NO 1006

<400> SEQUENCE: 1006

000

<210> SEQ ID NO 1007

<400> SEQUENCE: 1007

000

<210> SEQ ID NO 1008

<400> SEQUENCE: 1008

000

<210> SEQ ID NO 1009

<400> SEQUENCE: 1009

000

<210> SEQ ID NO 1010

<400> SEQUENCE: 1010

000

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

<210> SEQ ID NO 1016

<400> SEQUENCE: 1016

000

<210> SEQ ID NO 1017

<400> SEQUENCE: 1017

000

<210> SEQ ID NO 1018

<400> SEQUENCE: 1018

000

<210> SEQ ID NO 1019

<400> SEQUENCE: 1019

000

<210> SEQ ID NO 1020

<400> SEQUENCE: 1020

000

<210> SEQ ID NO 1021

<400> SEQUENCE: 1021

000

<210> SEQ ID NO 1022

<400> SEQUENCE: 1022

000

<210> SEQ ID NO 1023

<400> SEQUENCE: 1023

000

<210> SEQ ID NO 1024

<400> SEQUENCE: 1024

000

<210> SEQ ID NO 1025

<400> SEQUENCE: 1025

000

<210> SEQ ID NO 1026

<400> SEQUENCE: 1026

000

<210> SEQ ID NO 1027

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

-continued

```
<210> SEQ ID NO 1031

<400> SEQUENCE: 1031

000


<210> SEQ ID NO 1032

<400> SEQUENCE: 1032

000


<210> SEQ ID NO 1033

<400> SEQUENCE: 1033

000


<210> SEQ ID NO 1034

<400> SEQUENCE: 1034

000


<210> SEQ ID NO 1035

<400> SEQUENCE: 1035

000


<210> SEQ ID NO 1036

<400> SEQUENCE: 1036

000


<210> SEQ ID NO 1037
<211> LENGTH: 6
<212> TYPE: PRT
<213> ORGANISM: Artificial Sequence
<220> FEATURE:
<223> OTHER INFORMATION: chemimcally synthesized

<400> SEQUENCE: 1037

Gly Gly Ser Gly Gly Ser
1               5
```